United States Patent
Bowdish et al.

(10) Patent No.: US 8,114,403 B2
(45) Date of Patent: Feb. 14, 2012

(54) POLYPEPTIDES AND ANTIBODIES DERIVED FROM CHRONIC LYMPHOCYTIC LEUKEMIA CELLS AND USES THEREOF

(75) Inventors: Katherine S. Bowdish, Del Mar, CA (US); John McWhirter, Chula Vista, CA (US); Anke Kretz-Rommel, San Diego, CA (US); Toshiaki Maruyama, La Jolla, CA (US)

(73) Assignee: Alexion Pharmaceuticals, Inc., Chesire, CT (US)

(*) Notice: Subject to any disclaimer, the term of this patent is extended or adjusted under 35 U.S.C. 154(b) by 0 days.

(21) Appl. No.: 12/715,303

(22) Filed: Mar. 1, 2010

(65) Prior Publication Data

US 2010/0239598 A1 Sep. 23, 2010

Related U.S. Application Data

(60) Division of application No. 12/221,122, filed on Jul. 30, 2008, now Pat. No. 7,714,110, which is a division of application No. 10/996,316, filed on Nov. 23, 2004, now Pat. No. 7,408,041, which is a continuation-in-part of application No. 10/894,672, filed on Jul. 20, 2004, which is a continuation-in-part of application No. 10/736,188, filed on Dec. 15, 2003, now abandoned, which is a continuation-in-part of application No. 10/379,151, filed on Mar. 4, 2003, now Pat. No. 7,435,412, which is a continuation-in-part of application No. PCT/US01/47931, filed on Dec. 10, 2001.

(60) Provisional application No. 60/254,113, filed on Dec. 8, 2000.

(51) Int. Cl.
*A61K 39/395* (2006.01)
(52) U.S. Cl. .................... 424/155.1; 424/133.1
(58) Field of Classification Search ............... 424/155.1, 424/133.1
See application file for complete search history.

(56) References Cited

U.S. PATENT DOCUMENTS

| | | |
|---|---|---|
| 3,940,475 A | 2/1976 | Gross |
| 4,289,747 A | 9/1981 | Chu |
| 4,376,110 A | 3/1983 | David et al. |
| 5,223,409 A | 6/1993 | Ladner et al. |
| 5,225,539 A | 7/1993 | Winter et al. |
| 5,403,484 A | 4/1995 | Ladner et al. |
| 5,427,908 A | 6/1995 | Dower et al. |
| 5,434,131 A | 7/1995 | Linsley et al. |
| 5,508,717 A | 4/1996 | Miller |
| 5,571,698 A | 11/1996 | Ladner et al. |
| 5,580,717 A | 12/1996 | Dower et al. |
| 5,780,279 A | 7/1998 | Matthews et al. |
| 5,859,205 A | 1/1999 | Adair et al. |
| 5,902,583 A | 5/1999 | Buchsbaum et al. |
| 5,916,560 A | 6/1999 | Larsen et al. |
| 6,011,138 A | 1/2000 | Reff et al. |
| 6,040,136 A | 3/2000 | Garrard et al. |
| 6,338,851 B1 | 1/2002 | Gorczynski |
| 6,632,927 B2 | 10/2003 | Adair et al. |
| 6,652,858 B2 | 11/2003 | Gorczynski et al. |
| 6,737,056 B1 | 5/2004 | Presta |
| 6,749,854 B2 | 6/2004 | Gorczynski et al. |
| 6,955,811 B2 | 10/2005 | Gorczynski et al. |
| 6,984,625 B2 | 1/2006 | Gorczynski |
| 7,238,352 B2 | 7/2007 | Gorczynski et al. |
| 2002/0031515 A1 | 3/2002 | Caligiuri et al. |
| 2002/0168364 A1 | 11/2002 | Gorczynski et al. |
| 2002/0192215 A1 | 12/2002 | Hoek et al. |
| 2003/0017491 A1 | 1/2003 | Shi et al. |
| 2004/0018972 A1 | 1/2004 | Gorczynski et al. |
| 2004/0054145 A1 | 3/2004 | Gorczynski |
| 2004/0175692 A1 | 9/2004 | Bowdish et al. |
| 2004/0198661 A1 | 10/2004 | Bowdish et al. |
| 2005/0048069 A1 | 3/2005 | Gorczynski et al. |
| 2005/0107214 A1 | 5/2005 | Gorczynski et al. |
| 2005/0129690 A1 | 6/2005 | Bowdish et al. |
| 2005/0169870 A1 | 8/2005 | Truitt et al. |
| 2006/0024231 A1 | 2/2006 | Schnitzer et al. |
| 2008/0131428 A1* | 6/2008 | Young et al. ............... 424/133.1 |

FOREIGN PATENT DOCUMENTS

| | | |
|---|---|---|
| WO | WO 84/03508 A1 | 9/1984 |
| WO | WO 85/03508 A1 | 8/1985 |
| WO | WO 92/15679 A1 | 9/1992 |
| WO | WO 94/28027 | 12/1994 |
| WO | WO 95/18825 | 7/1995 |
| WO | WO 96/27011 A1 | 9/1996 |
| WO | WO 96/38557 | 12/1996 |
| WO | WO 97/08320 A1 | 3/1997 |
| WO | WO 97/21450 | 6/1997 |
| WO | WO 88/06630 A1 | 9/1998 |
| WO | WO 99/24565 | 5/1999 |

(Continued)

OTHER PUBLICATIONS

Bruggemann et al, J. Imm., 142:3145-3150, 1989.*
Alizadeh et al., "Distinct types of diffuse large B-cell lymphoma identified by gene expression profiling," Nature, 403:503-511(2000).
Auchincloss et al. "Strategies to Induce Tolerance," Transplantation Immunology, Bach and Auchincloss, Eds., Wiley-Liss, New York, Chapter 11, pp. 211-218 (1995).
Bach, "Immunosuppressive therapy of autoimmune diseases," Immunology Today, 14(6)322-326(1993).

(Continued)

*Primary Examiner* — Misook Yu
*Assistant Examiner* — Brad Duffy
(74) *Attorney, Agent, or Firm* — Ropes & Gray LLP

(57) ABSTRACT

Cancer treatments use a therapy that: 1) interferes with the interaction between CD200 and its receptor to block immune suppression thereby promoting eradication of the cancer cells; and 2) directly kills the cancer cells either by complement-mediated or antibody-dependent cellular cytotoxicity or by targeting cells using a fusion molecule that includes a CD200-targeting portion. The therapy includes the administration of novel antibodies, functional fragments thereof or fusion molecules containing portions thereof.

3 Claims, 43 Drawing Sheets

FOREIGN PATENT DOCUMENTS

| | | |
|---|---|---|
| WO | WO 01/87336 | 11/2001 |
| WO | WO 02/11762 A2 | 2/2002 |
| WO | WO 02/42332 A2 | 5/2002 |
| WO | WO 02/059280 A2 | 8/2002 |
| WO | WO 02/095030 A2 | 11/2002 |
| WO | WO 03/025202 A2 | 3/2003 |
| WO | WO 2004/060295 A2 | 7/2004 |
| WO | WO 2004/078937 A2 | 9/2004 |
| WO | WO 2004/078938 A2 | 9/2004 |
| WO | WO-2006/053301 A2 | 5/2006 |
| WO | WO 2007/084321 A2 | 7/2007 |

OTHER PUBLICATIONS

Banerjee, D., et al., "Blocking CD200-CD200 receptor axis augments NOS-2 expression and aggravates experimental autoimmune uveoretinitis in Lewis rats," Ocular Immunology and Inflammation, 12(2):115-125 (2004).

Barclay and Ward, "Purification and Chemical Characterisation of Membrane Glycoproteins From Rat Thymocytes and Brain, Recognised by Monoclonal Antibody MRC OX2," European J. Biochemistry, 129:447-458(1982).

Barclay et al.,"CD200 and membrane protein interactions in the control of myeloid cells," Trends in Immunology, 23(6):2002.

Barclay, A.N., "Different reticular elements in rat lymphoid tissue identified by localization of Ia, Thy-1 and MRC OX 2 antigens," Immunology, 44:727-736 (1981).

Barclay, A.N., et al., "Neuronal/Lymphoid Membrane Glycoprotein MRC OX-2 is a Member of the Immunoglobulin Superfamily with a Light-Chain-Like Structure," Biochem. Soc. Symp., 51:149-157 (1985).

Bauvois et al., Constitutive expression of CD26/dipeptidylpepidase IV on peripheral blood B lymphocytes of patients with B chronic lymphocytic leukaemia. British Journal of Cancer 1999., vol. 79. p. 1042-1048.

Blazer, B.R., et al., "CD28/B7 Interactions Are Required for Sustaining the Graft-Versus-Leukemia Effect of Delayed Post-Bone Marrow Transplantation Splenocyte Infusion in Murine Recipients of Myeloid or Lymphoid Leukemia Cells," J. Immunol., 159:3460-3473 (1997).

Bodey et al. "Human Cancer Detection and Immunotherapy with Conjugated and Non-Conjugated Monoclonal Antibodies" Anticancer Research 16: 661-674 (1996).

Bohen, S.P., "Variation in gene expression patterns in follicular lymphoma and the response to rituximab," PNAS, 100(4):1926-1930(2003).

Boon, Thierry., "Toward a Genetic Analysis of Tumor Rejection Antigens," Advances in Cancer Res., 58:177-210(1992).

Borriello et al., "MRC OX-2 Defines a Novel T Cell Costimulatory Pathway," J. Immunol., 158:4549-4554(1997).

Borriello, F., et al., "Characterization and localization of Mox2, the gene encoding the murine homolog of the rat MRC OX-2 membrane glycoprotein," Mammalian Genome, 9(2):114-118 (1998).

Broderick et al., "Constitutive Retinal CD200 Expression Regulates Resident Microglia and Activin State of Inflammatory Cells During Experimental Autoimmune Uveoretinitis," Am. J. of Pathology, 161(5):1669-1677(2002).

Bukovsky, A., et al., "Association of lymphoid cell markers with rat ascitic malignant cells," IRCS Med. Sci., 11:866-867 (1983).

Bukovsky, A., et al., "Association of some cell surface antigens of lymphoid cells and cell surface differentiation antigens with early rat pregnancy," Immunology, 52:631-640 (1984).

Bukovsky, A., et al., "The localization of Thy-1.1, MRC OX 2 and Ia antigens in the rat ovary and follopian tube," Immunology, 48:587-596 (1983).

Bukovsky, A., et al., "The ovarian follicle as a model for the cell-mediated control of tissue growth," Cell Tissue Res., 236:717-724 (1984).

Caldas et al., "Humanization of the anti-CD18 antibody 6.7: an unexpected effect of a framework residue in binding to antigen," Mol. Immunol. 39:941-952 (2003).

Chaouat and Clark, FAS/FAS Ligand Interaction at the Placental Interface is not Required for the Success of Allogeneic Pregnancy in Anti-Paternal MHC Preimmunized Mice, Presented at the 6th Congress of the Adria-Alps Soc. of Immunol. of Reprod., (2000) / Amer. J. of Reprod. Immunol., 45:108-115(2001).

Chen, D., et al., "Discrete Monoclonal Antibodies Define Functionally Important Epitopes in the CD200 Molecule Responsible for Immunosupression Function," Transplantation, 79:282-288 (2005).

Chen, D., et al., "Synthetic peptides from the N-terminal regionsl of CD200 and CD200R1 modulate immunosupressive and anti-inflammatory effects of CD200-CD200R1 interaction," International Immunology, 17(3):289-296 (2005).

Chen, Z., et al., "Cloning and characterization of the murine homologue of the rat/human MRC OX-2 gene," Database Medline, Biochemica et Biophysica Acta, 1362(1):6-10 (1997).

Cherwinski, H.M., et al., "The CD200 Receptor Is a Novel and Potent Regulator of Murine and Human Mast Cell Function," J. Immunol., 174:1348-1356 (2005).

Chien et al., "Significant structural and functional change of an antigen-binding site by a distant amino acid substitution: proposal of a structural mechanism," Proc. Natl. Acad. Sci. USA 86:5532-5536 (1989).

Chitnis et al., "The Role of CD200 in Immune-Modulation and Neural Protection in EAE," Abstract, 12th International Congress of Immunology and 4th Annual Conference of FOCIS, Montreal, Jul. 21, 2004.

Chitnis, T., et al., "Elevated Neuronal Expression of CD200 Protects $Wld^s$ Mice from Inflammation-Mediated Neurodegeneration," American Journal of Pathology, 170(5):1695-1712 (2007).

Clark et al., "Fgl2 prothrombinase expression in mouse trophoblast and decidua triggers abortion but may be countered by OX-2," Mol. Human Reprod., 7:185-194(2001).

Clark et al., "Labile CD200 tolerance signal important in transfusion-related immunomodulation (TRIM) prevention of recurrent miscarriages," Amer. J. Reprod. Immunol., 45:361(2001).

Clark et al., "Procoagulants in fetus rejection: the role of the OX-2 (CD200) tolerance signal," Seminars in Immunol., 13(4)255-263(2001).

Clark et al., "The OX-2 Tolerance Signal Molecule at the Fetomaternal Interface Determines Pregnancy Outcome," Amer. Journal of Reprod Immunol., 43:326(2000). Abstract Only.

Clark et al., Amer. Soc. for Reprod. Medicine, 55th Annual Meeting (1999).

Clark, D.A., "Intralipid as Treatment for Recurrent Unexplained Abortion?", Am. J. of Reprod. Immunol., 32:290-293(1994).

Clark, M.J., et al., "MRC OX-2 antigen: a lymphoid/neuronal membrane glycoprotein with a structure like a single immunoglobulin light chain," EMBO Journal, 4(1):113-118 (1985).

Clarke, M.J., "MRC OX-2 lymphoid brain glycoprotein: S1 mapping suggests higher levels of abnormal RNA in the thymus than in the brain," Biochemical Society Transactions, 14:80-81 (1986).

Cochlovius et al., "Cure of Burkitt's Lymphome in Severe Combined Immunodeficiency Mice by T Cells, Tetravalent CD3 x CD19 Tandem Diabody, and CD28 Costimulation," Cancer Res. 60:4336-4341 (2000).

Cohen, P.L., "Systemic Autoimmunity," in Fundamental Immunology, Fourth edition, W.E. Paul, Editor, Lippincott-Raven Publishers, Philadelphia, Ch. 33, p. 1067-1088(1999).

DeNardo et al., " Increased Survival Associated with Radiolabeled Lym-1 Therapy for Non-Hodgkin's Lymphoma and Chronic Lymphocyctic Leukemia." Cancer Supplement (1997) vol. 80, No. 12. pp. 2706-2711.

Dennis, C., "Off by a whisker," Nature, 442,:739-741 (2006).

Dick et al., "Control of Myeloid Activity During Retinal Inflammation," J. of Leukocyte Bio., 74:161-166(2003).

Ebert et al., "Selective Immunosuppressive Action of a Factor Produced by Colon Cancer Cells," Cancer Res. 50:6158-6161 (1990).

Elgert, K. D. "Immunology : Understanding the Immune System," The Genetic Basis of Antibody Diversity, 123 (1996).

Faguet et al., "Blood Kinectics, Tissue Distribution, and Radioimaging of Anti-Common Chronic Lymphatic Leukemia Antigen (cCLLa) Monoclonal Antibody $CLL_2$ in Mice Transplanted With cCLLa-Bearing Human Leukemia Cells." Blood. vol. 75, No. 9 (1990) pp. 1853-1861.

Faisal et al., Cell-surface Associated p43/Endothelial-monocyte-activating-polypeptide-II in Hepatocellular Carcinoma Cells Induces Apoptosis in T-lynphocytes, Asian J. of Surg. 30(1):13-22 (2007).
Fallarino, F., et al., "Murine Plasmacytoid Dendritic Cells Initiate the Immunosupressive Pathway of Tryptophan Catabolism in Response to CD200 Receptor Engagement," J. Immunol., 173:3748-3754 (2004).
Farber, U., et al., "Loss of heterozygosity on chromosome 3, bands q24->qter, in a diploid meningioma," Cytogenet Cell Genet, 57:157-158 (1991).
Feuerstein et al., 1999, Induction of Autoimmunity in a Transgenic Model of B Cell Receptor Peripheral Tolerance: Changes in Coreceptors and B Cell Receptor-Induced Tyrosine-Phosphoproteins, J. Immunol. 163:5287-5297.
Funakoshi et al., "Antitumor Effects of Nonconjugated Murine Lym-2 and Human-Mouse Chimeric CLL-1 Monoclonal Antibodies Against Various Human Lumphoma Cell Lines In Vitro and In Vivo." Blood vol. 90, No. 8 (1997) pp. 3150-3166.
Ginaldi et al., "Levels of expression of CD52 in normal and leukemic B and T cells: correlation with in vivo therapeutic responses to Campath-1H," Leukemia Res. 22(2):185-191 (1998).
Giusti et al., "Somatic diversification of S107 from an antiphosphocholine to an anti-DNA autoantibody is due to a single base change in its heavy chain variable region," Proc. Natl. Acad. Sci. USA 84:2926-2930 (1987).
Gorczynski and Marsden, "Modulation of CD200 receptors as a novel method of immunosuppression," Expert Opin. Ther. Patents, 13(5): 711-715(2003). See also WIPO Patent No. WO02095030 assigned to Transplantation Tech, Inc.
Gorczynski et al., "Anti-CD200R Ameliorates Collagen-Induced Arthritis in Mice," J. of Immunol., 104(3):256-264(2002).
Gorczynski et al., "Does Successful Allopregnancy Mimic Transplantation Tolerance?", Graft, 4:338-345(2001).
Gorczynski et al., "Evidence of a role for CD200 in regulation of immune rejection of leukaemic tumour cells in C57BL/6 mice," Clin. Exp. Immunol., 126:220-229(2001).
Gorczynski et al., "Increased Expression of the Novel Molecule OX-2 IS Involved in Prolongation of Murine Renal Allograft Survival," Transplantation, vol. 65(8); pp. 1106-1114 (1998).
Gorczynski, "CD200 and Its Receptors as Targets for Immnoregulation" Current Opinion in Investigational Drugs, Pharmapress, US, vol. 6, No. 5, May 2005, pp. 483-488. XP008051169 ISSN: 1472-4472.
Gorczynski, L., et al., "Evidence That an OX-2-Positive Cell Can Inhibit the Stimulation of Type 1 Cytokine Production by Bone Marrow-Derived B7-1 (and B7-2)-Positive Dendtritic Cells," J. Immunol., 162:774-781 (1999).
Gorczynski, R., et al., "CD200 Is a Ligand for All Members of the CD200R Family of immunoregulatory Molecules," J. Immunol., 172:7744-7749 (2004).
Gorczynski, R., et al., "Dendritic Cells Expressing TGFBeta/IL-10, and CHO Cells With OX-2, Increase Graft Survival," Transplantation Proceedings, 33:1565-1566 (2001).
Gorczynski, R.M., "Role of Cytokines in Allograft Rejection," Current Pharmaceutical Design, 7:1039-1057 (2001).
Gorczynski, R.M., "Synergy in Induction of Increased Renal Allograft Survival after Portal Vein Infusion of Dendtritic Cells Transduced to Express TGFB and IL-10, along with Administration of CHO Cells Expressing the Regulatory Molecule OX-2," Clinical Immunology, 95(3):182-189 (2000).
Gorczynski, R.M., "Transplant tolerance modifying antibody to CD200 receptor, but not CD200, alters cytokine production profile from stimulated macrophages," Eur. J. Immunol., 31:2331-2337 (2001).
Gorczynski, R.M., et al., "A CD200FC Immunoadhesin Prolongs Rat Islet Xenograft Survival in Mice," Transplantation, 73(12):1948-1953 (2002).
Gorczynski, R.M., et al., "An Immunoadhesin Incorporating the Molecule OX-2 Is a Potent Immunosuppressant That Prolongs Allo- and Xenograft Survival," J. Immunol., 163:1654-1660(1999).
Gorczynski, R.M., et al., "Anti-Rat OX-2 Blocks Increased Small Intestinal Transplant Survival After Portal Vein Immunization," Transplantation Proceedings, 31:577-578 (1999).
Gorczynski, R.M., et al., "Augmented Induction of CD4+ CD25+ Treg using Monoclonal Antibodies to CD200R," Transplantation, 79(4):488-491 (2005).
Gorczynski, R.M., et al., "Augmented Induction of CD4+ CD25+ Treg using Monoclonal Antibodies to CD200R," Transplantation, 79(9):1180-1183 (2005).
Gorczynski, R.M., et al., "CD200 Immunoadhesin Supresses Collagen-Induced Arthritis in Mice," Clinical Immunology, 101(3):328-334 (2001).
Gorczynski, R.M., et al., "Evidence for Persistent Expression of OX2 as a Necessary Component of Prolonged Renal Allograft Survival Following Portal Vein Immunization," Clinical Immunol., 97(1):69-78 (2000).
Gorczynski, R.M., et al., "Induction of Tolerance-Inducing Antigen-Presenting Cells in Bone Marrow Cultures in Vitor Using Monoclonal Antibodies to CD200R," Transplantation, 77(8):1138-1144 (2004).
Gorczynski, R.M., et al., "Interleukin-13, in Combination with Anti-Interleukin-12, Increases Graft Prolongation After Portal Venous Immunization with Cultured Allogeneic Bone Marrow-Derived Dentritic Cells," Transplantation, 62(11):1592-1600 (1996).
Gorczynski, R.M., et al., "Persistent expression of OX-2 is necessary for renal allograft survival," FASEB Journal, 14(6):A1069 (2000).
Gorczynski, R.M., et al., "Receptor Engagement on Cells Expressing a Ligand for the Tolerance-Inducing Molecule OX2 Induces an Immunoregulatory Population That Inhibits Alloreactivity In Vitro and In Vivo," J. Immunol., 165:4854-4860 (2000).
Gorczynski, R.M., et al., "Regulation of Gene Expression of Murine MD-1 Regulates Subsequent T Cell Activation and Cytokine Production," J. of Immunology, 165:1925-1932 (2000).
Gorczynski, R.M., et al., "Structural and Functional Heterogeneity in the CD200R Family of Immunoregulatory Molecules and their Expression at the Fetomaternal Interface," AJRI, 52:147-163 (2004).
Gorczynski, R.M., et al., "The Same Immunoregulatory Molecules Contribute to Successful Pregnancy and Transplantation," AJRI, 48:18-26 (2002).
Gorczynski, "Evidence for an Immunoregulartory Role of OX2 with its Counter Ligand (OX2L) in the Regulation of Transplant Rejection, Fetal Loss, Autoimmunity and Tumor Growth, " Archibum Immunologiae et Therapiae Experimentalis, vol. 49(4) pp. 303-309 (2001).
Gura, T., "Systems for Identifying New Drugs Are Often Faulty," Science, 278:1041-1042 (1997).
Gussow and Seemann, "Humanization of Monoclonal Antibodies," Meth. Enzymol. 203:99-121 (1991).
Hardy et al., "A lymphocyte-activating monoclonal antibody induces regression of human tumors in severe combined immunodeficient mice," Proc. Natl. Acad. Sci. USA 94:5756-5760 (1997).
Hart, P.H., "Modulation of Monocyte Effector Functions by Lipopolysacc-haride and Interferon-Y," Dept. of Medicine, University of Melbourne, Royal Melbourne Hospital, Parkville, Vic., 3050 (Abstract).
Heaney et al., "Severe asthma treatment: need for characterising patients," Lancet, 365:974-976(2005).
Hoek, R.M., et al., "Down-Regulation of the Macrophage Lineage Through Interaction with OX2 (CD200)," Science, 290:1768-1771 (2000).
Hoek, R.M., et al., "Macrophage regulation by the B7.1/2 homologue OX2?", FASB Journal, 14(6):A1232 (2000).
Huang, "Structural chemistry and therapeutic intervention of protein-protein interactions in immune response, human immunodeficiency virus entry, and apoptosis," Pharmacol. Therapeutics, 86:201-215(2000).
Hutchings, N.J., et al., "Interactions of Cytoplasmic Region of OX2R Are Consistent with an Inhibitory Function," Annual Congress of the British Society for Immunology, Dec. 5-8, 2000, Harrogate, UK.
Iwanuma et al., "Antitumor Immune Response of Human Peripheral Blood Lymphocytes Coengrafted with Tumor into Severe Combined Immunodeficient Mice," Cancer Res. 57:2937-2942 (1997).
Jain, "The next frontier of molecular medicine: Delivery of therapeutics," Nature Medicine, 4(6):655-657(1998).

Jansky, L., et al., "Dynamics of Cytokine Production in Human Peripheral Blood Mononuclear Cells Stimulated by LPS or Infected by Borrelia," Physiol. Res., 52:593-598 (2003).

Jeurissen, S.H.M., et al., "Characteristics and functional aspects of nonlymphoid cells in rat germinal centers, recognized by two monoclonal antibodies ED5 and ED6," Eur. J. Immunol., 16:562-568 (1986).

Keil et al., "The Tolerance-Promoting Molecule OX-2 is Expressed in Fetal Trophoblast Cells that Cocoon the 'Fetal Allograft' and may prevent Pregnancy Loss Caused by Cytokine-Activation of FGL2 Prothrombinase," Amer. J. Reprod. Immunol., 45:343(2001) (abstract).

Kim et al., "Divergent Effects of 4-1BB Antibodies on Antitumor Immunity and on Tumor-reactive T-Cell Generation," Cancer Res., 61:2031-2037(2001).

Kjaergaard et al., "Therapeutic Efficacy of OX-40 Receptor antibody Depends on Tumor Immunogenicity and Anatomic Site of Tumor Growth," Cancer Res. 60:5514-5521(2000).

Kneitz, C., et al., "Inhibition of Tcell/B cell interaction by B-CLL cells," Leukemia, 13:98-104 (1999).

Kretz-Rommel Anke et al: "CD200 Expression On Tumor Cells Suppresses Anti-Tumor Immunity: New Approaches To Cancer Immunotherapy" Journal Of Immunotherapy; vol. 29, No. 6, Nov. 2006, p. 666, xp009088616 & 21st Annual Scientific Meeting Of The International-Society-For-Biological-Therapy-Of-Cancer; Los Angeles, CA, USA; Oct. 26-29, 2006 ISSN: 1524-9557.

Kretz-Rommel, "CD200 Expression on Tumor Cells Suppresses Antitumor Immunity: New Approaches to Cancer Immunotherapy," J. Immunol. 178:5595-5605 (2007).

Kretz-Rommel, A., et al., "Immune Evasion by CD200: New Approaches to Targeted Therapies for Chronic Lymphocytic Leukemia," J. Immunother., 28(6):650 (2005).

Kretz-Rommel, A., et al., "The Immuno-Regulatory Protein CD200 Is Overexpressed in a Subset of B-Cell Chronic Lymphocytic Leukemias and Plays a Role in Down-Regulating the TH1 Immune Response," J. Immunother., 27(6):546 (2004).

Kroese, F.G.M., et al., "Germinal centre formation and follicular antigen trapping in the spleen of lethally X-irradiated and reconstituted rats," Immunology, 57:99-104 (1986).

Kroese, F.G.M., et al., "The ontogeny of germinal centre forming capacity of neonatal rat spleen," Immunology, 60:597-602 (1987).

Liu et al., "Effect of combined T- and B-cell depletion of allogenic HLA-mismatched bone marrow graft on the magnitude and kinetics of Epstein-Barr virus load in the peripheral blood of bone marrow transplant recipients," Clin. Transplant. 18:518-524 (2004).

Mariuzza et al., "The Structural Basis of Antigen-Antibody Recognition," Ann. Rev. Biophys. Biophys. Chem. 16:139-159 (1987).

Marsh, M.N., "Functional and Structural Aspects of the Epithelial Lymphocyte, with Implications for Coeliac Disease and Tropical Sprue," Univ. Dept. of Medicine, University of Manchester School of Medicine at Hope Hospital, Salford, Manchester UK pp. 55-75 (1985).

Matutes et al. Morphological and Immuniphenotypic Features of Chronic Lymphocytic Leukemia. Rev. Clin. Exp. Hematol. vol. 4.1, Mar. 2000 p. 22-47.

McCaughan et al., "Characterization of the Human Homolog of the Rat MRC OX-2 Membrane Glycoprotein," Immunogenetics, 25:329-335(1987).

McCaughan, G.M., et al., "Identification of the human homologue of the rat lymphoid/brain antigen MRC OX-2," Australian and New Zealand Journal of Medicine 17: 142 (Abstract) (1987).

McCaughan, G.W., et al., "The Gene for MRC OX-2 Membrane Glycoprotein Is Localized on Human Chromosome 3," Immunogenetics, 25:133-135 (1987).

McMaster, W.R., et al., "Identification of Ia glycoproteins in rat thymus and purification from rat spleen," Eur. J. Immunol., 9:426-433 (1979).

McWhirter, J.R., et al., "Antibodies selected from combinatorial libraries block a tumor antigen that plays a key role in immunomodulation," PNAS, 103(4):1041-1046 (2006).

Mjaaland et al., "Modulation of immune responses with monoclonal antibodies. I. Effects on regional lymph node morphology and on anti-hapten responses to haptenized monoclonal antibodies", Eur. J. Immunol., 20:1457-1461(1990).

Mjaaland, S., et al., "The Localization of Antigen in Lymph Node Follicles of Congenitally Athymic Nude Rats," Scand. J. Immunol., 26:141-147 (1987).

Mohammad, R.M., et al., "Establishment of a human B-CLL xenograft model: utility as a preclinical therapeutic model," Leukemia, 10:130-137 (1996).

Mori et al., "Establishment of a new anit-cancer drugs-resistant cell line derived from B-chronic lymphocyctic leukemia" Proceedings, Fifty-Ninth Annual Meeting of teh Japanese Cancer Association, p. 583, # 3788 (Sep. 1, 2000).

Morris, R.J., et al., "Sequential Expression of OX2 and Thy-1 Glycoproteins on the Neuronal Surface during Development," Dev. Neurosci., 9:33-44 (1987).

Myers et al., "Characterization of a Peptide Analog of a Determinant of Type II Collagen that Suppresses Collagen-Induced Arthritis," J. of Immunology, 3589-3595(1998).

Nagelkerken L., et al., "Accessory Cell Function of Thoracic Duct Nonlymphoid Cells, Dentritic Cells, and Splenic Adherent Cells in the Brown-Norway Rat," Cellular Immunology, 93:520-531 (1985).

Nathan and Muller, "Putting the Brakes on innate immunity: a regulatory role for CD200?", Nat Immunol., 2(1):17-19(2001).

Ni et al., "An immunoadhesin incorporating the molecule OX-2 is a potent immunosuppressant which prolongs allograft survival", FASEB Journal 13(5):A983(1999).

Pardoll, Drew., "Therapeutic Vaccination for Cancer," Clin. Immunol., 95(1):S44-S62(2000).

Paterson, D.J., et al., "Antigens of Activated Rat T Lymphocytes Including A Molecule of 50,000 Mr Detected Only on CD4 Positive T Blasts," Molecular Immunology, 24(12):1281-1290 (1987).

Preston et al., "The leukocyte/neuron cell surface antigen OX2 binds to a ligand on macrophages", European J. of Immunol., 27(8):1911-1918(1997).

Ragheb et al., "Preparation and functional properties of monoclonal antibodies to human, mouse and rat OX-2", Immunol. Letters, 68(2,3):311-315(1999).

Ragheb, R.F., "Exploration of OX-2 function in tolerance induction and graft acceptance using an anti-mouse OX-2 monoclonal antibody," Masters Abstracts International, 38(4):971-972 (2000).

Richards, S.J., et al., "Reported Sequence Homology Between Alzheimer Amyloid770 and the MCR OX-2 Antigen Does Not Predict Function," Brain Research Bulletin, 38(3):305-306 (1995).

Riley, "Melanoma and the Problem of Malignancy," J. Exp. Med. 204:1-9 (2004).

Rioux, P., Campath-1H (Cambridge Univeristy), IDrugs, vol. 2(2); pp. 153-167 Database Medline, abstract No. NLM16160950 (Abstract Only) (1999).

Romagnani, Sergio., "Short Analytical Review: TH1 and TH2 in Human Diseases," Clin. Immunol. Immunopath, 80(3):225-235(1996).

Rosenblum, M.D., et al., "CD200 is a novel p53-target gene involved in apoptosis-associated immune tolerance," Blood, 103(7):2691-2698 (2004).

Rosenwald et al., "Relation of Gene Expression Phenotype to Immunoglobulin Mutation Genotype in B Cell Chronic Lymphocytic Leukemia," J. of Exp. Medicine, 194(11):1639-1647(2001).

Rudicoff et al., "Single amino acid substitution altering antigen-binding specificity," Proc. Natl. Acad. Sci. USA 79:1979-1983 (1982).

Sahin et al., "New monoclonal antibody specific for a 6.5 kDa glycoprotein which presents mainly on a B cell of chronic lymphocytic leukemia (CLL)" Immunology Letters, 2001, 76, 1-6.

Schlom, Jeffrey :Monoclonal Antiboides They're More and Less Than You Think, Molecular and Cellular Research for Future Diagnosis and Therapy, 95-134, 1991.

Schultes et al., "Immunotherapy of Human Ovarian Carcinoma with Ovarex™ MAb-B43.13 in a Human-PBL-SCID/BG Mouse Model," Hybridoma 18(1):47-55 (1999).

Sebestyen et al., Syndecan-1 (CD138) expression in human non-Hodgkin lymphomas. British Jounal of Hematology. vol. 104, 1999, p. 412-419.

Sehgal, et al., "Generation of the Primary Antibody Repertoire in Rabbits: Expression of a Diverse Set of Igk-V Genes May Compensate for Limited Combinatorial Diversity at the Heavy Chain Locus," Immunogenetics 50:31-42 (1999).

Simelyte et al., "CD200-Fc, a Novel Antiarthritic Biologic Agent That Targets Proinflammatory Cytokine Expression in the Joints of Mice With Collagen-Induced Arthritis," Arthritis & Rheumatism, vol. 58(4), pp. 1038-1043 (2008).

Snyder et al., "Enhanced Targeting and Killing of Tumor Cells Expressing the CXC Chemokine Receptor 4 by Transducible Anticancer Peptides," Cancer Res. 65(23):10646-10650 (2005).

Srivastava, P.K., "Immunotherapy of human cancer: lessons from mice," Nature Immunology, 1(5):363-366 (2000).

Steinman, Lawrence., "Assessment of Animal Models for MS and Demyelinating Disease in the Design of Rational Therapy," Neuron, 24:511-514(1999).

Stuart et al., "Monkeying Around with Collagen Autoimmunity and Arthritis," Laboratory Investigation, vol. 54(1), pp. 1-3 (1986).

Syme, R., et al., "Comparison of CD34 and Monocyte-Derived Dendritic Cells from Mobilized Peripheral Blood from Cancer Patients," Stem Cells, 23:74-81 (2005).

Tanaka et al., "The Anti-Human Tumor Effect and Generation of Human Cytotoxic T Cells in SCID Mice Given Human Peripheral Blood Lymphocytes by the in Vivo Transfer of the Interleukin-6 Gene Using Adenovirus Vector," Cancer Res. 57:1335-1343 (1997).

Tang et al., Pathogenesis of collagen-induced arthritis: modulation of disease by arthritogenic T-Cell epitope location, J. of Immunology, 113: 384-391.

Tangri and Raghupathy, "Expression of Cytokines in Placentas of Mice Undergoing Immunologically Mediated Spontaneous Fetal Resorptions," Biology of Reprod., 49:850-856(1993).

Taylor, N., et al., "Enhanced Tolerance to Autoimmune Uveitis in CD200-Deficient Mice Correlates with a Pronounced Th2 Switch in Response to Antigen Challenge," J. Immunol., 174:143-154 (2005).

Thomsen et al., "Reconstitution of a human immune system in immunodeficient mice: models of human alloreaction in vivo," Tissue Antigens 66:73-82 (2005).

Toder et al., "Mouse Model for the Treatment of Immune Pregnancy Loss," Am. J. of Reprod. Immunol., 26:42-46(1991).

Webb, M., et al., "Localisation of the MRC OX-2 Glycoprotein on the Surfaces of Neurones," J. Neurochemistry, 43:1061-1067 (1984).

Wilczynski, J.R., "Immunoligical Analogy Between Allograft Rejection, Recurrent Abortion and Pre-Eclampsia—the Same Basic Mechanism?," Human Ummunology, 67:492-511 (2006).

Wright et al., "The unusual distribution of the neuronal/lymphoid cell surface CD200 (OX2) glycoprotein is conserved in himans," Immunology 102:173-179 (2001).

Wright, G.J., et al., "Lymphoid/Neuronal Cell Surface OX2 Glycoprotein Recognizes a Novel Receptor on Macrophages Implicated in the Control of Their Function," Immunity, 13:233-242 (2000).

Wright, G.J., et al., "The lymphoid/neuronal OX-2 glycoprotein interacts with a novel protein expressed by macrophages," Tissue Antigens, 55 (Supplement 1); vol. 11 (2000).

Wright, G.J., et al., "Viral homologues of cell surface proteins OX2 and CD47 have potential to regulate macrophage function," Annual Congress of the British Society for Immunology, vol. 101 (Supplement 1): 50 Dec. 5-8, 2000.

Yang, C., et al., "Functional maturation and recent thymic emigrants in teh periphery: development of alloreactivity correlates with the cyclic expression of CD45RC isoforms," Eur. J. Immunol., 22:2261-2269 (1992).

Yu, X., et al., "The role of B7-CD28 co-stimulation in tumor rejection," International Immunology, 10(6):791-797 (1998).

Zhang, S., et al., "Molecular Mechanisms of CD200 Inhibition of Mast Cell Activation," J. Immunol., 173:6786-6793 (2004).

Zheng, P., et al., "B7-CTLA4 interaction enhances both production of antitumor cytotoxic T lymphocytes and resistance to tumor challenge," Proc. Natl. Acad. Sci. USA, 95:6284-6289 (1998).

Zhu et al., "Radioimmunotherapy of Human B-Cell Chronic Lymphocytic Leukemia in Nude Mice." Cancer Research. 54, 5111-5117 (1994).

Zips, D., et al., "New Anticancer Agents: In Vitro and In Vivo Evaluation," in vivo, 19:1-7 (2005).

Zou et al. Human Glioma-Induced Immunosuppression Involves Soluble Factor(s) That Alters Monocyte Cytokine Profile and Surface Markers. Apr. 15, 1999. vol. 162, pp. 4882-4892.

Ohno et al., "Antigen-binding specificities of antibodies are primarily determined by seven residues of $V_H$," Proc. Natl. Acad. Sci., vol. 82, pp. 2945-2949 (1985).

Pakula and Sauer, "Genetic analysis of protein stability and function," Annu. Rev. Genet., vol. 23, pp. 289-310 (1989).

Panka et al., "Variable region framework differences result in decreased or increased affinity of variant anti-digoxin antibodies," Proc, Natl. Acad. Sci. USA, vol. 85:3080-3084 (1988).

Tao et al., "Structural Features of Human Immunoglobulin G that Determine Isotype-specific Differences in Complement Activation," J. Exp. Med., vol. 178, pp. 661-667 (1993).

Greenwood, J.D. and Clark, M., "Protein Engineering of Antibody Molecules for Prophylactic and Therapeutic Applications in Man," (ed. Clark, M.) Pub. Academic Titles, UK, pp. 4-5 (1993).

\* cited by examiner

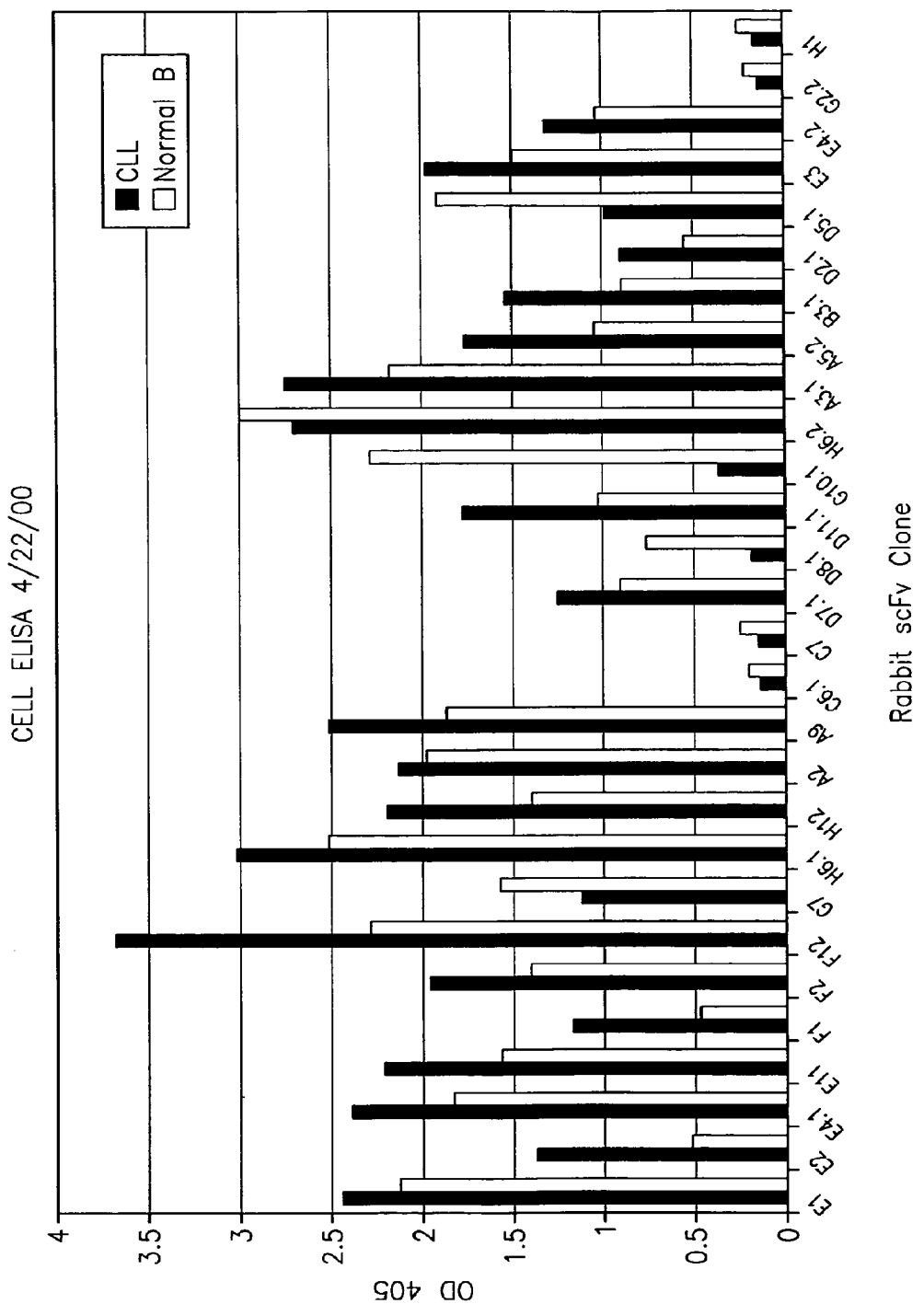

FL2: scFv-9/HA-biotin/SA-PE
FL1: CD5-FITC
FL3: CD19-PerCP

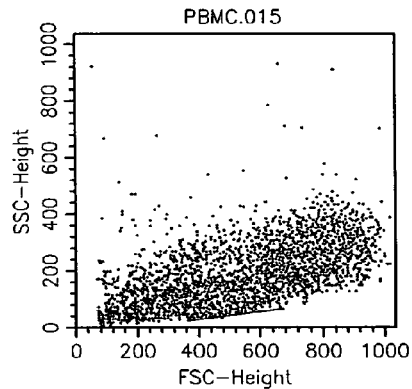
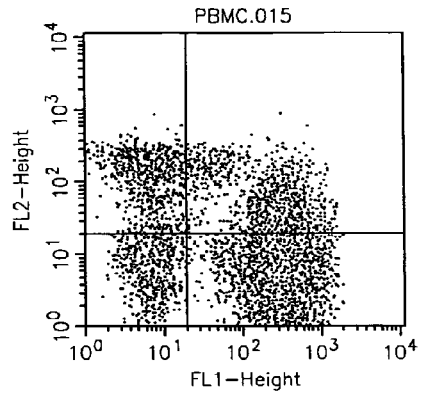

File: PBMC.015
XParameter: FL1-H FL1-Height (Log)
YParameter: FL2-H FL2-Height (Log)

| Quad | Events | %Gated | %Total | XGeo Mean | YGeo Mean |
|---|---|---|---|---|---|
| UL | 1881 | 9.40 | 5.84 | 6.45 | 118.74 |
| UR | 4368 | 21.84 | 13.56 | 266.89 | 45.49 |
| LL | 2831 | 14.16 | 8.79 | 6.65 | 7.40 |
| LR | 10920 | 54.60 | 33.90 | 282.52 | 5.72 |

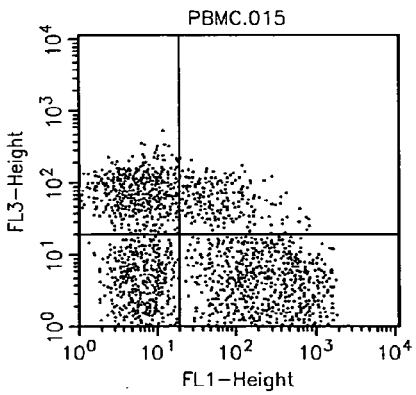
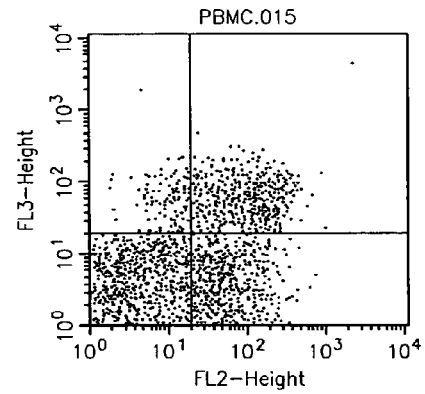

File: PBMC.015
XParameter: FL1-H FL1-Height (Log)
YParameter: FL3-H FL3-Height (Log)

| Quad | Events | %Gated | %Total | XGeo Mean | YGeo Mean |
|---|---|---|---|---|---|
| UL | 1874 | 9.37 | 5.82 | 6.55 | 65.56 |
| UR | 409 | 2.04 | 1.27 | 50.57 | 55.81 |
| LL | 2838 | 14.19 | 8.81 | 6.57 | 4.19 |
| LR | 14879 | 74.39 | 46.19 | 291.30 | 2.17 |

File: PBMC.015
XParameter: FL2-H FL2-Height (Log)
YParameter: FL3-H FL3-Height (Log)

| Quad | Events | %Gated | %Total | XGeo Mean | YGeo Mean |
|---|---|---|---|---|---|
| UL | 171 | 0.85 | 0.53 | 10.16 | 54.88 |
| UR | 2112 | 10.56 | 6.56 | 137.20 | 64.47 |
| LL | 13744 | 68.72 | 42.67 | 6.08 | 2.52 |
| LR | 3973 | 19.86 | 12.33 | 41.31 | 2.06 |

*FIG. 7*

Table 1. Summary of CLL scFv Clones

| Pool | Clone | CLL | Primary B | CLL-AAT | RL (NHL) | Ramos (Burkitt's) | TF1 | Patient-Specific | Expression Lost | Fingerprint |
|---|---|---|---|---|---|---|---|---|---|---|
| R3/RSC-S CLL-TF1 | E1 | ++ | ++ | ++ | – | – | – | | | 1 |
| | E2 | + | – | + | – | – | – | | | 2 |
| | E4.1 | ++ | + | ++ | ± | ± | ± | | | 3 |
| | E11 | ++ | + | ++ | – | – | – | | | 4 |
| | F1 | + | – | + | – | – | – | | | 5 |
| | F2 | ++ | + | ++ | – | – | – | | | 6 |
| | F12 | ++ | + | ++ | – | – | – | | | 7 |
| | G7 | + | + | + | + | + | + | | | 8 |
| | H6.1 | ++ | + | ++ | + | + | – | | | 7 |
| | H12 | ++ | + | ++ | – | – | – | | | 9 |
| | A2 | ++ | ++ | ++ | + | + | – | | | 10 |
| | A9 | ++ | + | ++ | – | – | – | | | 11 |
| | C6.1 | – | – | nd | nd | nd | nd | + | | 12 |
| | C7 | – | – | nd | nd | nd | nd | + | | 13 |
| | D7.1 | + | + | + | + | + | + | | | 14 |
| | D8.1 | – | + | nd | nd | nd | nd | +? | | 15 |
| | D11.1 | ++ | + | ++ | – | – | – | | | 16 |
| | G10.1 | + | + | + | – | – | – | | | 17 |
| | H6.2 | ++ | ++ | ++ | – | – | – | | | 18 |
| | A3.1 | ++ | + | ++ | – | – | – | | | 19 |
| | A5.2 | ++ | + | ++ | – | – | – | | | 20 |
| | B3.1 | + | + | + | – | – | – | | | 9 |
| | D2.1 | + | + | + | – | – | – | | | 21 |
| | D5.1 | + | + | + | ± | ± | ± | | | 22 |
| | E3 | + | + | + | – | – | – | | | 23 |
| | E4.2 | + | + | + | – | – | – | | | 24 |
| | G2.2 | – | – | nd | nd | nd | nd | + | | 25 |
| | H1 | – | – | nd | nd | nd | nd | + | | 26 |
| | H6.3 | – | – | nd | nd | nd | nd | + | | 27 |
| R3/RSC-L CLL-TF1 | A8 | – | + | + | nd | nd | nd | +? | | 28 |
| | B12.1 | + | + | ++ | nd | nd | nd | | | 29 |
| | C12 | ++ | + | ++ | + | + | ± | | | 30 |
| | D1.1 | + | + | + | nd | nd | nd | | | 31 |
| | D5.2 | – | – | + | nd | nd | nd | +? | + | 32 |
| | D8.2 | ++ | + | ++ | + | + | ± | | | 33 |
| | F10 | ++ | + | ++ | + | + | ± | | | 34 |
| | A1.1 | + | + | ++ | nd | nd | nd | | | (nd) |
| | G9 | ±? | + | ++ | nd | nd | nd | +? | | (nd) |
| R5/RSC-L CLL-B | B1 | + | + | + | nd | nd | nd | | | 35 |
| | B4.2 | ++ | + | ++ | nd | nd | nd | | | 36 |
| | C10 | ++ | + | ++ | nd | nd | nd | | | 37 |
| | D4.2 | – | – | – | nd | nd | nd | +? | + | 38 |
| | D11.2 | ±? | – | + | nd | nd | nd | +? | | 39 |
| | G1.2 | ++ | + | ++ | – | – | – | | | 37 |
| | D2.2 | + | + | + | nd | nd | nd | | | 40 |
| | G12.1 | + | + | + | + | + | – | | | 41 |
| R4/RSC-S CLL-B | A1.2 | ±? | nd | ++ | nd | nd | nd | +? | | 42 |
| | A3.2 | + | nd | ++ | + | + | ± | | | 43 |
| | B3.2 | – | nd | + | nd | nd | nd | + | | 44 |
| | B4.3 | – | nd | ++ | nd | nd | nd | + | | 45 |
| | B12.2 | + | nd | ++ | + | + | ± | | | 46 |
| | C4 | ++ | nd | ++ | – | – | – | | | 47 |
| | E8.2 | ++ | nd | ++ | – | – | – | | | 48 |
| | F7 | + | nd | ++ | + | + | – | | | 46 |
| | D7.2 | ++ | nd | ++ | + | + | ± | | | 49 |
| | D12 | ++ | nd | ++ | + | + | + | | | 50 |
| | E5 | ++ | nd | ++ | + | + | – | | | 51 |
| | E6.2 | + | nd | ++ | + | + | + | | | 52 |
| | E7.2 | + | nd | ++ | + | + | + | | | 53 |
| | F5.2 | + | nd | ++ | + | + | – | | | 54 |

CLL + Primary B Cells
CLL Cells
CLL + All B Cells
CLL + All B Cells + TF1dim
CLL + All B Cells + TF1bright
patient-specific or lost expression
not fully characterized

*FIG. 9a*

Table 1. CDR Sequence of CLL Specific Rabbit scFv Antibodies

| CLONE | LC-CDR1 | | LC-CDR2 | | LC-CDR3 | |
|---|---|---|---|---|---|---|
| A2c | TLSTGYSVGSYVIA | (SEQ ID NO: 1) | HSEEAKHQGS | (SEQ ID NO: 18) | ATAHGSGSSFHVV | (SEQ ID NO: 25) |
| G12.1c | QASESIRN---YLA | (SEQ ID NO: 2) | GASNL----ES | (SEQ ID NO: 19) | QSGDYSA---GLT | (SEQ ID NO: 26) |
| B4.2a | QASESIRN---YLA | (SEQ ID NO: 2) | GASNL----ES | (SEQ ID NO: 19) | QSGYYSA---GLT | (SEQ ID NO: 27) |
| E1c | QASESISN---WLA | (SEQ ID NO: 3) | RASTL----AS | (SEQ ID NO: 20) | QSGYYSA---GVT | (SEQ ID NO: 28) |
| F2d | QASESISN---YLA | (SEQ ID NO: 4) | GASNL----ES | (SEQ ID NO: 19) | QSGYYSA---GLT | (SEQ ID NO: 27) |
| E5e | QASQNIYS---NLA | (SEQ ID NO: 5) | LAFTI----AS | (SEQ ID NO: 21) | QGGDYSSSSYGYG | (SEQ ID NO: 29) |
| H6.2b | QASQSVNN---LLA | (SEQ ID NO: 6) | GASNL----ES | (SEQ ID NO: 19) | QSGYYSP---GVT | (SEQ ID NO: 30) |
| G10.1 | QASESINN---YLA | (SEQ ID NO: 7) | GASNL----ES | (SEQ ID NO: 19) | QSGYYSG---GAT | (SEQ ID NO: 31) |
| D11.1c | LASENVYS---AVA | (SEQ ID NO: 8) | GASDI----ES | (SEQ ID NO: 22) | Q-GYSSYPPT | (SEQ ID NO: 32) |
| A5.2c | LASENVYG---AVA | (SEQ ID NO: 9) | GASNL----ES | (SEQ ID NO: 19) | Q-GYSSYP-T | (SEQ ID NO: 33) |
| F1d | QASQSVNN---LLA | (SEQ ID NO: 6) | GASNL----ES | (SEQ ID NO: 19) | AGYKSSSTD-GIA | (SEQ ID NO: 34) |
| F1e | QASQSISN---LLA | (SEQ ID NO: 10) | GASNL----ES | (SEQ ID NO: 19) | QSGYYSA---GHLT | (SEQ ID NO: 35) |
| E4.2 | LASENVAS---TVS | (SEQ ID NO: 11) | GASNL----ES | (SEQ ID NO: 19) | LGGFGYST-GLT | (SEQ ID NO: 36) |
| E2c | TLSTGYSVGEYPVV | (SEQ ID NO: 12) | HTDDIKHQGS | (SEQ ID NO: 23) | AIAHGTESSFHVV | (SEQ ID NO: 37) |
| A9c | TLSTGYSVGEYPVV | (SEQ ID NO: 12) | HTDDIKHQGS | (SEQ ID NO: 23) | AIAHGTESSFHVV | (SEQ ID NO: 37) |
| E11e | TLRTGYSVGEYPLV | (SEQ ID NO: 13) | HTDDIKHQGS | (SEQ ID NO: 23) | ATGHGSGSSAGVV | (SEQ ID NO: 38) |
| A1.1 | LASEDIYS---GLS | (SEQ ID NO: 14) | GASNL----ES | (SEQ ID NO: 19) | LGGYPYSST-GTA | (SEQ ID NO: 39) |
| F5.2 | QASQSVSN---LLA | (SEQ ID NO: 15) | GASNL----ES | (SEQ ID NO: 19) | QSGWYSA---GALT | (SEQ ID NO: 40) |
| F10b | QASQSVNN---LLA | (SEQ ID NO: 6) | RASTL----AS | (SEQ ID NO: 20) | QSGYYRA---GDLT | (SEQ ID NO: 41) |
| F7a | QASQSVSN---LLA | (SEQ ID NO: 15) | GASNL----ES | (SEQ ID NO: 19) | QSGYYSA---GLT | (SEQ ID NO: 27) |
| F6b | QASQSVSN---LLA | (SEQ ID NO: 15) | GASNL----ES | (SEQ ID NO: 19) | QSGYYSA---GLT | (SEQ ID NO: 27) |
| C12b | QASQSVSN---LLA | (SEQ ID NO: 15) | GASNL----ES | (SEQ ID NO: 19) | QSGYYSA---GALT | (SEQ ID NO: 42) |
| D2.1b | QASQSVNN---LLA | (SEQ ID NO: 6) | GASNL----ES | (SEQ ID NO: 19) | QSGYYSA---GLT | (SEQ ID NO: 27) |
| D1.1 | QASEDIES---YLA | (SEQ ID NO: 16) | GASNL----ES | (SEQ ID NO: 19) | QSNAWSV---GMT | (SEQ ID NO: 43) |
| D2.2a | QSSQSIAGA-YLS | (SEQ ID NO: 17) | LASKL----AS | (SEQ ID NO: 24) | AAQYSGN---IYT | (SEQ ID NO: 44) |
| D2.2b | LASENVYG---AVA | (SEQ ID NO: 9) | GASNL----ES | (SEQ ID NO: 19) | Q-GYSSYP-T | (SEQ ID NO: 33) |

*FIG. 9B*

| CLONE | HC-CDR1 | | HC-CDR2 | | HC-CDR3 | |
|---|---|---|---|---|---|---|
| A2c | NYAMT | (SEQ ID NO: 45) | IISSNGGA--DYASWAK | (SEQ ID NO: 64) | DDEGYDDYGDYMGYFTL | (SEQ ID NO: 84) |
| G12.1c | SYGLS | (SEQ ID NO: 46) | YFDPVFGNI--YYATWVD | (SEQ ID NO: 65) | DRIYVSSVG---YAFNL | (SEQ ID NO: 85) |
| B4.2a | TYGVS | (SEQ ID NO: 47) | YNDPIFGNI--YYATWVN | (SEQ ID NO: 66) | DRAYASSSG---YXXXX | (SEQ ID NO: 86) |
| E1c | SNAMG | (SEQ ID NO: 48) | IISSSGGT--YYASWAK | (SEQ ID NO: 67) | DWIAAGKS----YGLDL | (SEQ ID NO: 87) |
| F2d | TNAMG | (SEQ ID NO: 49) | IISSSGST--YYASWAK | (SEQ ID NO: 68) | DWIAAGKS----YGLDL | (SEQ ID NO: 87) |
| E5e | SSDWIC | (SEQ ID NO: 50) | CIYTGSSSSTWVASWAK | (SEQ ID NO: 69) | RYTGDNG-------NL | (SEQ ID NO: 88) |
| H6.2b | SDVIS | (SEQ ID NO: 51) | YIYTGDGST--DYASWVN | (SEQ ID NO: 70) | DAAYAGYGW---IFNL | (SEQ ID NO: 89) |
| G10.1 | SDVIS | (SEQ ID NO: 51) | YIYTGDGST--DYASWVN | (SEQ ID NO: 70) | DAAYAGYGW---IFNL | (SEQ ID NO: 89) |
| D11.1c | TYAMG | (SEQ ID NO: 52) | SIYASRSP--YYASWAK | (SEQ ID NO: 71) | GDAGSIP------YFKL | (SEQ ID NO: 90) |
| A5.2c | TYAMG | (SEQ ID NO: 52) | SIYASRSP--YYASWAK | (SEQ ID NO: 71) | GDAGSIP------YFKL | (SEQ ID NO: 90) |
| F1d | SNAMT | (SEQ ID NO: 53) | TIIYGDNT--YYASWAK | (SEQ ID NO: 72) | GNV----------FSDL | (SEQ ID NO: 91) |
| F1e | DFAMS | (SEQ ID NO: 54) | VVYAGTRGDTYYANWAK | (SEQ ID NO: 73) | GLT----------YYPL | (SEQ ID NO: 92) |
| E4.2 | DFAMS | (SEQ ID NO: 54) | VVYAGTRGDTYYANWAK | (SEQ ID NO: 73) | GLT----------YYPL | (SEQ ID NO: 92) |
| E2c | SYGMN | (SEQ ID NO: 55) | YIDPDYGST--YYASWVN | (SEQ ID NO: 74) | GAYSGYPS-----YFNL | (SEQ ID NO: 93) |
| A9c | SYGMN | (SEQ ID NO: 55) | YIDPDYGST--YYASWVN | (SEQ ID NO: 74) | GAYSGYPS-----YFNL | (SEQ ID NO: 93) |
| E11e | SNAMS | (SEQ ID NO: 56) | ITYPSGNV--YYASWAK | (SEQ ID NO: 75) | G------------FFNL | (SEQ ID NO: 94) |
| A1.1 | TNAIS | (SEQ ID NO: 57) | YSSYGNNA--HYTNWAK | (SEQ ID NO: 76) | GNA-----------YSDL | (SEQ ID NO: 95) |
| F5.2 | SNAMS | (SEQ ID NO: 56) | IIIGSGTT--YYANWAK | (SEQ ID NO: 77) | DQPIIYGAYGDYGLATGTRLDL | (SEQ ID NO: 96) |
| F10b | SYYMS | (SEQ ID NO: 58) | IISSSGTS--YYATWAK | (SEQ ID NO: 78) | DQPIIDAAYGDYGIATGTRLDL | (SEQ ID NO: 97) |
| F7a | SYTMS | (SEQ ID NO: 59) | IISSSGSA--YYATWAK | (SEQ ID NO: 79) | DQPIITTDYGGYGIATGTRLDL | (SEQ ID NO: 98) |
| F6b | SNAIS | (SEQ ID NO: 60) | IIVGSGTT--YYADWAK | (SEQ ID NO: 80) | DQPITYAGYGY--ATGTRLDL | (SEQ ID NO: 99) |
| C12b | SNAIS | (SEQ ID NO: 60) | IIVGSGTT--YYADWAK | (SEQ ID NO: 80) | DQPITYAGYGY--ATGTRLDL | (SEQ ID NO: 99) |
| D2.1b | TNAMS | (SEQ ID NO: 61) | TITYGTNA--YYASWAK | (SEQ ID NO: 81) | GNT-----------YSDL | (SEQ ID NO: 100) |
| D1.1 | SNAMS | (SEQ ID NO: 56) | TITYGTNA--YYASWAK | (SEQ ID NO: 81) | GNT-----------YSDL | (SEQ ID NO: 100) |
| D2.2a | SSYWIC | (SEQ ID NO: 62) | CIYTGSNGSTYYASWAK | (SEQ ID NO: 82) | AYIYYGGYG----FFDL | (SEQ ID NO: 101) |
| D2.2b | NYGVN | (SEQ ID NO: 63) | YIDPVFGST--YYASWVN | (SEQ ID NO: 83) | EASFYY--------GMDL | (SEQ ID NO: 102) |

CLONE: designation of representative clone for sequence; LC: Ig light chain; HC: Ig heavy chain;
CDR: complementarity determining region

*FIG. 9B (Cont.)*

Table 1(cont'd). Expression Pattern of CLL Specific Rabbit scFv Antibodies

| CLONE | CLL | B | RL | Ramos | TF-1 | Ag | Linker |
|---|---|---|---|---|---|---|---|
| A2c | + | + | ++ | + | - |  | S |
| G12.1c | + | + | + | + | - | CD19 | L |
| B4.2a | + | nd | + | + | - |  | L |
| E1c | ++ | + | - | - | - | CD23 | S |
| F2d | ++ | + | - | - | - |  | S |
| E5e | ± | nd | - | - | - |  | S |
| H6.2b | ++ | ++ | - | - | - |  | S |
| G10.1 | + | + | - | - | - |  | S |
| D11.1c | ++ | + | - | - | - | CD23 | S |
| A5.2c | ++ | + | - | - | - |  | S |
| F1d | + | ± | - | - | - |  | S |
| F1e | ++ | nd | - | - | - |  | S |
| E4.2 | + | + | - | - | - |  | S |
| E2c | + | ± | - | - | - |  | S |
| A9c | ++ | + | - | - | - |  | S |
| E11e | ++ | + | - | - | - |  | S |
| A1.1 | + | + | nd | nd | nd |  | L |
| F5.2 | + | nd | + | + | - |  | L |
| F10b | nd | nd | nd | nd | nd |  | L |
| F7a | nd | nd | nd | nd | nd |  | L |
| F6b | nd | nd | nd | nd | nd |  | L |
| C12b | nd | nd | nd | nd | nd |  | L |
| D2.1b | nd | nd | nd | nd | nd |  | S |
| D1.1 | + | + | nd | nd | nd |  | L |
| D2.2a | nd | nd | nd | nd | nd |  | L |
| D2.2b | nd | nd | nd | nd | nd |  | S |

CLONE: designation of representative clone for sequence
Expression pattern: binding of scFv antibodies to primary human cells and cell lines as determined by whole cell ELISA assay
CLL: chronic lymphocytic leukemias (primary tumors and CLL-AAT cell line)
B: normal, primary human B lymphocytes
RL: non-Hodgkin's lymphoma cell line
Ramos: Burkitt's lymphoma cell line
TF-1: human erythroleukemia cell line
Ag: antigen recognized by scFv antibody (determined by immunoprecipitation and mass spectrometry)
Linker: type of linker sequence between VL and VH regions. S, short linker; L, long linker

*FIG. 9C*

Table 2. Mean fluorescent intensities of B-CLL cells and normal PBMC labeled with scFv antibodies Antibody and CLL/PBMC Ratio:

| Donor | scFv-2 | ratio | scFv-3 | ratio | scFv-6 | ratio | scFv-9 | ratio |
|---|---|---|---|---|---|---|---|---|
| CLL(ML)<br>PBMC-1 | 590<br>715 | 0.83 | 398<br>181 | 2.2 | 284<br>137 | 2.1 | 511<br>80 | 6.4 |
| CLL(JR)<br>PBMC-2 | 311<br>368 | 0.85 | 207<br>87 | 2.4 | nd<br>nd | nd | 117<br>67 | 1.7 |
| CLL(HTS)<br>PBMC-3 | 219<br>317 | 0.69 | 173<br>106 | 1.6 | nd<br>nd | nd | 176<br>49 | 3.6 |
| CLL(RE)<br>PBMC-4 | 305<br>513 | 0.59 | 360<br>121 | 3 | nd<br>nd | nd | 142<br>81 | 1.7 |
| CLL(GB)<br>PBMC-5 | 262<br>563 | 0.47 | 387<br>212 | 1.8 | nd<br>nd | nd | 163<br>106 | 1.5 |

Primary PBMC from five patients diagnosed with CLL and five normal donors were analyzed by flow cytometry. The geometric mean fluorescent intensities were determined for cells stained with four different scFv antibodies. For scFvs that bind to antigens overexpressed on CLL cells, the CLL/PBMC ratio of fluorescent intensities is >1.0

FIG. 10

Comparison of scFv-9 antigen and CD38 expression on CLL cells.

| Patient ID | %CD19+ | %CD38+ | %scFv-9+ | ScFv-9 Level | CD38 | ScFv-9 |
|---|---|---|---|---|---|---|
| ML | 80 | 40 | 98 | 266 | Hi | Hi |
| IB | 86 | 87 | 96 | 366 | Hi | Hi |
| BH | 76 | 56 | 86 | 284 | Hi | Hi |
| JG | 82 | 92 | 97 | 125 | Hi | Lo |
| RE | 87 | 97 | 100 | 125 | Hi | Lo |
| EM | 91 | 8 | 95 | 268 | Lo | Hi |
| HS | 76 | 11 | 94 | 268 | Lo | Hi |
| MP | 40 | 6 | 95 | 280 | Lo | Hi |
| JR | 81 | 12 | 92 | 124 | Lo | Lo |
| GB | 65 | 20 | 98 | 187 | Lo | Lo |

*FIG. 11*

Identification of scFv Antigens

- Cell-surface biotinylation (CLL-ATT cells)
- Membrane isolation (nitrogen cavitation, differential centrifugation)
- Immunoprecipitation with scFv-HA coupled to Anti-HA beads
- SDS-PAGE
- Detection by Coomassie-stain or AP-streptavidin Western blot
- MALDI-MS or LC-MS/MS to obtain peptide mass spectra/peptide sequences

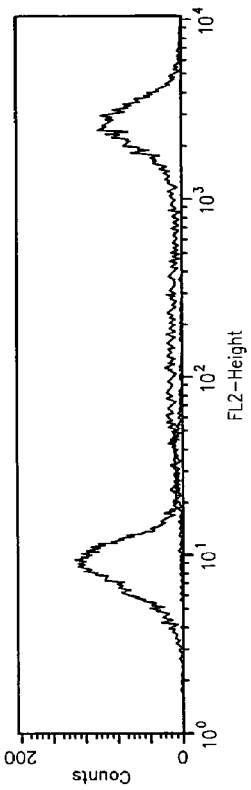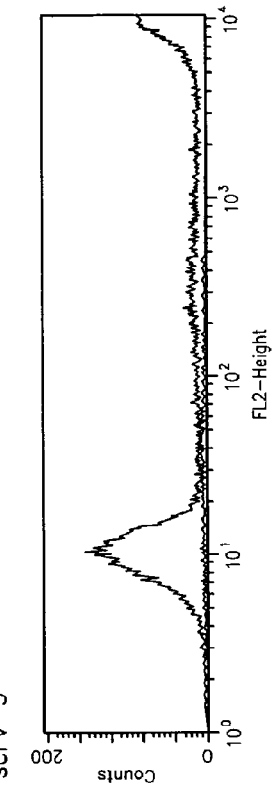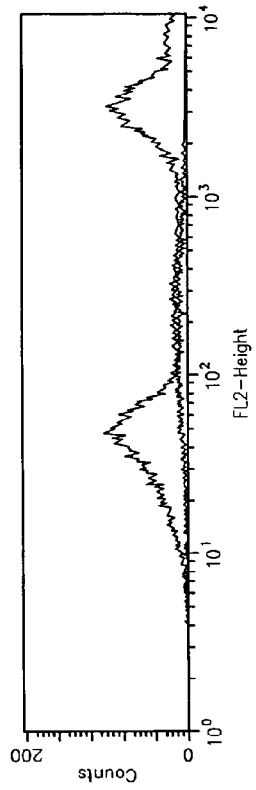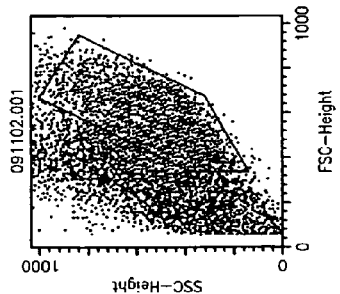
FIG. 13

Group 6: 10 mice, $4 \times 10^6$ RAJI cells each
Group 7: 10 mice, $4 \times 10^6$ RAJI + $1 \times 10^6$ PBL donor 3
Group 8: 10 mice, $4 \times 10^6$ RAJI + $5 \times 10^6$ PBL donor 3
Group 9: 9 mice, $4 \times 10^6$ RAJI + $1 \times 10^7$ PBL donor 3
Group 10: 10 mice, $4 \times 10^6$ RAJI + $1 \times 10^6$ PBL donor 4
Group 11: 14 mice, $4 \times 10^6$ RAJI + $1 \times 10^7$ PBL donor 4

| | Statistics comparing | p values are given group2-4 to 1 | | | | group5 | comparing group7-11 to 6 | | | | | |
|---|---|---|---|---|---|---|---|---|---|---|---|---|
| | | group1 | group2 | group3 | group4 | | group7 | group8 | group9 | group10 | group11 | |
| d22 | t-test | ns | ns | ns | ns | <0.0022 | ns | ns | ns | ns | ns | |
| | Welch | ns | ns | ns | ns | <0.0031 | | | | | | |
| | Wilcox | ns | ns | ns | ns | <0.0093 | | | | | | |
| d25 | t-test | ns | ns | ns | ns | <0.0766 | <0.468 | <0.865 | <0.837 | <0.055 | <0.927 | |
| | Welch | ns | ns | ns | ns | <0.0788 | | | | | | |
| | Wilcox | ns | ns | ns | ns | <0.014 | | | | | | |
| d27 | t-test | ns | ns | ns | ns | <0.038 | <0.416 | <0.521 | <0.83 | <0.053 | <0.588 | |
| | Welch | ns | ns | ns | ns | <0.036 | | | | | | |
| | Wilcox | ns | ns | ns | ns | <0.014 | | | | | | |
| d29 | t-test | ns | ns | ns | ns | <0.0121 | <0.87 | <0.564 | <0.64 | <0.0712 | <0.936 | |
| | Welch | ns | ns | ns | ns | <0.017 | | | | | | |
| | Wilcox | ns | ns | ns | ns | <0.0093 | | | | | | |
| d32 | t-test | ns | ns | ns | ns | <0.0197 | <0.824 | <0.123 | <0.296 | <0.31 | <0.89 | |
| | Welch | ns | ns | ns | ns | <0.025 | | | | | | |
| | Wilcox | ns | ns | ns | ns | <0.0059 | | | | | | |
| d34 | t-test | ns | ns | ns | ns | <0.03 | <0.45 | <0.0727 | <0.057 | <0.296 | <0.427 | |
| | Welch | ns | ns | ns | ns | <0.035 | | <0.059 | <0.0546 | | | |
| | Wilcox | ns | ns | ns | ns | <0.0059 | | <0.1 | <0.06 | | | |
| d36 | t-test | ns | ns | ns | ns | <0.0277 | <0.2 | <0.0122 | <0.0082 | <0.1775 | <0.145 | |
| | Welch | ns | ns | ns | ns | <0.0328 | | <0.0154 | <0.0085 | | | |
| | Wilcox | ns | ns | ns | ns | <0.0022 | | <0.0288 | <0.0076 | | | |
| d39 | t-test | ns | ns | ns | ns | <0.0607 | <0.41 | <0.0207 | <0.0095 | <0.274 | <0.26 | |
| | Welch | ns | ns | ns | ns | <0.064 | | <0.025 | <0.0106 | | | |
| | Wilcox | ns | ns | ns | ns | <0.0289 | | <0.0345 | <0.004 | | | |
| d41 | t-test | ns | ns | ns | ns | <0.0309 | <0.575 | <0.0144 | <0.0073 | <0.357 | <0.245 | |
| | Welch | ns | ns | ns | ns | <0.0502 | | <0.0178 | <0.0083 | | | |
| | Wilcox | ns | ns | ns | ns | <0.0023 | | <0.035 | <0.0056 | | | |
| d43 | t-test | ns | ns | ns | ns | <0.0257 | <0.88 | <0.0076 | <0.0021 | <0.327 | <0.196 | |
| | Welch | ns | ns | ns | ns | <0.0438 | | <0.0099 | <0.0025 | | | |
| | Wilcox | ns | ns | ns | ns | <0.004 | | <0.0172 | <0.0019 | | | |
| d45 | t-test | ns | ns | ns | ns | | <0.653 | <0.0025 | <0.007 | <0.48 | <0.059 | |
| | Welch | ns | ns | ns | ns | | | <0.0032 | <0.008 | | <0.0566 | |
| | Wilcox | ns | ns | ns | ns | | | <0.0041 | <0.0012 | | <0.0622 | |
| d48 | t-test | | | | | | <0.4429 | <0.0055 | <0.0069 | <0.3459 | <0.0359 | |
| | Welch | | | | | | <0.445 | <0.0076 | <0.0073 | <0.341 | <0.05 | |
| | Wilcox | | | | | | <0.315 | <0.0133 | <0.004 | <0.2775 | <0.053 | |
| d50 | t-test | | | | | | <0.4 | <0.0103 | <0.008 | <0.35 | <0.0915 | |
| | Welch | | | | | | | <0.006 | <0.0085 | | | |
| | Wilcox | | | | | | | <0.0106 | <0.0142 | | <0.082 | | ns=not significant
significant groups are shown in red

*FIG. 18*

ELISA results of representative IgG1 kappa clones after round 3 panning on CD200-Fc captured on goat anti-mouse IgG Fc antibody ELISA results of representative IgG2a kappa clones after round 3 panning on CD200-Fc captured on goat anti-mouse IgG Fc antibody ELISA results of representative IgG1 kappa clones after round 3 panning on CD200-Fc directly coated on microtiter wells.

ELISA results of representative IgG2a kappa clones after round 3 panning on CD200-Fc directly coated on microtiter wells.

Flow cytometry results of representative IgG1 clones selected on CD200-Fc captured with goat anti-mouse IgG Fc Flow cytometry results of representative IgG2a clones selected on CD200-Fc captured with goat anti-mouse IgG Fc Flow cytometry results of representative IgG1 clones selected on directly coated CD200-Fc Flow cytometry results of representative IgG2a clones selected on directly coated CD200-Fc Deduced amino acid sequence of heavy chain complementarity regions of CD200-specific clones

| Seq# | HCDR1 | HCDR2 | HCDR3 | Fab | geo mean* |
|---|---|---|---|---|---|
| A1 | GFNIKDYYMH (SEQ ID NO:111) | WIDPENGDTKYAPKFQG (SEQ ID NO:117) | KNYVSNYNYFDV (SEQ ID NO:131) | cG1R3A2 | 291.8 |
| B1 | GFNIKDYYMH (SEQ ID NO:111) | WIDPENGDTKYAPKFQG (SEQ ID NO:117) | KNYVSNYNYFDV (SEQ ID NO:131) | cG1R3A3 | 486.15 |
| C1 | GFNIKDYYMH (SEQ ID NO:111) | WID?ENGDTKYAPKFQG (SEQ ID NO:117) | KNYVSNYNYFDV (SEQ ID NO:131) | cG1R3A4 | 340.61 |
| B2 | GFNIKDYYMH (SEQ ID NO:111) | WIDPENGDTKYAPKFQG (SEQ ID NO:118) | KNYVSNYNYFDV (SEQ ID NO:131) | cG1R3B3 | 131.84 |
| E2 | GFNIKDYYMH (SEQ ID NO:111) | WIDPENGDTKYAPKFQG (SEQ ID NO:118) | KNYVSNYNYFDV (SEQ ID NO:131) | cG1R3B6 | 576.09 |
| G2 | GFNIKDYYMH (SEQ ID NO:111) | WIDPENGDTKYAPKFQG (SEQ ID NO:118) | KNYVSNYNYFDV (SEQ ID NO:131) | cG1R3B9 | 407.58 |
| A3 | GFNIKDYYMH (SEQ ID NO:111) | WIDPENGDTKYAPKFQG (SEQ ID NO:118) | KNYVSNYNYFDV (SEQ ID NO:131) | cG1R3B12 | 363.52 |
| C3 | DFNIKDYY?H (SEQ ID NO:112) | WIDPE?DDTKYAPKFQG (SEQ ID NO:119) | KNYVSNYNYFDV (SEQ ID NO:131) | cG1R3C2 | 271.55 |
| D3 | GFNIKDYY?H (SEQ ID NO:112) | WIDPENGDTKYAPKFQG (SEQ ID NO:118) | KNYVSNYNYFDV (SEQ ID NO:131) | cG1R3C3 | 452.53 |
| F3 | GLNIKDYYMH (SEQ ID NO:113) | WIDPENGNTKYAPKFQG (SEQ ID NO:120) | KNYVSNYNYFDV (SEQ ID NO:131) | cG1R3C6 | 505.75 |
| A5 | GFNIKDYYMH (SEQ ID NO:111) | WIDPENGDTKYAPKFQG (SEQ ID NO:118) | KNYVSNYNYFDV (SEQ ID NO:131) | cG2aR3A9 | 1684.92 |
| A6 | GFNIKDYYMH (SEQ ID NO:111) | WIDPENGDTKYAPKFRG (SEQ ID NO:121) | KNYVSNYNYFDV (SEQ ID NO:131) | cG2aR3B5 | 1819.42 |
| B7 | GFNIKDYYIH (SEQ ID NO:114) | WIDPENGDTKYAPKFQG (SEQ ID NO:118) | KNYVSNYNYFDV (SEQ ID NO:131) | dG1R3A2 | 1325 |
| D7 | GFNIKDYYIH (SEQ ID NO:114) | WIDPENGDTKYAPKFQG (SEQ ID NO:122) | KNYVSDYNYFDV (SEQ ID NO:132) | dG1R3A4 | 1245 |
| E7 | GFNIKDYYMH (SEQ ID NO:111) | WIDPDNGDTKYAPKFQG (SEQ ID NO:118) | KNYVSNYNYFDV (SEQ ID NO:131) | dG1R3A5 | 1969 |
| G7 | GFNIKDYYLH (SEQ ID NO:115) | WIDPENGDTKYAPKFQG (SEQ ID NO:118) | KNYVSNYNYFDV (SEQ ID NO:131) | dG1R3A7 | 1486 |
| H7 | GFNIKDYYMH (SEQ ID NO:111) | WIDPENGDTKYAPKFQG (SEQ ID NO:118) | KNYVSNYNYFDV (SEQ ID NO:131) | dG1R3A8 | 1852 |
| C8 | GFNIKDYYMH (SEQ ID NO:111) | WIDPENGDTKYAPKFQG (SEQ ID NO:118) | KNYVSNYNYFDV (SEQ ID NO:131) | dG1R3A12 | 981.26 |
| D8 | GFNIKDYYMH (SEQ ID NO:111) | WIDPENGDTKYAPKFQG (SEQ ID NO:118) | KNYVSNYNYFDV (SEQ ID NO:131) | dG1R3B2 | 488.59 |
| E8 | GFNIKDYYMH (SEQ ID NO:111) | WIDEENGDTKYAPKFQG (SEQ ID NO:118) | KNYVSNYNYFDV (SEQ ID NO:131) | dG1R3B3 | 790.06 |
| D9 | GFNIKDYYMH (SEQ ID NO:111) | WIDPENGDTKYAPKFQG (SEQ ID NO:118) | KNYVSNYNYFDV (SEQ ID NO:131) | dG1R3B11 | 1328 |
| E9 | GFNIKDYYMH (SEQ ID NO:111) | WIDPENGDTKYAPKFQG (SEQ ID NO:118) | KNYVSNYNYFDV (SEQ ID NO:131) | dG1R3B12 | 1333 |
| F9 | GFNIKDYYMH (SEQ ID NO:111) | WIDPENGDTKYAPKFQG (SEQ ID NO:118) | KNYVSNYNYFDV (SEQ ID NO:131) | dG1R3C1 | 1782.8 |
| F1 | GFNIKDYYMH (SEQ ID NO:111) | WIDPENGDTKYAPKFQG (SEQ ID NO:118) | KNYVSNYNYFDV (SEQ ID NO:131) | cG1R3A9 | 505.72 |
| A4 | GYTFTSYVMH (SEQ ID NO:116) | YINPYNDVTKNNEKFRG (SEQ ID NO:123) | KRGGYDGAWFAY (SEQ ID NO:134) | cG2aR3A1 | 2146.54 |
| E4 | GYTFTSYVMH (SEQ ID NO:116) | YINPYNDVTKNNEKFRG (SEQ ID NO:123) | KRGGYDGAWFAY (SEQ ID NO:134) | cG2aR3A5 | 586.74 |
| G4 | GYTFTSYVMH (SEQ ID NO:116) | YINPYNDVTKNNEKFRG (SEQ ID NO:123) | KRGGYDGAWFAY (SEQ ID NO:134) | cG2aR3A7 | 1563.74 |
| C12 | GYTFTSYVMH (SEQ ID NO:116) | YINPYNDVTKNNEKFRG (SEQ ID NO:123) | KRGGYDGAWFAY (SEQ ID NO:134) | dG2aR3B9 | 1942.44 |
| D11 | GYTFTSYVMH (SEQ ID NO:116) | YINPYNDVTKNNEKFRG (SEQ ID NO:123) | KRGGYDGAWFAY (SEQ ID NO:134) | dG2aR3B1 | 1668.3 |
| D12 | GYTFTSYVMH (SEQ ID NO:116) | YINPYNDITNYNEKFKG (SEQ ID NO:124) | KRGGYDGAWFAY (SEQ ID NO:134) | dG2aR3B10 | 2244.57 |
| B4 | GYTFTSYVMH (SEQ ID NO:116) | YINPYNDITNYNEKFKG (SEQ ID NO:124) | KRGGYDGAWFAY (SEQ ID NO:134) | cG2aR3A2 | 1281.05 |
| B12 | GYTFTSYVMH (SEQ ID NO:116) | YINPYNDITNYNEKPKG (SEQ ID NO:124) | KRGGYDGAWFAY (SEQ ID NO:134) | cG2aR3B8 | 1351.49 |
| E6 | GYTFTSYVMH (SEQ ID NO:116) | YINPYNDGSKYNEKFKG (SEQ ID NO:125) | KRGGYDGAWFAY (SEQ ID NO:134) | cG2aR3B9 | 2004.46 |
| D4 | GYTFTSYVMH (SEQ ID NO:116) | YINPYNDGTKYNEKFKG (SEQ ID NO:126) | KRGGYDGAWFAY (SEQ ID NO:134) | cG2aR3A4 | 1315.64 |
| C11 | GYTFTSYVMH (SEQ ID NO:116) | YINPYNDGTKYNEKFKG (SEQ ID NO:126) | KRGGYDGAWFAY (SEQ ID NO:134) | dG2aR3A1 | 2043.86 |
| A10 | GYTFTSYVMH (SEQ ID NO:116) | YINPYNDGTRYNEKFKG (SEQ ID NO:127) | KRGGYDGAWFAY (SEQ ID NO:134) | dG2aR3A1 | 2179.3 |
| B10 | GYTFTSYVMH (SEQ ID NO:116) | YINPYNDGTRYNEKFKG (SEQ ID NO:127) | KRGGYDGAWFAY (SEQ ID NO:134) | dG2aR3B5 | 1625.73 |
| A12 | GYTFTSYVMH (SEQ ID NO:116) | YINPYNDVTRYNEKFKG (SEQ ID NO:127) | KRGGYDGAWFAY (SEQ ID NO:134) | dG2aR3A7 | 1814.85 |
| F10 | GYTFTSYVMH (SEQ ID NO:116) | YINPYNDITNYNEKPKG (SEQ ID NO:128) | KRGGYDGAWFAY (SEQ ID NO:134) | dG2aR3B2 | 2272.54 |
| E11 | GYTFTSYVMH (SEQ ID NO:116) | YINPYNDGTNYNEKFKG (SEQ ID NO:129) | KRGGYDGAWFAY (SEQ ID NO:134) | dG2aR3A9 | 1526.7 |
| H10 | GYTFTSYVMH (SEQ ID NO:116) | YINPYNDGTNYNEKFKG (SEQ ID NO:129) | KRGGYDGAWFAY (SEQ ID NO:134) | dG2aR3A9 | 1882.28 |
| F11 | GYTFTSYVMH (SEQ ID NO:116) | YINPYNDVTKYNEKFRG (SEQ ID NO:130) | KRGGYDGAWFAY (SEQ ID NO:134) | dG2aR3B3 | 1882.28 |

*Geometric mean of flow cytometry signal.

FIG. 21A

Deduced amino acid sequence of heavy chain complementarity regions of CD200-specific clones

| Seq# | HCDR1 | HCDR2 | HCDR3 | Fab | geo mean* |
|---|---|---|---|---|---|
| D2 | GFNIKDHYMH (SEQ ID NO:35) | WIPENGDTEYAPKFQG (SEQ ID NO:154) | FNGYYAMDY (SEQ ID NO:178) | cG1R3B5 | 299.95 |
| A7 | GFNIKDHYMH (SEQ ID NO:35) | WIPENGDTEYAPKFQG (SEQ ID NO:154) | FNGYYAMDY (SEQ ID NO:178) | dG1R3A1 | 2075 |
| C7 | AFNIKDHYMH (SEQ ID NO:36) | WIPESGDTEYAPKFQG (SEQ ID NO:155) | FNGYLALDY (SEQ ID NO:179) | dG1R3A3 | 624.84 |
| A8 | AFNIKDHYMH (SEQ ID NO:36) | WIPESGDTEYAPKFQG (SEQ ID NO:155) | FNGYQALD? (SEQ ID NO:180) | dG1R3A9 | 1490 |
| B5 | AFNIKDHYMH (SEQ ID NO:36) | WIPESGDTEYAPKFQG (SEQ ID NO:155) | FNGYQALDQ (SEQ ID NO:181) | cG2aR3A10 | 1386.23 |
| H3 | AFNIKDHYMH (SEQ ID NO:36) | WIPESGDTEYAPKFQG (SEQ ID NO:155) | FNGYLALDQ (SEQ ID NO:182) | cG1R3C8 | 399.21 |
| B8 | AFNIKDHYMH (SEQ ID NO:36) | WIPESGNTEYAPKFQG (SEQ ID NO:155) | FNGYQALDQ (SEQ ID NO:181) | dG1R3A11 | 929.93 |
| B6 | GFNLKDYYMH (SEQ ID NO:137) | WIPESGNTEYAPKFQG (SEQ ID NO:156) | RNEYYTMDY (SEQ ID NO:183) | cG1R3B6 | 1564.28 |
| E5 | GFNIKDYYMH (SEQ ID NO:111) | WIPENGNTEYAPKFQ? (SEQ ID NO:157) | RNEYYIMDY (SEQ ID NO:184) | cG2aR3B1 | 1751.43 |
| E12 | GFNIKDYYMH (SEQ ID NO:111) | WIPENGNTEYAPKFQG (SEQ ID NO:156) | RNEYYTMDY (SEQ ID NO:183) | dG2aR3B11 | 1462.43 |
| A11 | GFNLKDYYMH (SEQ ID NO:137) | WIDPENGNTEYAPKFQG (SEQ ID NO:158) | RNEYYMDY (SEQ ID NO:183) | cG2aR2A10 | 1668.3 |
| H8 | AFNIKDHYMH (SEQ ID NO:36) | WIDPESGDTEYAPKFQG (SEQ ID NO:159) | FNGYQALDQ (SEQ ID NO:181) | dG1R3B6 | 1513 |
| D1 | GYTFTDYWLH (SEQ ID NO:38) | TIDTSTGYTGYNQKFKG (SEQ ID NO:160) | GGDNYWFAY (SEQ ID NO:185) | cG1R3A6 | 448.43 |
| E1 | GFTFSAAWMD (SEQ ID NO:39) | EIRSKANNHATYYAESVKG (SEQ ID NO:161) | NGYDDGVPFDY (SEQ ID NO:186) | cG1R3A7 | 393.89 |
| G1 | GYTFTEYYMH (SEQ ID NO:40) | GVNPNNGGALYNQKFKG (SEQ ID NO:162) | RSNYRYDDAMDY (SEQ ID NO:187) | dG1R3A10 | 274.99 |
| A2 | GFTFSGFAMS (SEQ ID NO:41) | SISSGGTTYYLDSVKG (SEQ ID NO:163) | GNYYSGTSYDY (SEQ ID NO:188) | cG1R3B2 | 476.04 |
| G3 | GFTFSGFAMS (SEQ ID NO:41) | SISSGGTTYYLDSVKG (SEQ ID NO:163) | GNYYSGTSYDY (SEQ ID NO:188) | cG1R3C7 | 638.59 |
| F7 | GFTFSGFAMS (SEQ ID NO:41) | SISSGGTTYYLDSVKG (SEQ ID NO:163) | GNYYSGTSYDY (SEQ ID NO:188) | dG1R3A6 | 1665 |
| A9 | GFTFSGYAMS (SEQ ID NO:42) | SISSGGSAYYPDSVKG (SEQ ID NO:164) | GNYYSGTSYDY (SEQ ID NO:188) | dG1R3B7 | 1994 |
| B9 | GFTFSGFAMS (SEQ ID NO:41) | SISSGGTTYYLDSVKG (SEQ ID NO:163) | GNYYSGTSYDY (SEQ ID NO:188) | dG1R3B9 | 1569 |
| C9 | GFTFSGFAMS (SEQ ID NO:41) | SISSGGTTYYLDSVKG (SEQ ID NO:163) | GNYYSGTSYDY (SEQ ID NO:188) | dG1R3B10 | 1839 |
| G9 | GFTFSGFAMS (SEQ ID NO:41) | SISSGGTTYYLDSVKG (SEQ ID NO:163) | GNYYSGTSYDY (SEQ ID NO:188) | dG1R3C2 | 1586 |
| C2 | GFNIKDYIH (SEQ ID NO:114) | WIDPEIGATKVPKFQG (SEQ ID NO:165) | LYGNYDRYYAMDY (SEQ ID NO:189) | cG1R3B4 | 385.24 |
| G8 | GFNIKDYIH (SEQ ID NO:114) | WIDPEIGATKVPKFQG (SEQ ID NO:165) | LYGNYDRYYAMDY (SEQ ID NO:189) | dG1R3B5 | 1451 |
| F2 | GFTFSSHAMS (SEQ ID NO:143) | SISSGGGTYYPNSVKGR (SEQ ID NO:166) | RGDYYRYPYAMDY (SEQ ID NO:190) | cG1R3B7 | 415.38 |
| H2 | GFTFSSHAMS (SEQ ID NO:143) | SISSGGGTYYPNSVKGR (SEQ ID NO:166) | RGDYYRYPYAMDY (SEQ ID NO:190) | cG1R3B10 | 109.14 |
| E3 | GFTFSSHAMS (SEQ ID NO:143) | SISSGGGTYYPNSVKGR (SEQ ID NO:166) | RGDYYRYPYAMDY (SEQ ID NO:190) | cG1R3C4 | 589.64 |
| H4 | GYTFTETMH (SEQ ID NO:144) | GINPENNGGYSYNQKFKG (SEQ ID NO:167) | MITTGYHYAMDY (SEQ ID NO:191) | cG2aR3A8 | 682.7 |
| H5 | GYTFTETMH (SEQ ID NO:144) | GINPENTGGYSYNQKFKC (SEQ ID NO:168) | MITTGYHYAMDY (SEQ ID NO:191) | cG2aR3B4 | 711.01 |
| F6 | GYTFTETMH (SEQ ID NO:144) | GINPENTGGYSYNQKFKG (SEQ ID NO:168) | MITTGYHYAMDY (SEQ ID NO:191) | cG2aR3B10 | 737.93 |
| G6 | GYTFTETMH (SEQ ID NO:144) | GINPENNGGYSYNQKFKG (SEQ ID NO:167) | MITTGYHYAMDY (SEQ ID NO:191) | cG2aR3B12 | 278.53 |
| C10 | GYTFTEFTMH (SEQ ID NO:144) | GINPENNGGYSYNQKFKG (SEQ ID NO:168) | MITTGYHYAMDY (SEQ ID NO:191) | dG2aR3A4 | 814.16 |
| D10 | GYTFTEFTMH (SEQ ID NO:144) | GINPENTG?AYNQKFKG (SEQ ID NO:144) | MITTGYHYAMDY (SEQ ID NO:191) | dG2aR3A5 | 421.7 |
| G12 | GYTFTEFTMH (SEQ ID NO:144) | GINPENTGGYSNQKFKG (SEQ ID NO:168) | MITTGYHYAMDY (SEQ ID NO:191) | dG2aR3C1 | 1068.43 |
| H12 | GYTFTEFTMH (SEQ ID NO:144) | GINPENTGGYSNQKFKG (SEQ ID NO:168) | MITTGYHYAMDY (SEQ ID NO:191) | dG2aR3C3 | 1106.7 |
| C5 | GYIFTSFYIH (SEQ ID NO:145) | WISPGSLNTNYNEKFRG (SEQ ID NO:169) | KARGDSGAWFAY (SEQ ID NO:192) | dG2aR3A11 | 1311.44 |
| D5 | GYTFTSFYIH (SEQ ID NO:146) | WISPGSLNTNYNEKFRG (SEQ ID NO:169) | KARGDSGAWFAY (SEQ ID NO:192) | cG2aR3A12 | 887.54 |
| B11 | GYTFTSFYIH (SEQ ID NO:145) | WISPGSLNTNYNEKFRG (SEQ ID NO:169) | KARGDSGAWFAY (SEQ ID NO:192) | dG2aR3A11 | 1588.4 |
| F5 | GYTFDYWMH (SEQ ID NO:147) | AIDTFDSNFRYNQKFKG (SEQ ID NO:170) | GVDY (SEQ ID NO:193) | cG2aR3B2 | 1491.49 |
| G10 | GYTFDYWMH (SEQ ID NO:147) | AIDTFDSNFRYNQKFKG (SEQ ID NO:171) | GVDY (SEQ ID NO:193) | dG2aR3A8 | 1424.53 |
| H11 | GYTFDYWMH (SEQ ID NO:147) | AIDTFDSNFRYNQKFKG (SEQ ID NO:172) | GVDY (SEQ ID NO:193) | dG2aR3B5 | 1259.43 |
| G5 | GYTFTDNWIH (SEQ ID NO:148) | TIDASDRYISYNQKFRG (SEQ ID NO:173) | LEGSGYGFAY (SEQ ID NO:194) | cG2aR3B3 | 1289.19 |
| F8 | GYTFTDNWIH (SEQ ID NO:148) | TIDASDRYISYNQKFRG (SEQ ID NO:173) | LEGSGYGFAY (SEQ ID NO:194) | dG1R3B4 | 1340 |
| C6 | GYSFTDYIIL (SEQ ID NO:49) | HIDPYYGGSNYNLKFKG (SEQ ID NO:174) | SKRDYFDY (SEQ ID NO:195) | cG2aR3B7 | 1776.38 |
| H6 | GFNIKOSYIH (SEQ ID NO:150) | WIDPENGGTEYAPKFQG (SEQ ID NO:175) | CNFYGNPYFDY (SEQ ID NO:196) | cG2aR3C1 | 1833.02 |
| F12 | GFNIK?SYIH (SEQ ID NO:151) | WIDPENGGTEYAPKFQG (SEQ ID NO:175) | CNFYANPYFDY (SEQ ID NO:197) | dG2aR3B12 | 1350.25 |
| H9 | GYTFTSYIH (SEQ ID NO:152) | YINPSSGYTNYNQKFKD (SEQ ID NO:176) | RPMITAGAWFAY (SEQ ID NO:198) | dG1R3H8 | 2470 |
| E10 | GYTFTEYYMH (SEQ ID NO:153) | GINPNTGAYNYNQKFKG (SEQ ID NO:177) | ITTVVGYYYAMDY (SEQ ID NO:199) | dG2aR3A6 | 796.81 |

*Geometric mean of flow cytometry signal.

FIG. 21B

R9.4 is a chimeric antibody derived from a rabbit scFv9. 9H is an anti-FLJ32028 antibody and was included as a negative control.

Deduced amino acid sequences of selected CD200 Fabs for chimerization

Heavy chain

| Fab | FR1 | CDR1 | FR2 | CDR2 | |
|---|---|---|---|---|---|
| d1B10 | LEVKLVESGGGLVKPGGSLKLSCAAS | GFTFSGFAMS | WVRQTPEKRLEWVA | SISSGGTTYYLDSVKG | (SEQ ID NO: 200) |
| d1A5 | LEVQLQQSGAELVRSGASVKLSCTAS | GFNIKDYYMH | WVKQRPEQGLEWIG | WIDPENGDTKYAPKFQG | (SEQ ID NO: 201) |
| d1B5 | LEVQLQQPGAELVRSGASVKLSCKAS | GFNIKDYYIH | WVKQRPEQGLEWIG | WIDPEIGATKYVPKFQG | (SEQ ID NO: 202) |
| c2aB7 | LEVQLQQSGPELVKPGASLKMSCKAS | GYSFTDYIIL | WVKQNHGKSLEWIG | HIDPYYGSSNYNLKFKG | (SEQ ID NO: 203) |
| c1A10 | LEVQLQQSGPELVKPGASVKISCKTS | GYTFTEYTMH | WVKQSHGKSLEWIG | GVNPNNGGALYNQKFKG | (SEQ ID NO: 204) |
| c2aA10 | LEVQLQQSGAELVRSGASVKLSCTAS | AFNIKDHYMH | WVKQRPEQGLEWIG | WIDPESGDTEYAPKFQG | (SEQ ID NO: 205) |

| Fab | FR3 | CDR3 | FR4 | |
|---|---|---|---|---|
| d1B10 | RFTISRDIARNILYLQMSSLRSEDTAMYCAR | GNYYSGTSYDY | WGQGTTLTVSS | (SEQ ID NO: 200 - cont'd) |
| d1A5 | KATMTADTSSNTAYLQLSSLTSEDTAVYYCNA | KNYYVSNYNFFDV | WGAGTTVTVSS | (SEQ ID NO: 201 - cont'd) |
| d1B5 | KATMTTDTSSNTAYLQLSSLTSEDTAVYYCNA | LYGNYDRYYAMDY | WGQGTSVTVSS | (SEQ ID NO: 202 - cont'd) |
| c2aB7 | KATLTVDKSSSTAYMQLNSLTSEDSAVYYCGR | SKRDYFDY | WGQGTTLTVSS | (SEQ ID NO: 203 - cont'd) |
| c1A10 | KATLTVDKSSSTAYMELRSLASEDSAVYYCAR | RSNYRYDDAMDY | WGQGTSVTVSS | (SEQ ID NO: 204 - cont'd) |
| c2aA10 | KATMTADISSNTAYLQLNSLTSEDTAVYYCNA | FNGYQALDQ | WGQGTSVTVSS | (SEQ ID NO: 205 - cont'd) |

Light chains

| Fab | FR1 | CDR1 | FR2 | CDR2 | |
|---|---|---|---|---|---|
| d1B10 | SRDIVLTQSPASLAVSLGQRATISC | RASESVDSYGNSFMH | WYQQKPGQPPKLLIY | RASNLES | (SEQ ID NO: 206) |
| d1A5 | SREIVLTQSPATMSASPGEKVTMTC | SASSSVRYMY | WYQQKSSTSPKLWIY | DTSKLAS | (SEQ ID NO: 207) |
| d1B5 | SRDIVMTQSQKFMSTSVGDRVSITC | KASQNVRTAVA | WYQQKPGQSPKALIY | LASNRHT | (SEQ ID NO: 208) |
| c2aB7 | SRDIQMTQSPSSMYASLGERVTITC | KASQDINSYLS | WFQQKPGKSPKTLIY | RANRLVD | (SEQ ID NO: 209) |
| c1A10 | SRDVVMTQTPLTLSVTIGQPASISC | KSSQSLLDIDEKTYLN | WFLQRPGQSPKRLIY | LVSKLDS | (SEQ ID NO: 210) |
| c2aA10 | SREIVLTQSPAIMSASLGERVTMTC | TASSSVSSSYLH | WYQQKPGSSPKLWIY | STSNLAS | (SEQ ID NO: 211) |

| Fab | FR3 | CDR3 | FR4 | |
|---|---|---|---|---|
| d1B10 | GIPARFSGSGSRTDFTLTINPVEADDVATYYC | QQSNEDPRT | FGGGTKLEIKR | (SEQ ID NO: 206 - cont'd) |
| d1A5 | GVGRFSGSGSGNSYSLTISSMEAEDVATYYC | FQGSGYPLT | FGSGTKLEIKR | (SEQ ID NO: 207 - cont'd) |
| d1B5 | GVPDRFTGSGSGTDFTLTISNVQSEDLADYFC | LQHWNYPLT | FGAGTKLEIKR | (SEQ ID NO: 208 - cont'd) |
| c2aB7 | GVPSRFSGSGSGQDYSLTISSLEYEDMGIYYC | LQYDEFPYT | FGGGTKLEIKR | (SEQ ID NO: 209 - cont'd) |
| c1A10 | GVPDRFTGSGSGTDFTLKISRVEAEDLGVYYC | WQGTHFPQT | FGGGTKLEIKR | (SEQ ID NO: 210 - cont'd) |
| c2aA10 | GVPARFSGSGSGTSYSLTISSMEAEDAATYYC | RQYHRSPPIFT | FGSGTKLEIKR | (SEQ ID NO: 211 - cont'd) |

FIG. 23

ELISA results of chimeric IgG obtained from the culture supernatant of a small-scale transient transfection.

SEQUENCE LISTING

```
<160> NUMBER OF SEQ ID NOS: 211

<210> SEQ ID NO 1
<211> LENGTH: 14
<212> TYPE: PRT
<213> ORGANISM: rabbit

<400> SEQUENCE: 1

Thr Leu Ser Thr Gly Tyr Ser Val Gly Ser Tyr Val Ile Ala
1               5                   10
```

```
<210> SEQ ID NO 2
<211> LENGTH: 11
<212> TYPE: PRT
<213> ORGANISM: rabbit

<400> SEQUENCE: 2

Gln Ala Ser Glu Ser Ile Arg Asn Tyr Leu Ala
1               5                   10

<210> SEQ ID NO 3
<211> LENGTH: 11
<212> TYPE: PRT
<213> ORGANISM: rabbit

<400> SEQUENCE: 3

Gln Ala Ser Glu Ser Ile Ser Asn Trp Leu Ala
1               5                   10

<210> SEQ ID NO 4
<211> LENGTH: 11
<212> TYPE: PRT
<213> ORGANISM: rabbit

<400> SEQUENCE: 4

Gln Ala Ser Glu Ser Ile Ser Asn Tyr Leu Ala
1               5                   10

<210> SEQ ID NO 5
<211> LENGTH: 11
<212> TYPE: PRT
<213> ORGANISM: rabbit

<400> SEQUENCE: 5

Gln Ala Ser Gln Asn Ile Tyr Ser Asn Leu Ala
1               5                   10

<210> SEQ ID NO 6
<211> LENGTH: 11
<212> TYPE: PRT
<213> ORGANISM: rabbit

<400> SEQUENCE: 6

Gln Ala Ser Gln Ser Val Asn Asn Leu Leu Ala
1               5                   10

<210> SEQ ID NO 7
<211> LENGTH: 11
<212> TYPE: PRT
<213> ORGANISM: rabbit

<400> SEQUENCE: 7

Gln Ala Ser Glu Ser Ile Asn Asn Tyr Leu Ala
1               5                   10

<210> SEQ ID NO 8
<211> LENGTH: 11
<212> TYPE: PRT
<213> ORGANISM: rabbit

<400> SEQUENCE: 8

Leu Ala Ser Glu Asn Val Tyr Ser Ala Val Ala
1               5                   10

<210> SEQ ID NO 9
```

```
<211> LENGTH: 11
<212> TYPE: PRT
<213> ORGANISM: rabbit

<400> SEQUENCE: 9

Leu Ala Ser Glu Asn Val Tyr Gly Ala Val Ala
1               5                   10

<210> SEQ ID NO 10
<211> LENGTH: 11
<212> TYPE: PRT
<213> ORGANISM: rabbit

<400> SEQUENCE: 10

Gln Ala Ser Gln Ser Ile Ser Asn Leu Leu Ala
1               5                   10

<210> SEQ ID NO 11
<211> LENGTH: 11
<212> TYPE: PRT
<213> ORGANISM: rabbit

<400> SEQUENCE: 11

Leu Ala Ser Glu Asn Val Ala Ser Thr Val Ser
1               5                   10

<210> SEQ ID NO 12
<211> LENGTH: 14
<212> TYPE: PRT
<213> ORGANISM: rabbit

<400> SEQUENCE: 12

Thr Leu Ser Thr Gly Tyr Ser Val Gly Glu Tyr Pro Val Val
1               5                   10

<210> SEQ ID NO 13
<211> LENGTH: 14
<212> TYPE: PRT
<213> ORGANISM: rabbit

<400> SEQUENCE: 13

Thr Leu Arg Thr Gly Tyr Ser Val Gly Glu Tyr Pro Leu Val
1               5                   10

<210> SEQ ID NO 14
<211> LENGTH: 11
<212> TYPE: PRT
<213> ORGANISM: rabbit

<400> SEQUENCE: 14

Leu Ala Ser Glu Asp Ile Tyr Ser Gly Leu Ser
1               5                   10

<210> SEQ ID NO 15
<211> LENGTH: 11
<212> TYPE: PRT
<213> ORGANISM: rabbit

<400> SEQUENCE: 15

Gln Ala Ser Gln Ser Val Ser Asn Leu Leu Ala
1               5                   10

<210> SEQ ID NO 16
<211> LENGTH: 11
<212> TYPE: PRT
<213> ORGANISM: rabbit
```

-continued

<400> SEQUENCE: 16

Gln Ala Ser Glu Asp Ile Glu Ser Tyr Leu Ala
1               5                   10

<210> SEQ ID NO 17
<211> LENGTH: 12
<212> TYPE: PRT
<213> ORGANISM: rabbit

<400> SEQUENCE: 17

Gln Ser Ser Gln Ser Ile Ala Gly Ala Tyr Leu Ser
1               5                   10

<210> SEQ ID NO 18
<211> LENGTH: 10
<212> TYPE: PRT
<213> ORGANISM: rabbit

<400> SEQUENCE: 18

His Ser Glu Glu Ala Lys His Gln Gly Ser
1               5                   10

<210> SEQ ID NO 19
<211> LENGTH: 7
<212> TYPE: PRT
<213> ORGANISM: rabbit

<400> SEQUENCE: 19

Gly Ala Ser Asn Leu Glu Ser
1               5

<210> SEQ ID NO 20
<211> LENGTH: 7
<212> TYPE: PRT
<213> ORGANISM: rabbit

<400> SEQUENCE: 20

Arg Ala Ser Thr Leu Ala Ser
1               5

<210> SEQ ID NO 21
<211> LENGTH: 7
<212> TYPE: PRT
<213> ORGANISM: rabbit

<400> SEQUENCE: 21

Leu Ala Phe Thr Leu Ala Ser
1               5

<210> SEQ ID NO 22
<211> LENGTH: 7
<212> TYPE: PRT
<213> ORGANISM: rabbit

<400> SEQUENCE: 22

Gly Ala Ser Asp Leu Glu Ser
1               5

<210> SEQ ID NO 23
<211> LENGTH: 10
<212> TYPE: PRT
<213> ORGANISM: rabbit

<400> SEQUENCE: 23

His Thr Asp Asp Ile Lys His Gln Gly Ser
1               5                   10

<210> SEQ ID NO 24
<211> LENGTH: 7
<212> TYPE: PRT
<213> ORGANISM: rabbit

<400> SEQUENCE: 24

Leu Ala Ser Lys Leu Ala Ser
1               5

<210> SEQ ID NO 25
<211> LENGTH: 13
<212> TYPE: PRT
<213> ORGANISM: rabbit

<400> SEQUENCE: 25

Ala Thr Ala His Gly Ser Gly Ser Ser Phe His Val Val
1               5                   10

<210> SEQ ID NO 26
<211> LENGTH: 10
<212> TYPE: PRT
<213> ORGANISM: rabbit

<400> SEQUENCE: 26

Gln Ser Gly Asp Tyr Ser Ala Gly Leu Thr
1               5                   10

<210> SEQ ID NO 27
<211> LENGTH: 10
<212> TYPE: PRT
<213> ORGANISM: rabbit

<400> SEQUENCE: 27

Gln Ser Gly Tyr Tyr Ser Ala Gly Leu Thr
1               5                   10

<210> SEQ ID NO 28
<211> LENGTH: 10
<212> TYPE: PRT
<213> ORGANISM: rabbit

<400> SEQUENCE: 28

Gln Ser Gly Tyr Tyr Ser Ala Gly Val Thr
1               5                   10

<210> SEQ ID NO 29
<211> LENGTH: 14
<212> TYPE: PRT
<213> ORGANISM: rabbit

<400> SEQUENCE: 29

Gln Gly Gly Asp Tyr Ser Ser Ser Ser Tyr Gly Tyr Gly
1               5                   10

<210> SEQ ID NO 30
<211> LENGTH: 10
<212> TYPE: PRT
<213> ORGANISM: rabbit

<400> SEQUENCE: 30

Gln Ser Gly Tyr Tyr Ser Pro Gly Val Thr
1               5                   10

<210> SEQ ID NO 31
<211> LENGTH: 10
<212> TYPE: PRT
<213> ORGANISM: rabbit

<400> SEQUENCE: 31

Gln Ser Gly Tyr Tyr Ser Gly Gly Ala Thr
1               5                   10

<210> SEQ ID NO 32
<211> LENGTH: 9
<212> TYPE: PRT
<213> ORGANISM: rabbit

<400> SEQUENCE: 32

Gln Gly Tyr Ser Ser Tyr Pro Pro Thr
1               5

<210> SEQ ID NO 33
<211> LENGTH: 8
<212> TYPE: PRT
<213> ORGANISM: rabbit

<400> SEQUENCE: 33

Gln Gly Tyr Ser Ser Tyr Pro Thr
1               5

<210> SEQ ID NO 34
<211> LENGTH: 12
<212> TYPE: PRT
<213> ORGANISM: rabbit

<400> SEQUENCE: 34

Ala Gly Tyr Lys Ser Ser Ser Thr Asp Gly Ile Ala
1               5                   10

<210> SEQ ID NO 35
<211> LENGTH: 11
<212> TYPE: PRT
<213> ORGANISM: rabbit

<400> SEQUENCE: 35

Gln Ser Gly Tyr Tyr Ser Ala Gly His Leu Thr
1               5                   10

<210> SEQ ID NO 36
<211> LENGTH: 12
<212> TYPE: PRT
<213> ORGANISM: rabbit

<400> SEQUENCE: 36

Leu Gly Gly Phe Gly Tyr Ser Thr Thr Gly Leu Thr
1               5                   10

<210> SEQ ID NO 37
<211> LENGTH: 13
<212> TYPE: PRT
<213> ORGANISM: rabbit

<400> SEQUENCE: 37

Ala Ile Ala His Gly Thr Glu Ser Ser Phe His Val Val
1               5                   10

<210> SEQ ID NO 38
<211> LENGTH: 13

```
<212> TYPE: PRT
<213> ORGANISM: rabbit

<400> SEQUENCE: 38

Ala Thr Gly His Gly Ser Gly Ser Ala Gly Val Val
1               5                   10

<210> SEQ ID NO 39
<211> LENGTH: 12
<212> TYPE: PRT
<213> ORGANISM: rabbit

<400> SEQUENCE: 39

Leu Gly Gly Tyr Pro Tyr Ser Ser Thr Gly Thr Ala
1               5                   10

<210> SEQ ID NO 40
<211> LENGTH: 11
<212> TYPE: PRT
<213> ORGANISM: rabbit

<400> SEQUENCE: 40

Gln Ser Gly Trp Tyr Ser Ala Gly Ala Leu Thr
1               5                   10

<210> SEQ ID NO 41
<211> LENGTH: 11
<212> TYPE: PRT
<213> ORGANISM: rabbit

<400> SEQUENCE: 41

Gln Ser Gly Tyr Tyr Arg Ala Gly Asp Leu Thr
1               5                   10

<210> SEQ ID NO 42
<211> LENGTH: 11
<212> TYPE: PRT
<213> ORGANISM: rabbit

<400> SEQUENCE: 42

Gln Ser Gly Tyr Tyr Ser Ala Gly Ala Leu Thr
1               5                   10

<210> SEQ ID NO 43
<211> LENGTH: 10
<212> TYPE: PRT
<213> ORGANISM: rabbit

<400> SEQUENCE: 43

Gln Ser Asn Ala Trp Ser Val Gly Met Thr
1               5                   10

<210> SEQ ID NO 44
<211> LENGTH: 10
<212> TYPE: PRT
<213> ORGANISM: rabbit

<400> SEQUENCE: 44

Ala Ala Gln Tyr Ser Gly Asn Ile Tyr Thr
1               5                   10

<210> SEQ ID NO 45
<211> LENGTH: 5
<212> TYPE: PRT
<213> ORGANISM: rabbit
```

```
<400> SEQUENCE: 45

Asn Tyr Ala Met Thr
1               5

<210> SEQ ID NO 46
<211> LENGTH: 5
<212> TYPE: PRT
<213> ORGANISM: rabbit

<400> SEQUENCE: 46

Ser Tyr Gly Leu Ser
1               5

<210> SEQ ID NO 47
<211> LENGTH: 5
<212> TYPE: PRT
<213> ORGANISM: rabbit

<400> SEQUENCE: 47

Thr Tyr Gly Val Ser
1               5

<210> SEQ ID NO 48
<211> LENGTH: 5
<212> TYPE: PRT
<213> ORGANISM: rabbit

<400> SEQUENCE: 48

Ser Asn Ala Met Gly
1               5

<210> SEQ ID NO 49
<211> LENGTH: 5
<212> TYPE: PRT
<213> ORGANISM: rabbit

<400> SEQUENCE: 49

Thr Asn Ala Met Gly
1               5

<210> SEQ ID NO 50
<211> LENGTH: 6
<212> TYPE: PRT
<213> ORGANISM: rabbit

<400> SEQUENCE: 50

Ser Ser Asp Trp Ile Cys
1               5

<210> SEQ ID NO 51
<211> LENGTH: 5
<212> TYPE: PRT
<213> ORGANISM: rabbit

<400> SEQUENCE: 51

Ser Asp Val Ile Ser
1               5

<210> SEQ ID NO 52
<211> LENGTH: 5
<212> TYPE: PRT
<213> ORGANISM: rabbit

<400> SEQUENCE: 52

Thr Tyr Ala Met Gly
```

-continued

```
<210> SEQ ID NO 53
<211> LENGTH: 5
<212> TYPE: PRT
<213> ORGANISM: rabbit

<400> SEQUENCE: 53

Ser Asn Ala Met Thr
1               5

<210> SEQ ID NO 54
<211> LENGTH: 5
<212> TYPE: PRT
<213> ORGANISM: rabbit

<400> SEQUENCE: 54

Asp Phe Ala Met Ser
1               5

<210> SEQ ID NO 55
<211> LENGTH: 5
<212> TYPE: PRT
<213> ORGANISM: rabbit

<400> SEQUENCE: 55

Ser Tyr Gly Met Asn
1               5

<210> SEQ ID NO 56
<211> LENGTH: 5
<212> TYPE: PRT
<213> ORGANISM: rabbit

<400> SEQUENCE: 56

Ser Asn Ala Met Ser
1               5

<210> SEQ ID NO 57
<211> LENGTH: 5
<212> TYPE: PRT
<213> ORGANISM: rabbit

<400> SEQUENCE: 57

Thr Asn Ala Ile Ser
1               5

<210> SEQ ID NO 58
<211> LENGTH: 5
<212> TYPE: PRT
<213> ORGANISM: rabbit

<400> SEQUENCE: 58

Ser Tyr Tyr Met Ser
1               5

<210> SEQ ID NO 59
<211> LENGTH: 5
<212> TYPE: PRT
<213> ORGANISM: rabbit

<400> SEQUENCE: 59

Ser Tyr Thr Met Ser
1               5
```

```
<210> SEQ ID NO 60
<211> LENGTH: 5
<212> TYPE: PRT
<213> ORGANISM: rabbit

<400> SEQUENCE: 60

Ser Asn Ala Ile Ser
1               5

<210> SEQ ID NO 61
<211> LENGTH: 5
<212> TYPE: PRT
<213> ORGANISM: rabbit

<400> SEQUENCE: 61

Thr Asn Ala Met Ser
1               5

<210> SEQ ID NO 62
<211> LENGTH: 6
<212> TYPE: PRT
<213> ORGANISM: rabbit

<400> SEQUENCE: 62

Ser Ser Tyr Trp Ile Cys
1               5

<210> SEQ ID NO 63
<211> LENGTH: 5
<212> TYPE: PRT
<213> ORGANISM: rabbit

<400> SEQUENCE: 63

Asn Tyr Gly Val Asn
1               5

<210> SEQ ID NO 64
<211> LENGTH: 15
<212> TYPE: PRT
<213> ORGANISM: rabbit

<400> SEQUENCE: 64

Ile Ile Ser Ser Asn Gly Gly Ala Asp Tyr Ala Ser Trp Ala Lys
1               5                   10                  15

<210> SEQ ID NO 65
<211> LENGTH: 16
<212> TYPE: PRT
<213> ORGANISM: rabbit

<400> SEQUENCE: 65

Tyr Phe Asp Pro Val Phe Gly Asn Ile Tyr Tyr Ala Thr Trp Val Asp
1               5                   10                  15

<210> SEQ ID NO 66
<211> LENGTH: 16
<212> TYPE: PRT
<213> ORGANISM: rabbit

<400> SEQUENCE: 66

Tyr Asn Asp Pro Ile Phe Gly Asn Thr Tyr Tyr Ala Thr Trp Val Asn
1               5                   10                  15

<210> SEQ ID NO 67
<211> LENGTH: 15
<212> TYPE: PRT
```

```
<213> ORGANISM: rabbit

<400> SEQUENCE: 67

Ile Ile Ser Ser Ser Gly Gly Thr Tyr Tyr Ala Ser Trp Ala Lys
1               5                   10                  15

<210> SEQ ID NO 68
<211> LENGTH: 15
<212> TYPE: PRT
<213> ORGANISM: rabbit

<400> SEQUENCE: 68

Ile Ile Ser Ser Ser Gly Ser Thr Tyr Tyr Ala Ser Trp Ala Lys
1               5                   10                  15

<210> SEQ ID NO 69
<211> LENGTH: 17
<212> TYPE: PRT
<213> ORGANISM: rabbit

<400> SEQUENCE: 69

Cys Ile Tyr Thr Gly Ser Ser Ser Thr Trp Tyr Ala Ser Trp Ala
1               5                   10                  15

Lys

<210> SEQ ID NO 70
<211> LENGTH: 16
<212> TYPE: PRT
<213> ORGANISM: rabbit

<400> SEQUENCE: 70

Tyr Ile Tyr Thr Gly Asp Gly Ser Thr Asp Tyr Ala Ser Trp Val Asn
1               5                   10                  15

<210> SEQ ID NO 71
<211> LENGTH: 15
<212> TYPE: PRT
<213> ORGANISM: rabbit

<400> SEQUENCE: 71

Ser Ile Tyr Ala Ser Arg Ser Pro Tyr Tyr Ala Ser Trp Ala Lys
1               5                   10                  15

<210> SEQ ID NO 72
<211> LENGTH: 15
<212> TYPE: PRT
<213> ORGANISM: rabbit

<400> SEQUENCE: 72

Thr Ile Ile Tyr Gly Asp Asn Thr Tyr Tyr Ala Ser Trp Ala Lys
1               5                   10                  15

<210> SEQ ID NO 73
<211> LENGTH: 17
<212> TYPE: PRT
<213> ORGANISM: rabbit

<400> SEQUENCE: 73

Val Val Tyr Ala Gly Thr Arg Gly Asp Thr Tyr Tyr Ala Asn Trp Ala
1               5                   10                  15

Lys

<210> SEQ ID NO 74
<211> LENGTH: 16
```

```
<212> TYPE: PRT
<213> ORGANISM: rabbit

<400> SEQUENCE: 74

Tyr Ile Asp Pro Asp Tyr Gly Ser Thr Tyr Tyr Ala Ser Trp Val Asn
1               5                   10                  15

<210> SEQ ID NO 75
<211> LENGTH: 15
<212> TYPE: PRT
<213> ORGANISM: rabbit

<400> SEQUENCE: 75

Ile Thr Tyr Pro Ser Gly Asn Val Tyr Tyr Ala Ser Trp Ala Lys
1               5                   10                  15

<210> SEQ ID NO 76
<211> LENGTH: 15
<212> TYPE: PRT
<213> ORGANISM: rabbit

<400> SEQUENCE: 76

Tyr Ser Ser Tyr Gly Asn Asn Ala His Tyr Thr Asn Trp Ala Lys
1               5                   10                  15

<210> SEQ ID NO 77
<211> LENGTH: 15
<212> TYPE: PRT
<213> ORGANISM: rabbit

<400> SEQUENCE: 77

Ile Ile Ile Gly Ser Gly Thr Thr Tyr Tyr Ala Asn Trp Ala Lys
1               5                   10                  15

<210> SEQ ID NO 78
<211> LENGTH: 15
<212> TYPE: PRT
<213> ORGANISM: rabbit

<400> SEQUENCE: 78

Ile Ile Ser Ser Ser Gly Thr Ser Tyr Tyr Ala Thr Trp Ala Lys
1               5                   10                  15

<210> SEQ ID NO 79
<211> LENGTH: 15
<212> TYPE: PRT
<213> ORGANISM: rabbit

<400> SEQUENCE: 79

Ile Ile Ser Ser Ser Gly Ser Ala Tyr Tyr Ala Thr Trp Ala Lys
1               5                   10                  15

<210> SEQ ID NO 80
<211> LENGTH: 15
<212> TYPE: PRT
<213> ORGANISM: rabbit

<400> SEQUENCE: 80

Ile Ile Val Gly Ser Gly Thr Thr Tyr Tyr Ala Asp Trp Ala Lys
1               5                   10                  15

<210> SEQ ID NO 81
<211> LENGTH: 15
<212> TYPE: PRT
<213> ORGANISM: rabbit
```

```
<400> SEQUENCE: 81

Thr Ile Thr Tyr Gly Thr Asn Ala Tyr Tyr Ala Ser Trp Ala Lys
1               5                   10                  15

<210> SEQ ID NO 82
<211> LENGTH: 17
<212> TYPE: PRT
<213> ORGANISM: rabbit

<400> SEQUENCE: 82

Cys Ile Tyr Thr Gly Ser Asn Gly Ser Thr Tyr Tyr Ala Ser Trp Ala
1               5                   10                  15

Lys

<210> SEQ ID NO 83
<211> LENGTH: 16
<212> TYPE: PRT
<213> ORGANISM: rabbit

<400> SEQUENCE: 83

Tyr Ile Asp Pro Val Phe Gly Ser Thr Tyr Tyr Ala Ser Trp Val Asn
1               5                   10                  15

<210> SEQ ID NO 84
<211> LENGTH: 17
<212> TYPE: PRT
<213> ORGANISM: rabbit

<400> SEQUENCE: 84

Asp Asp Glu Gly Tyr Asp Asp Tyr Gly Asp Tyr Met Gly Tyr Phe Thr
1               5                   10                  15

Leu

<210> SEQ ID NO 85
<211> LENGTH: 14
<212> TYPE: PRT
<213> ORGANISM: rabbit

<400> SEQUENCE: 85

Asp Arg Ile Tyr Val Ser Ser Val Gly Tyr Ala Phe Asn Leu
1               5                   10

<210> SEQ ID NO 86
<211> LENGTH: 14
<212> TYPE: PRT
<213> ORGANISM: rabbit
<220> FEATURE:
<221> NAME/KEY: MISC_FEATURE
<222> LOCATION: (11)..(14)
<223> OTHER INFORMATION: Xaa = is an unknown amino acid

<400> SEQUENCE: 86

Asp Arg Ala Tyr Ala Ser Ser Ser Gly Tyr Xaa Xaa Xaa Xaa
1               5                   10

<210> SEQ ID NO 87
<211> LENGTH: 13
<212> TYPE: PRT
<213> ORGANISM: rabbit

<400> SEQUENCE: 87

Asp Trp Ile Ala Ala Gly Lys Ser Tyr Gly Leu Asp Leu
1               5                   10
```

<210> SEQ ID NO 88
<211> LENGTH: 9
<212> TYPE: PRT
<213> ORGANISM: rabbit

<400> SEQUENCE: 88

Arg Tyr Thr Gly Asp Asn Gly Asn Leu
1               5

<210> SEQ ID NO 89
<211> LENGTH: 13
<212> TYPE: PRT
<213> ORGANISM: rabbit

<400> SEQUENCE: 89

Asp Ala Ala Tyr Ala Gly Tyr Gly Trp Ile Phe Asn Leu
1               5                   10

<210> SEQ ID NO 90
<211> LENGTH: 11
<212> TYPE: PRT
<213> ORGANISM: rabbit

<400> SEQUENCE: 90

Gly Asp Ala Gly Ser Ile Pro Tyr Phe Lys Leu
1               5                   10

<210> SEQ ID NO 91
<211> LENGTH: 7
<212> TYPE: PRT
<213> ORGANISM: rabbit

<400> SEQUENCE: 91

Gly Asn Val Phe Ser Asp Leu
1               5

<210> SEQ ID NO 92
<211> LENGTH: 7
<212> TYPE: PRT
<213> ORGANISM: rabbit

<400> SEQUENCE: 92

Gly Leu Thr Tyr Tyr Pro Leu
1               5

<210> SEQ ID NO 93
<211> LENGTH: 12
<212> TYPE: PRT
<213> ORGANISM: rabbit

<400> SEQUENCE: 93

Gly Ala Tyr Ser Gly Tyr Pro Ser Tyr Phe Asn Leu
1               5                   10

<210> SEQ ID NO 94
<211> LENGTH: 5
<212> TYPE: PRT
<213> ORGANISM: rabbit

<400> SEQUENCE: 94

Gly Phe Phe Asn Leu
1               5

<210> SEQ ID NO 95
<211> LENGTH: 7
<212> TYPE: PRT

<213> ORGANISM: rabbit

<400> SEQUENCE: 95

Gly Asn Ala Tyr Ser Asp Leu
1               5

<210> SEQ ID NO 96
<211> LENGTH: 22
<212> TYPE: PRT
<213> ORGANISM: rabbit

<400> SEQUENCE: 96

Asp Gln Pro Ile Ile Tyr Gly Ala Tyr Gly Asp Tyr Gly Leu Ala Thr
1               5                   10                  15

Gly Thr Arg Leu Asp Leu
            20

<210> SEQ ID NO 97
<211> LENGTH: 22
<212> TYPE: PRT
<213> ORGANISM: rabbit

<400> SEQUENCE: 97

Asp Gln Pro Ile Ile Asp Ala Ala Tyr Gly Asp Tyr Gly Ile Ala Thr
1               5                   10                  15

Gly Thr Arg Leu Asp Leu
            20

<210> SEQ ID NO 98
<211> LENGTH: 22
<212> TYPE: PRT
<213> ORGANISM: rabbit

<400> SEQUENCE: 98

Asp Gln Pro Ile Ile Thr Thr Asp Tyr Gly Gly Tyr Gly Ile Ala Thr
1               5                   10                  15

Gly Thr Arg Leu Asp Leu
            20

<210> SEQ ID NO 99
<211> LENGTH: 19
<212> TYPE: PRT
<213> ORGANISM: rabbit

<400> SEQUENCE: 99

Asp Gln Pro Ile Thr Tyr Ala Gly Tyr Gly Tyr Ala Thr Gly Thr Arg
1               5                   10                  15

Leu Asp Leu

<210> SEQ ID NO 100
<211> LENGTH: 7
<212> TYPE: PRT
<213> ORGANISM: rabbit

<400> SEQUENCE: 100

Gly Asn Thr Tyr Ser Asp Leu
1               5

<210> SEQ ID NO 101
<211> LENGTH: 13
<212> TYPE: PRT
<213> ORGANISM: rabbit

<400> SEQUENCE: 101

```
Ala Tyr Ile Tyr Tyr Gly Gly Tyr Gly Phe Phe Asp Leu
1               5                   10
```

<210> SEQ ID NO 102
<211> LENGTH: 10
<212> TYPE: PRT
<213> ORGANISM: rabbit

<400> SEQUENCE: 102

```
Glu Ala Ser Phe Tyr Tyr Gly Met Asp Leu
1               5                   10
```

<210> SEQ ID NO 103
<211> LENGTH: 36
<212> TYPE: DNA
<213> ORGANISM: artificial sequence
<220> FEATURE:
<223> OTHER INFORMATION: primer

<400> SEQUENCE: 103
ggcctctaga cagcctgtgc tgactcagtc gccctc         36

<210> SEQ ID NO 104
<211> LENGTH: 43
<212> TYPE: DNA
<213> ORGANISM: artificial sequence
<220> FEATURE:
<223> OTHER INFORMATION: primer

<400> SEQUENCE: 104
cgagggggca gccttgggct gacctgtgac ggtcagctgg gtc         43

<210> SEQ ID NO 105
<211> LENGTH: 43
<212> TYPE: DNA
<213> ORGANISM: artificial sequence
<220> FEATURE:
<223> OTHER INFORMATION: primer

<400> SEQUENCE: 105
gacccagctg accgtcacag gtcagcccaa ggctgccccc tcg         43

<210> SEQ ID NO 106
<211> LENGTH: 34
<212> TYPE: DNA
<213> ORGANISM: artificial sequence
<220> FEATURE:
<223> OTHER INFORMATION: primer

<400> SEQUENCE: 106
tctaatctcg agcagcagca gctgatggag tccg         34

<210> SEQ ID NO 107
<211> LENGTH: 47
<212> TYPE: DNA
<213> ORGANISM: artificial sequence
<220> FEATURE:
<223> OTHER INFORMATION: primer

<400> SEQUENCE: 107
gaccgatggg cccttggtgg aggctgagga gacggtgacc agggtgc         47

<210> SEQ ID NO 108
<211> LENGTH: 47
<212> TYPE: DNA
<213> ORGANISM: artificial sequence

```
<220> FEATURE:
<223> OTHER INFORMATION: primer

<400> SEQUENCE: 108
gcaccctggt caccgtctcc tcagcctcca ccaagggccc atcggtc        47

<210> SEQ ID NO 109
<211> LENGTH: 28
<212> TYPE: DNA
<213> ORGANISM: artificial sequence
<220> FEATURE:
<223> OTHER INFORMATION: primer

<400> SEQUENCE: 109
ccactgtcag agctcccggg tagaagtc                             28

<210> SEQ ID NO 110
<211> LENGTH: 23
<212> TYPE: DNA
<213> ORGANISM: artificial sequence
<220> FEATURE:
<223> OTHER INFORMATION: primer

<400> SEQUENCE: 110
gtcaccggtt cggggaagta gtc                                  23

<210> SEQ ID NO 111
<211> LENGTH: 10
<212> TYPE: PRT
<213> ORGANISM: murine

<400> SEQUENCE: 111

Gly Phe Asn Ile Lys Asp Tyr Tyr Met His
1               5                   10

<210> SEQ ID NO 112
<211> LENGTH: 10
<212> TYPE: PRT
<213> ORGANISM: murine
<220> FEATURE:
<221> NAME/KEY: MISC_FEATURE
<222> LOCATION: (9)..(9)
<223> OTHER INFORMATION: Xaa = any amino acid

<400> SEQUENCE: 112

Asp Phe Asn Ile Lys Asp Tyr Tyr Xaa His
1               5                   10

<210> SEQ ID NO 113
<211> LENGTH: 10
<212> TYPE: PRT
<213> ORGANISM: murine

<400> SEQUENCE: 113

Gly Leu Asn Ile Lys Asp Tyr Tyr Met His
1               5                   10

<210> SEQ ID NO 114
<211> LENGTH: 10
<212> TYPE: PRT
<213> ORGANISM: murine

<400> SEQUENCE: 114

Gly Phe Asn Ile Lys Asp Tyr Tyr Ile His
1               5                   10
```

```
<210> SEQ ID NO 115
<211> LENGTH: 10
<212> TYPE: PRT
<213> ORGANISM: murine

<400> SEQUENCE: 115

Gly Phe Asn Ile Lys Asp Tyr Tyr Leu His
1               5                   10

<210> SEQ ID NO 116
<211> LENGTH: 10
<212> TYPE: PRT
<213> ORGANISM: murine

<400> SEQUENCE: 116

Gly Tyr Thr Phe Thr Ser Tyr Val Met His
1               5                   10

<210> SEQ ID NO 117
<211> LENGTH: 17
<212> TYPE: PRT
<213> ORGANISM: murine
<220> FEATURE:
<221> NAME/KEY: MISC_FEATURE
<222> LOCATION: (4)..(4)
<223> OTHER INFORMATION: Xaa = any amino acid

<400> SEQUENCE: 117

Trp Ile Asp Xaa Glu Asn Gly Asp Thr Lys Tyr Ala Pro Lys Phe Gln
1               5                   10                  15

Gly

<210> SEQ ID NO 118
<211> LENGTH: 17
<212> TYPE: PRT
<213> ORGANISM: murine

<400> SEQUENCE: 118

Trp Ile Asp Pro Glu Asn Gly Asp Thr Lys Tyr Ala Pro Lys Phe Gln
1               5                   10                  15

Gly

<210> SEQ ID NO 119
<211> LENGTH: 17
<212> TYPE: PRT
<213> ORGANISM: murine
<220> FEATURE:
<221> NAME/KEY: MISC_FEATURE
<222> LOCATION: (6)..(6)
<223> OTHER INFORMATION: Xaa = any amino acid

<400> SEQUENCE: 119

Trp Ile Asp Pro Glu Xaa Asp Thr Lys Tyr Ala Pro Lys Phe Gln
1               5                   10                  15

Gly

<210> SEQ ID NO 120
<211> LENGTH: 17
<212> TYPE: PRT
<213> ORGANISM: murine

<400> SEQUENCE: 120

Trp Ile Asp Pro Glu Asn Gly Asn Thr Lys Tyr Ala Pro Lys Phe Gln
1               5                   10                  15

Gly
```

<210> SEQ ID NO 121
<211> LENGTH: 17
<212> TYPE: PRT
<213> ORGANISM: murine

<400> SEQUENCE: 121

Trp Ile Asp Pro Asp Asn Gly Asp Thr Lys Tyr Ala Pro Lys Phe Arg
1               5                   10                  15

Gly

<210> SEQ ID NO 122
<211> LENGTH: 17
<212> TYPE: PRT
<213> ORGANISM: murine

<400> SEQUENCE: 122

Trp Ile Asp Pro Asp Asn Gly Asp Thr Lys Tyr Ala Pro Lys Phe Arg
1               5                   10                  15

Asp

<210> SEQ ID NO 123
<211> LENGTH: 17
<212> TYPE: PRT
<213> ORGANISM: murine

<400> SEQUENCE: 123

Tyr Ile Asn Pro Tyr Asn Asp Val Thr Lys Asn Asn Glu Lys Phe Arg
1               5                   10                  15

Gly

<210> SEQ ID NO 124
<211> LENGTH: 17
<212> TYPE: PRT
<213> ORGANISM: murine

<400> SEQUENCE: 124

Tyr Ile Asn Pro Tyr Asn Asp Ile Thr Asn Tyr Asn Glu Lys Phe Lys
1               5                   10                  15

Gly

<210> SEQ ID NO 125
<211> LENGTH: 17
<212> TYPE: PRT
<213> ORGANISM: murine

<400> SEQUENCE: 125

Tyr Ile Asn Pro Tyr Asn Asp Gly Ser Lys Tyr Asn Glu Lys Phe Lys
1               5                   10                  15

Gly

<210> SEQ ID NO 126
<211> LENGTH: 17
<212> TYPE: PRT
<213> ORGANISM: murine

<400> SEQUENCE: 126

Tyr Ile Asn Pro Tyr Asn Asp Gly Thr Lys Tyr Asn Glu Lys Phe Lys
1               5                   10                  15

Gly

-continued

```
<210> SEQ ID NO 127
<211> LENGTH: 17
<212> TYPE: PRT
<213> ORGANISM: murine

<400> SEQUENCE: 127

Tyr Ile Asn Pro Tyr Asn Asp Gly Thr Arg Tyr Asn Glu Lys Phe Lys
1               5                   10                  15

Gly

<210> SEQ ID NO 128
<211> LENGTH: 17
<212> TYPE: PRT
<213> ORGANISM: murine

<400> SEQUENCE: 128

Tyr Ile Asn Pro Tyr Asn Asp Val Thr Asn Tyr Asn Glu Lys Phe Lys
1               5                   10                  15

Gly

<210> SEQ ID NO 129
<211> LENGTH: 17
<212> TYPE: PRT
<213> ORGANISM: murine

<400> SEQUENCE: 129

Tyr Ile Asn Pro Tyr Asn Asp Gly Thr Asn Tyr Asn Glu Lys Phe Lys
1               5                   10                  15

Gly

<210> SEQ ID NO 130
<211> LENGTH: 17
<212> TYPE: PRT
<213> ORGANISM: murine

<400> SEQUENCE: 130

Tyr Ile Asn Pro Tyr Asn Asp Val Thr Lys Tyr Asn Glu Lys Phe Arg
1               5                   10                  15

Gly

<210> SEQ ID NO 131
<211> LENGTH: 13
<212> TYPE: PRT
<213> ORGANISM: murine

<400> SEQUENCE: 131

Lys Asn Tyr Tyr Val Ser Asn Tyr Asn Tyr Phe Asp Val
1               5                   10

<210> SEQ ID NO 132
<211> LENGTH: 13
<212> TYPE: PRT
<213> ORGANISM: murine

<400> SEQUENCE: 132

Lys Asn Tyr Tyr Val Ser Asp Tyr Asn Tyr Phe Asp Val
1               5                   10

<210> SEQ ID NO 133
<211> LENGTH: 13
<212> TYPE: PRT
<213> ORGANISM: murine

<400> SEQUENCE: 133
```

Lys Asn Tyr Tyr Val Ser Asn Tyr Asn Phe Phe Asp Val
1               5                   10

<210> SEQ ID NO 134
<211> LENGTH: 12
<212> TYPE: PRT
<213> ORGANISM: murine

<400> SEQUENCE: 134

Lys Arg Gly Gly Tyr Asp Gly Ala Trp Phe Ala Tyr
1               5                   10

<210> SEQ ID NO 135
<211> LENGTH: 10
<212> TYPE: PRT
<213> ORGANISM: murine

<400> SEQUENCE: 135

Gly Phe Asn Ile Lys Asp His Tyr Met His
1               5                   10

<210> SEQ ID NO 136
<211> LENGTH: 10
<212> TYPE: PRT
<213> ORGANISM: murine

<400> SEQUENCE: 136

Ala Phe Asn Ile Lys Asp His Tyr Met His
1               5                   10

<210> SEQ ID NO 137
<211> LENGTH: 10
<212> TYPE: PRT
<213> ORGANISM: murine

<400> SEQUENCE: 137

Gly Phe Asn Leu Lys Asp Tyr Tyr Met His
1               5                   10

<210> SEQ ID NO 138
<211> LENGTH: 10
<212> TYPE: PRT
<213> ORGANISM: murine

<400> SEQUENCE: 138

Gly Tyr Thr Phe Thr Asp Tyr Trp Leu His
1               5                   10

<210> SEQ ID NO 139
<211> LENGTH: 10
<212> TYPE: PRT
<213> ORGANISM: murine

<400> SEQUENCE: 139

Gly Phe Thr Phe Ser Ala Ala Trp Met Asp
1               5                   10

<210> SEQ ID NO 140
<211> LENGTH: 10
<212> TYPE: PRT
<213> ORGANISM: murine

<400> SEQUENCE: 140

Gly Tyr Thr Phe Thr Glu Tyr Thr Met His
1               5                   10

```
<210> SEQ ID NO 141
<211> LENGTH: 10
<212> TYPE: PRT
<213> ORGANISM: murine

<400> SEQUENCE: 141

Gly Phe Thr Phe Ser Gly Phe Ala Met Ser
1               5                   10

<210> SEQ ID NO 142
<211> LENGTH: 10
<212> TYPE: PRT
<213> ORGANISM: murine

<400> SEQUENCE: 142

Gly Phe Thr Phe Thr Gly Tyr Ala Met Ser
1               5                   10

<210> SEQ ID NO 143
<211> LENGTH: 10
<212> TYPE: PRT
<213> ORGANISM: murine

<400> SEQUENCE: 143

Gly Phe Thr Phe Ser Ser His Ala Met Ser
1               5                   10

<210> SEQ ID NO 144
<211> LENGTH: 10
<212> TYPE: PRT
<213> ORGANISM: murine

<400> SEQUENCE: 144

Gly Tyr Thr Phe Thr Glu Phe Thr Met His
1               5                   10

<210> SEQ ID NO 145
<211> LENGTH: 10
<212> TYPE: PRT
<213> ORGANISM: murine

<400> SEQUENCE: 145

Gly Tyr Ile Phe Thr Ser Phe Tyr Ile His
1               5                   10

<210> SEQ ID NO 146
<211> LENGTH: 10
<212> TYPE: PRT
<213> ORGANISM: murine

<400> SEQUENCE: 146

Gly Tyr Thr Phe Thr Ser Phe Tyr Ile His
1               5                   10

<210> SEQ ID NO 147
<211> LENGTH: 10
<212> TYPE: PRT
<213> ORGANISM: murine

<400> SEQUENCE: 147

Gly Tyr Thr Phe Thr Asp Tyr Trp Met His
1               5                   10

<210> SEQ ID NO 148
```

```
<211> LENGTH: 10
<212> TYPE: PRT
<213> ORGANISM: murine

<400> SEQUENCE: 148

Gly Tyr Thr Phe Thr Asp Asn Trp Ile His
1               5                   10

<210> SEQ ID NO 149
<211> LENGTH: 10
<212> TYPE: PRT
<213> ORGANISM: murine

<400> SEQUENCE: 149

Gly Tyr Ser Phe Thr Asp Tyr Ile Ile Leu
1               5                   10

<210> SEQ ID NO 150
<211> LENGTH: 10
<212> TYPE: PRT
<213> ORGANISM: murine

<400> SEQUENCE: 150

Gly Phe Asn Ile Lys Asp Ser Tyr Ile His
1               5                   10

<210> SEQ ID NO 151
<211> LENGTH: 10
<212> TYPE: PRT
<213> ORGANISM: murine
<220> FEATURE:
<221> NAME/KEY: MISC_FEATURE
<222> LOCATION: (6)..(6)
<223> OTHER INFORMATION: Xaa = any amino acid

<400> SEQUENCE: 151

Gly Phe Asn Ile Lys Xaa Ser Tyr Ile His
1               5                   10

<210> SEQ ID NO 152
<211> LENGTH: 10
<212> TYPE: PRT
<213> ORGANISM: murine

<400> SEQUENCE: 152

Gly Tyr Thr Phe Thr Ser Tyr Thr Ile His
1               5                   10

<210> SEQ ID NO 153
<211> LENGTH: 10
<212> TYPE: PRT
<213> ORGANISM: murine

<400> SEQUENCE: 153

Gly Tyr Thr Phe Thr Glu Tyr Ile Met His
1               5                   10

<210> SEQ ID NO 154
<211> LENGTH: 16
<212> TYPE: PRT
<213> ORGANISM: murine

<400> SEQUENCE: 154

Trp Ile Pro Glu Asn Gly Asp Thr Glu Tyr Ala Pro Lys Phe Gln Gly
1               5                   10                  15
```

```
<210> SEQ ID NO 155
<211> LENGTH: 16
<212> TYPE: PRT
<213> ORGANISM: murine

<400> SEQUENCE: 155

Trp Ile Pro Glu Ser Gly Asp Thr Glu Tyr Ala Pro Lys Phe Gln Gly
1               5                   10                  15

<210> SEQ ID NO 156
<211> LENGTH: 16
<212> TYPE: PRT
<213> ORGANISM: murine

<400> SEQUENCE: 156

Trp Ile Pro Glu Asn Gly Asn Thr Glu Tyr Ala Pro Lys Phe Gln Gly
1               5                   10                  15

<210> SEQ ID NO 157
<211> LENGTH: 16
<212> TYPE: PRT
<213> ORGANISM: murine
<220> FEATURE:
<221> NAME/KEY: MISC_FEATURE
<222> LOCATION: (16)..(16)
<223> OTHER INFORMATION: Xaa = any amino acid

<400> SEQUENCE: 157

Trp Ile Pro Glu Asn Gly Asn Thr Glu Tyr Ala Pro Lys Phe Gln Xaa
1               5                   10                  15

<210> SEQ ID NO 158
<211> LENGTH: 17
<212> TYPE: PRT
<213> ORGANISM: murine

<400> SEQUENCE: 158

Trp Ile Asp Pro Glu Asn Gly Asn Thr Glu Tyr Ala Pro Lys Phe Gln
1               5                   10                  15

Gly

<210> SEQ ID NO 159
<211> LENGTH: 17
<212> TYPE: PRT
<213> ORGANISM: murine

<400> SEQUENCE: 159

Trp Ile Asp Pro Glu Ser Gly Asp Thr Glu Tyr Ala Pro Lys Phe Gln
1               5                   10                  15

Gly

<210> SEQ ID NO 160
<211> LENGTH: 17
<212> TYPE: PRT
<213> ORGANISM: murine

<400> SEQUENCE: 160

Thr Ile Asp Thr Ser Thr Gly Tyr Thr Gly Tyr Asn Gln Lys Phe Lys
1               5                   10                  15

Gly

<210> SEQ ID NO 161
<211> LENGTH: 19
<212> TYPE: PRT
<213> ORGANISM: murine
```

```
<400> SEQUENCE: 161

Glu Ile Arg Ser Lys Ala Asn Asn His Ala Thr Tyr Tyr Ala Glu Ser
1               5                   10                  15
Val Lys Gly

<210> SEQ ID NO 162
<211> LENGTH: 17
<212> TYPE: PRT
<213> ORGANISM: murine

<400> SEQUENCE: 162

Gly Val Asn Pro Asn Asn Gly Gly Ala Leu Tyr Asn Gln Lys Phe Lys
1               5                   10                  15
Gly

<210> SEQ ID NO 163
<211> LENGTH: 16
<212> TYPE: PRT
<213> ORGANISM: murine

<400> SEQUENCE: 163

Ser Ile Ser Ser Gly Gly Thr Thr Tyr Tyr Leu Asp Ser Val Lys Gly
1               5                   10                  15

<210> SEQ ID NO 164
<211> LENGTH: 16
<212> TYPE: PRT
<213> ORGANISM: murine

<400> SEQUENCE: 164

Ser Ile Ser Ser Gly Gly Ser Ala Tyr Tyr Pro Asp Ser Val Lys Gly
1               5                   10                  15

<210> SEQ ID NO 165
<211> LENGTH: 17
<212> TYPE: PRT
<213> ORGANISM: murine

<400> SEQUENCE: 165

Trp Ile Asp Pro Glu Ile Gly Ala Thr Lys Tyr Val Pro Lys Phe Gln
1               5                   10                  15
Gly

<210> SEQ ID NO 166
<211> LENGTH: 17
<212> TYPE: PRT
<213> ORGANISM: murine

<400> SEQUENCE: 166

Ser Ile Ser Ser Gly Gly Gly Thr Tyr Tyr Pro Asn Ser Val Lys Gly
1               5                   10                  15
Arg

<210> SEQ ID NO 167
<211> LENGTH: 18
<212> TYPE: PRT
<213> ORGANISM: murine

<400> SEQUENCE: 167

Gly Ile Asn Pro Glu Asn Asn Gly Gly Tyr Ser Tyr Asn Gln Lys Phe
1               5                   10                  15
```

```
<210> SEQ ID NO 168
<211> LENGTH: 18
<212> TYPE: PRT
<213> ORGANISM: murine

<400> SEQUENCE: 168

Gly Ile Asn Pro Glu Asn Thr Gly Gly Tyr Ser Tyr Asn Gln Lys Phe
1               5                   10                  15
Lys Gly

<210> SEQ ID NO 169
<211> LENGTH: 18
<212> TYPE: PRT
<213> ORGANISM: murine
<220> FEATURE:
<221> NAME/KEY: MISC_FEATURE
<222> LOCATION: (8)..(8)
<223> OTHER INFORMATION: Xaa = any amino acid
<220> FEATURE:
<221> NAME/KEY: MISC_FEATURE
<222> LOCATION: (10)..(10)
<223> OTHER INFORMATION: Xaa = any amino acid

<400> SEQUENCE: 169

Gly Ile Asn Pro Glu Asn Thr Xaa Gly Xaa Ala Tyr Asn Gln Lys Phe
1               5                   10                  15
Lys Gly

<210> SEQ ID NO 170
<211> LENGTH: 17
<212> TYPE: PRT
<213> ORGANISM: murine

<400> SEQUENCE: 170

Ala Ile Asp Thr Phe Asp Ser Asn Thr Lys Tyr Asn Gln Lys Phe Lys
1               5                   10                  15
Gly

<210> SEQ ID NO 171
<211> LENGTH: 17
<212> TYPE: PRT
<213> ORGANISM: murine

<400> SEQUENCE: 171

Ala Ile Asp Thr Phe Asp Ser Asn Thr Arg Tyr Asn Gln Lys Phe Lys
1               5                   10                  15
Gly

<210> SEQ ID NO 172
<211> LENGTH: 17
<212> TYPE: PRT
<213> ORGANISM: murine

<400> SEQUENCE: 172

Ala Ile Asp Thr Phe Asp Ser Asn Thr Arg Tyr Asn Pro Lys Phe Lys
1               5                   10                  15
Gly

<210> SEQ ID NO 173
<211> LENGTH: 17
<212> TYPE: PRT
<213> ORGANISM: murine
```

```
<400> SEQUENCE: 173

Thr Ile Asp Ala Ser Asp Arg Tyr Ile Ser Tyr Asn Gln Lys Phe Arg
1               5                   10                  15

Gly

<210> SEQ ID NO 174
<211> LENGTH: 17
<212> TYPE: PRT
<213> ORGANISM: murine

<400> SEQUENCE: 174

His Ile Asp Pro Tyr Tyr Gly Ser Ser Asn Tyr Asn Leu Lys Phe Lys
1               5                   10                  15

Gly

<210> SEQ ID NO 175
<211> LENGTH: 17
<212> TYPE: PRT
<213> ORGANISM: murine

<400> SEQUENCE: 175

Trp Ile Asp Pro Glu Asn Gly Gly Thr Glu Tyr Ala Pro Lys Phe Gln
1               5                   10                  15

Gly

<210> SEQ ID NO 176
<211> LENGTH: 17
<212> TYPE: PRT
<213> ORGANISM: murine

<400> SEQUENCE: 176

Tyr Ile Asn Pro Ser Ser Gly Tyr Thr Asn Tyr Asn Gln Lys Phe Lys
1               5                   10                  15

Asp

<210> SEQ ID NO 177
<211> LENGTH: 17
<212> TYPE: PRT
<213> ORGANISM: murine

<400> SEQUENCE: 177

Gly Ile Asn Pro Asn Thr Gly Ala Tyr Asn Tyr Asn Gln Lys Phe Lys
1               5                   10                  15

Gly

<210> SEQ ID NO 178
<211> LENGTH: 9
<212> TYPE: PRT
<213> ORGANISM: murine

<400> SEQUENCE: 178

Phe Asn Gly Tyr Tyr Ala Met Asp Tyr
1               5

<210> SEQ ID NO 179
<211> LENGTH: 9
<212> TYPE: PRT
<213> ORGANISM: murine

<400> SEQUENCE: 179

Phe Asn Gly Tyr Leu Ala Leu Asp Tyr
```

```
<210> SEQ ID NO 180
<211> LENGTH: 9
<212> TYPE: PRT
<213> ORGANISM: murine
<220> FEATURE:
<221> NAME/KEY: MISC_FEATURE
<222> LOCATION: (9)..(9)
<223> OTHER INFORMATION: Xaa = any amino acid

<400> SEQUENCE: 180

Phe Asn Gly Tyr Gln Ala Leu Asp Xaa
1               5

<210> SEQ ID NO 181
<211> LENGTH: 9
<212> TYPE: PRT
<213> ORGANISM: murine

<400> SEQUENCE: 181

Phe Asn Gly Tyr Gln Ala Leu Asp Gln
1               5

<210> SEQ ID NO 182
<211> LENGTH: 9
<212> TYPE: PRT
<213> ORGANISM: murine

<400> SEQUENCE: 182

Phe Asn Gly Tyr Leu Ala Leu Asp Gln
1               5

<210> SEQ ID NO 183
<211> LENGTH: 9
<212> TYPE: PRT
<213> ORGANISM: murine

<400> SEQUENCE: 183

Arg Asn Glu Tyr Tyr Thr Met Asp Tyr
1               5

<210> SEQ ID NO 184
<211> LENGTH: 9
<212> TYPE: PRT
<213> ORGANISM: murine

<400> SEQUENCE: 184

Arg Asn Glu Tyr Tyr Ile Met Asp Tyr
1               5

<210> SEQ ID NO 185
<211> LENGTH: 10
<212> TYPE: PRT
<213> ORGANISM: murine

<400> SEQUENCE: 185

Gly Gly Asp Asn Tyr Val Trp Phe Ala Tyr
1               5                   10

<210> SEQ ID NO 186
<211> LENGTH: 11
<212> TYPE: PRT
<213> ORGANISM: murine

<400> SEQUENCE: 186
```

```
Asn Gly Tyr Asp Asp Gly Val Pro Phe Asp Tyr
1               5                   10
```

<210> SEQ ID NO 187
<211> LENGTH: 12
<212> TYPE: PRT
<213> ORGANISM: murine

<400> SEQUENCE: 187

```
Arg Ser Asn Tyr Arg Tyr Asp Asp Ala Met Asp Tyr
1               5                   10
```

<210> SEQ ID NO 188
<211> LENGTH: 11
<212> TYPE: PRT
<213> ORGANISM: murine

<400> SEQUENCE: 188

```
Gly Asn Tyr Tyr Ser Gly Thr Ser Tyr Asp Tyr
1               5                   10
```

<210> SEQ ID NO 189
<211> LENGTH: 13
<212> TYPE: PRT
<213> ORGANISM: murine

<400> SEQUENCE: 189

```
Leu Tyr Gly Asn Tyr Asp Arg Tyr Tyr Ala Met Asp Tyr
1               5                   10
```

<210> SEQ ID NO 190
<211> LENGTH: 13
<212> TYPE: PRT
<213> ORGANISM: murine

<400> SEQUENCE: 190

```
Arg Gly Asp Tyr Tyr Arg Tyr Pro Tyr Ala Met Asp Tyr
1               5                   10
```

<210> SEQ ID NO 191
<211> LENGTH: 12
<212> TYPE: PRT
<213> ORGANISM: murine

<400> SEQUENCE: 191

```
Met Ile Thr Thr Gly Tyr His Tyr Ala Met Asp Tyr
1               5                   10
```

<210> SEQ ID NO 192
<211> LENGTH: 12
<212> TYPE: PRT
<213> ORGANISM: murine

<400> SEQUENCE: 192

```
Lys Ala Arg Gly Asp Ser Gly Ala Trp Phe Ala Tyr
1               5                   10
```

<210> SEQ ID NO 193
<211> LENGTH: 4
<212> TYPE: PRT
<213> ORGANISM: murine

<400> SEQUENCE: 193

```
Gly Val Asp Tyr
1
```

```
<210> SEQ ID NO 194
<211> LENGTH: 10
<212> TYPE: PRT
<213> ORGANISM: murine

<400> SEQUENCE: 194

Leu Glu Gly Ser Gly Tyr Gly Phe Ala Tyr
1               5                   10

<210> SEQ ID NO 195
<211> LENGTH: 8
<212> TYPE: PRT
<213> ORGANISM: murine

<400> SEQUENCE: 195

Ser Lys Arg Asp Tyr Phe Asp Tyr
1               5

<210> SEQ ID NO 196
<211> LENGTH: 11
<212> TYPE: PRT
<213> ORGANISM: murine

<400> SEQUENCE: 196

Cys Asn Phe Tyr Gly Asn Pro Tyr Phe Asp Tyr
1               5                   10

<210> SEQ ID NO 197
<211> LENGTH: 11
<212> TYPE: PRT
<213> ORGANISM: murine

<400> SEQUENCE: 197

Cys Asn Phe Tyr Ala Asn Pro Tyr Phe Asp Tyr
1               5                   10

<210> SEQ ID NO 198
<211> LENGTH: 12
<212> TYPE: PRT
<213> ORGANISM: murine

<400> SEQUENCE: 198

Arg Pro Met Ile Thr Ala Gly Ala Trp Phe Ala Tyr
1               5                   10

<210> SEQ ID NO 199
<211> LENGTH: 13
<212> TYPE: PRT
<213> ORGANISM: murine

<400> SEQUENCE: 199

Ile Thr Thr Val Val Gly Tyr Tyr Tyr Ala Met Asp Tyr
1               5                   10

<210> SEQ ID NO 200
<211> LENGTH: 120
<212> TYPE: PRT
<213> ORGANISM: murine

<400> SEQUENCE: 200

Leu Glu Val Lys Leu Val Glu Ser Gly Gly Gly Leu Val Lys Pro Gly
1               5                   10                  15
Gly Ser Leu Lys Leu Ser Cys Ala Ala Ser Gly Phe Thr Phe Ser Gly
            20                  25                  30
```

```
Phe Ala Met Ser Trp Val Arg Gln Thr Pro Glu Lys Arg Leu Glu Trp
         35                  40                  45

Val Ala Ser Ile Ser Ser Gly Gly Thr Thr Tyr Tyr Leu Asp Ser Val
     50                  55                  60

Lys Gly Arg Phe Thr Ile Ser Arg Asp Ile Ala Arg Asn Ile Leu Tyr
 65                  70                  75                  80

Leu Gln Met Ser Ser Leu Arg Ser Glu Asp Thr Ala Met Tyr Tyr Cys
                 85                  90                  95

Ala Arg Gly Asn Tyr Tyr Ser Gly Thr Ser Tyr Asp Tyr Trp Gly Gln
            100                 105                 110

Gly Thr Thr Leu Thr Val Ser Ser
        115                 120

<210> SEQ ID NO 201
<211> LENGTH: 123
<212> TYPE: PRT
<213> ORGANISM: murine

<400> SEQUENCE: 201

Leu Glu Val Gln Leu Gln Gln Ser Gly Ala Glu Leu Val Arg Ser Gly
 1               5                  10                  15

Ala Ser Val Lys Leu Ser Cys Thr Ala Ser Gly Phe Asn Ile Lys Asp
             20                  25                  30

Tyr Tyr Met His Trp Val Lys Gln Arg Pro Glu Gln Gly Leu Glu Trp
         35                  40                  45

Ile Gly Trp Ile Asp Pro Glu Asn Gly Asp Thr Lys Tyr Ala Pro Lys
     50                  55                  60

Phe Gln Gly Lys Ala Thr Met Thr Ala Asp Thr Ser Ser Asn Thr Ala
 65                  70                  75                  80

Tyr Leu Gln Leu Ser Ser Leu Thr Ser Glu Asp Thr Ala Val Tyr Tyr
                 85                  90                  95

Cys Asn Ala Lys Asn Tyr Tyr Val Ser Asn Tyr Asn Phe Phe Asp Val
            100                 105                 110

Trp Gly Ala Gly Thr Thr Val Thr Val Ser Ser
        115                 120

<210> SEQ ID NO 202
<211> LENGTH: 123
<212> TYPE: PRT
<213> ORGANISM: murine

<400> SEQUENCE: 202

Leu Glu Val Gln Leu Gln Gln Pro Gly Ala Glu Leu Val Arg Ser Gly
 1               5                  10                  15

Ala Ser Val Lys Leu Ser Cys Lys Ala Ser Gly Phe Asn Ile Lys Asp
             20                  25                  30

Tyr Tyr Ile His Trp Val Lys Gln Arg Pro Glu Gln Gly Leu Glu Trp
         35                  40                  45

Ile Gly Trp Ile Asp Pro Glu Ile Gly Ala Thr Lys Tyr Val Pro Lys
     50                  55                  60

Phe Gln Gly Lys Ala Thr Met Thr Thr Asp Thr Ser Ser Asn Thr Ala
 65                  70                  75                  80

Tyr Leu Gln Leu Ser Ser Leu Thr Ser Glu Asp Thr Ala Val Tyr Tyr
                 85                  90                  95

Cys Asn Ala Leu Tyr Gly Asn Tyr Asp Arg Tyr Tyr Ala Met Asp Tyr
            100                 105                 110

Trp Gly Gln Gly Thr Ser Val Thr Val Ser Ser
```

```
                   115                 120

<210> SEQ ID NO 203
<211> LENGTH: 118
<212> TYPE: PRT
<213> ORGANISM: murine

<400> SEQUENCE: 203

Leu Glu Val Gln Leu Gln Gln Ser Gly Pro Glu Leu Val Lys Pro Gly
1               5                   10                  15

Ala Ser Leu Lys Met Ser Cys Lys Ala Ser Gly Tyr Ser Phe Thr Asp
            20                  25                  30

Tyr Ile Ile Leu Trp Val Lys Gln Asn His Gly Lys Ser Leu Glu Trp
        35                  40                  45

Ile Gly His Ile Asp Pro Tyr Tyr Gly Ser Ser Asn Tyr Asn Leu Lys
    50                  55                  60

Phe Lys Gly Lys Ala Thr Leu Thr Val Asp Lys Ser Ser Ser Thr Ala
65                  70                  75                  80

Tyr Met Gln Leu Asn Ser Leu Thr Ser Glu Asp Ser Ala Val Tyr Tyr
                85                  90                  95

Cys Gly Arg Ser Lys Arg Asp Tyr Phe Asp Tyr Trp Gly Gln Gly Thr
            100                 105                 110

Thr Leu Thr Val Ser Ser
        115

<210> SEQ ID NO 204
<211> LENGTH: 122
<212> TYPE: PRT
<213> ORGANISM: murine

<400> SEQUENCE: 204

Leu Glu Val Gln Leu Gln Gln Ser Gly Pro Glu Leu Val Lys Pro Gly
1               5                   10                  15

Ala Ser Val Lys Ile Ser Cys Lys Thr Ser Gly Tyr Thr Phe Thr Glu
            20                  25                  30

Tyr Thr Met His Trp Val Lys Gln Ser His Gly Lys Ser Leu Glu Trp
        35                  40                  45

Ile Gly Gly Val Asn Pro Asn Asn Gly Gly Ala Leu Tyr Asn Gln Lys
    50                  55                  60

Phe Lys Gly Lys Ala Thr Leu Thr Val Asp Lys Ser Ser Ser Thr Ala
65                  70                  75                  80

Tyr Met Glu Leu Arg Ser Leu Ala Ser Glu Asp Ser Ala Val Tyr Tyr
                85                  90                  95

Cys Ala Arg Arg Ser Asn Tyr Arg Tyr Asp Asp Ala Met Asp Tyr Trp
            100                 105                 110

Gly Gln Gly Thr Ser Val Thr Val Ser Ser
        115                 120

<210> SEQ ID NO 205
<211> LENGTH: 119
<212> TYPE: PRT
<213> ORGANISM: murine

<400> SEQUENCE: 205

Leu Glu Val Gln Leu Gln Gln Ser Gly Ala Glu Leu Val Arg Ser Gly
1               5                   10                  15

Ala Ser Val Lys Leu Ser Cys Thr Ala Ser Ala Phe Asn Ile Lys Asp
            20                  25                  30
```

-continued

His Tyr Met His Trp Val Lys Gln Arg Pro Glu Gln Gly Leu Glu Trp
            35                  40                  45

Ile Gly Trp Ile Asp Pro Glu Ser Gly Asp Thr Glu Tyr Ala Pro Lys
 50                  55                  60

Phe Gln Gly Lys Ala Thr Met Thr Ala Asp Ile Ser Ser Asn Thr Ala
 65                  70                  75                  80

Tyr Leu Gln Leu Asn Ser Leu Thr Ser Glu Asp Thr Ala Val Tyr Tyr
                85                  90                  95

Cys Asn Ala Phe Asn Gly Tyr Gln Ala Leu Asp Gln Trp Gly Gln Gly
            100                 105                 110

Thr Ser Val Thr Val Ser Ser
            115

<210> SEQ ID NO 206
<211> LENGTH: 114
<212> TYPE: PRT
<213> ORGANISM: murine

<400> SEQUENCE: 206

Ser Arg Asp Ile Val Leu Thr Gln Ser Pro Ala Ser Leu Ala Val Ser
 1               5                  10                  15

Leu Gly Gln Arg Ala Thr Ile Ser Cys Arg Ala Ser Glu Ser Val Asp
             20                  25                  30

Ser Tyr Gly Asn Ser Phe Met His Trp Tyr Gln Gln Lys Pro Gly Gln
            35                  40                  45

Pro Pro Lys Leu Leu Ile Tyr Arg Ala Ser Asn Leu Glu Ser Gly Ile
 50                  55                  60

Pro Ala Arg Phe Ser Gly Ser Gly Ser Arg Thr Asp Phe Thr Leu Thr
 65                  70                  75                  80

Ile Asn Pro Val Glu Ala Asp Asp Val Ala Thr Tyr Tyr Cys Gln Gln
                85                  90                  95

Ser Asn Glu Asp Pro Arg Thr Phe Gly Gly Gly Thr Lys Leu Glu Ile
            100                 105                 110

Lys Arg

<210> SEQ ID NO 207
<211> LENGTH: 109
<212> TYPE: PRT
<213> ORGANISM: murine

<400> SEQUENCE: 207

Ser Arg Glu Ile Val Leu Thr Gln Ser Pro Ala Thr Met Ser Ala Ser
 1               5                  10                  15

Pro Gly Glu Lys Val Thr Met Thr Cys Ser Ala Ser Ser Ser Val Arg
             20                  25                  30

Tyr Met Tyr Trp Tyr Gln Gln Lys Ser Ser Thr Ser Pro Lys Leu Trp
            35                  40                  45

Ile Tyr Asp Thr Ser Lys Leu Ala Ser Gly Val Pro Gly Arg Phe Ser
 50                  55                  60

Gly Ser Gly Ser Gly Asn Ser Tyr Ser Leu Thr Ile Ser Ser Met Glu
 65                  70                  75                  80

Ala Glu Asp Val Ala Thr Tyr Tyr Cys Phe Gln Gly Ser Gly Tyr Pro
                85                  90                  95

Leu Thr Phe Gly Ser Gly Thr Lys Leu Glu Ile Lys Arg
            100                 105

<210> SEQ ID NO 208

```
<211> LENGTH: 110
<212> TYPE: PRT
<213> ORGANISM: murine

<400> SEQUENCE: 208

Ser Arg Asp Ile Val Met Thr Gln Ser Gln Lys Phe Met Ser Thr Ser
1               5                   10                  15

Val Gly Asp Arg Val Ser Ile Thr Cys Lys Ala Ser Gln Asn Val Arg
            20                  25                  30

Thr Ala Val Ala Trp Tyr Gln Gln Lys Pro Gly Gln Ser Pro Lys Ala
        35                  40                  45

Leu Ile Tyr Leu Ala Ser Asn Arg His Thr Gly Val Pro Asp Arg Phe
    50                  55                  60

Thr Gly Ser Gly Ser Gly Thr Asp Phe Thr Leu Thr Ile Ser Asn Val
65                  70                  75                  80

Gln Ser Glu Asp Leu Ala Asp Tyr Phe Cys Leu Gln His Trp Asn Tyr
                85                  90                  95

Pro Leu Thr Phe Gly Ala Gly Thr Lys Leu Glu Leu Lys Arg
            100                 105                 110

<210> SEQ ID NO 209
<211> LENGTH: 110
<212> TYPE: PRT
<213> ORGANISM: murine

<400> SEQUENCE: 209

Ser Arg Asp Ile Gln Met Thr Gln Ser Pro Ser Ser Met Tyr Ala Ser
1               5                   10                  15

Leu Gly Glu Arg Val Thr Ile Thr Cys Lys Ala Ser Gln Asp Ile Asn
            20                  25                  30

Ser Tyr Leu Ser Trp Phe Gln Gln Lys Pro Gly Lys Ser Pro Lys Thr
        35                  40                  45

Leu Ile Tyr Arg Ala Asn Arg Leu Val Asp Gly Val Pro Ser Arg Phe
    50                  55                  60

Ser Gly Ser Gly Ser Gly Gln Asp Tyr Ser Leu Thr Ile Ser Ser Leu
65                  70                  75                  80

Glu Tyr Glu Asp Met Gly Ile Tyr Tyr Cys Leu Gln Tyr Asp Glu Phe
                85                  90                  95

Pro Tyr Thr Phe Gly Gly Gly Thr Lys Leu Glu Ile Lys Arg
            100                 105                 110

<210> SEQ ID NO 210
<211> LENGTH: 115
<212> TYPE: PRT
<213> ORGANISM: murine

<400> SEQUENCE: 210

Ser Arg Asp Val Val Met Thr Gln Thr Pro Leu Thr Leu Ser Val Thr
1               5                   10                  15

Ile Gly Gln Pro Ala Ser Ile Ser Cys Lys Ser Ser Gln Ser Leu Leu
            20                  25                  30

Asp Ile Asp Glu Lys Thr Tyr Leu Asn Trp Phe Leu Gln Arg Pro Gly
        35                  40                  45

Gln Ser Pro Lys Arg Leu Ile Tyr Leu Val Ser Lys Leu Asp Ser Gly
    50                  55                  60

Val Pro Asp Arg Phe Thr Gly Ser Gly Ser Gly Thr Asp Phe Thr Leu
65                  70                  75                  80

Lys Ile Ser Arg Val Glu Ala Glu Asp Leu Gly Val Tyr Tyr Cys Trp
```

-continued

```
                    85                  90                  95
Gln Gly Thr His Phe Pro Gln Thr Phe Gly Gly Gly Thr Lys Leu Glu
            100                 105                 110

Ile Lys Arg
        115

<210> SEQ ID NO 211
<211> LENGTH: 113
<212> TYPE: PRT
<213> ORGANISM: murine

<400> SEQUENCE: 211

Ser Arg Glu Ile Val Leu Thr Gln Ser Pro Ala Ile Met Ser Ala Ser
1               5                   10                  15

Leu Gly Glu Arg Val Thr Met Thr Cys Thr Ala Ser Ser Ser Val Ser
            20                  25                  30

Ser Ser Tyr Leu His Trp Tyr Gln Gln Lys Pro Gly Ser Ser Pro Lys
        35                  40                  45

Leu Trp Ile Tyr Ser Thr Ser Asn Leu Ala Ser Gly Val Pro Ala Arg
    50                  55                  60

Phe Ser Gly Ser Gly Ser Gly Thr Ser Tyr Ser Leu Thr Ile Ser Ser
65                  70                  75                  80

Met Glu Ala Glu Asp Ala Ala Thr Tyr Tyr Cys Arg Gln Tyr His Arg
                85                  90                  95

Ser Pro Pro Ile Phe Thr Phe Gly Ser Gly Thr Lys Leu Glu Ile Lys
            100                 105                 110

Arg
```

POLYPEPTIDES AND ANTIBODIES DERIVED FROM CHRONIC LYMPHOCYTIC LEUKEMIA CELLS AND USES THEREOF

RELATED APPLICATIONS

This application is a divisional of U.S. application Ser. No. 12/221,122, filed Jul. 30, 2008 (now U.S. Pat. No. 7,714,110), which is a divisional of U.S. application Ser. No. 10/996,316, filed Nov. 23, 2004 (now U.S. Pat. No. 7,408,041), which is a continuation in part of U.S. application Ser. No. 10/894,672, filed Jul. 20, 2004, which is a continuation in part of U.S. application Ser. No. 10/736,188, filed Dec. 15, 2003 (now abandoned), which is a continuation in part of U.S. application Ser. No. 10/379,151, filed on Mar. 4, 2003 (now U.S. Pat. No. 7,435,412), which, is a continuation in part of PCT/US01/47931, filed on Dec. 10, 2001, which is an international application that claims the benefit of U.S. Provisional Application No. 60/254,113 filed Dec. 8, 2000. The specifications of each of the foregoing applications are incorporated herein by reference in their entirety.

TECHNICAL FIELD

Cancer treatments using a therapy that provides a combination of two mechanisms are disclosed. More specifically, this disclosure relates to treating cancer using a therapy that: 1) interferes with the interaction between CD200 and its receptor to block immune suppression thereby promoting eradication of the cancer cells; and 2) directly kills the cancer cells either by a) complement-mediated or antibody-dependent cellular cytotoxicity or b) by targeting cells using a fusion molecule that includes a CD200-targeting portion.

BACKGROUND

Chronic Lymphocytic Leukemia (CLL) is a disease of the white blood cells and is the most common form of leukemia in the Western Hemisphere. CLL represents a diverse group of diseases relating to the growth of malignant lymphocytes that grow slowly but have an extended life span. CLL is classified in various categories that include, for example, B-cell chronic lymphocytic leukemia (B-CLL) of classical and mixed types, B-cell and T-cell prolymphocytic leukemia, hairy cell leukemia, and large granular lymphocytic leukemia.

Of all the different types of CLL, B-CLL accounts for approximately 30 percent of all leukemias. Although it occurs more frequently in individuals over 50 years of age, it is increasingly seen in younger people. B-CLL is characterized by accumulation of B-lymphocytes that are morphologically normal but biologically immature, leading to a loss of function. Lymphocytes normally function to fight infection. In B-CLL, however, lymphocytes accumulate in the blood and bone marrow and cause swelling of the lymph nodes. The production of normal bone marrow and blood cells is reduced and patients often experience severe anemia as well as low platelet counts. This can pose the risk of life-threatening bleeding and the development of serious infections because of reduced numbers of white blood cells.

To further understand diseases such as leukemia it is important to have suitable cell lines that can be used as tools for research on their etiology, pathogenesis and biology. Examples of malignant human B-lymphoid cell lines include pre-B acute lymphoblasticleukemia (Reh), diffuse large cell lymphoma (WSU-DLCL2), and Waldenstrom's macroglobulinemia (WSU-WM). Unfortunately, many of the existing cell lines do not represent the clinically most common types of leukemia and lymphoma.

The use of Epstein Barr Virus (EBV) infection in vitro has resulted in some CLL derived cell lines, in particular B-CLL cells lines, that are representative of the malignant cells. The phenotype of these cell lines is different than that of the in vivo tumors and instead the features of B-CLL lines tend to be similar to those of Lymphoblastoid cell lines. Attempts to immortalize B-CLL cells with the aid of EBV infection have had little success. The reasons for this are unclear but it is known that it is not due to a lack of EBV receptor expression, binding or uptake. Wells et al. found that B-CLL cells were arrested in the G1/S phase of the cell cycle and that transformation associated EBV DNA was not expressed. This suggests that the interaction of EBV with B-CLL cells is different from that with normal B cells. EBV-transformed CLL cell lines moreover appear to differentiate, possessing a morphology more similar to lymphoblastoid cell lines (LCL) immortalized by EBV.

An EBV-negative CLL cell line, WSU-CLL, has been established previously (Mohammad et al., (1996) Leukemia 10(1):130-7). However, no other such cell lines are known.

Various mechanisms play a role in the body's response to a disease state, including cancer and CLL. For example, CD4+ T helper cells play a crucial role in an effective immune response against various malignancies by providing stimulatory factors to effector cells. Cytotoxic T cells are believed to be the most effective cells to eliminate cancer cells, and T helper cells prime cytotoxic T cells by secreting Th1 cytokines such as IL-2 and IFN-γ. In various malignancies, T helper cells have been shown to have an altered phenotype compared to cells found in healthy individuals. One of the prominent altered features is decreased Th1 cytokine production and a shift to the production of Th2 cytokines. (See, e.g., Kiani, et al., Haematologica 88:754-761 (2003); Maggio, et al., Ann Oncol 13 Suppl 1:52-56 (2002); Ito, et al., Cancer 85:2359-2367 (1999); Podhorecka, et al., Leuk Res 26:657-660 (2002); Tatsumi, et al., J Exp Med 196:619-628 (2002); Agarwal, et al., Immunol Invest 32:17-30 (2003); Smyth, et al., Ann Surg Oncol 10:455-462 (2003); Contasta, et al., Cancer Biother Radiopharm 18:549-557 (2003); Lauerova, et al., Neoplasma 49:159-166 (2002).) Reversing that cytokine shift to a Th1 profile has been demonstrated to augment anti-tumor effects of T cells. (See Winter, et al., Immunology 108:409-419 (2003); Inagawa, et al., Anticancer Res 18:3957-3964 (1998).)

Mechanisms underlying the capacity of tumor cells to drive the cytokine expression of T helper cells from Th1 to Th2 include the secretion of cytokines such as IL-10 or TGF-β as well as the expression of surface molecules interacting with cells of the immune system. OX-2/CD200, a molecule expressed on the surface of dendritic cells which possesses a high degree of homology to molecules of the immunoglobulin gene family, has been implicated in immune suppression (Gorczynski et al., Transplantation 65:1106-1114 (1998)) and evidence that OX-2/CD200-expressing cells can inhibit the stimulation of Th1 cytokine production has been provided. Gorczynski et al. demonstrated in a mouse model that infusion of OX-2/CD200 Fc suppresses the rejection of tumor cells in an animal model using leukaemic tumor cells (Clin Exp Immunol 126:220-229 (2001)).

Improved methods for treating individuals suffering from cancer or CLL are desirable, especially to the extent they can enhance the activity of T cells.

SUMMARY

In one embodiment a CLL cell line of malignant origin is provided that is not established by immortalisation with EBV. The cell line, which was derived from primary CLL cells, is deposited under ATCC accession no. PTA-3920. In a preferred embodiment, the cell line is CLL-AAT. CLL-AAT is B-CLL cell line, derived from a B-CLL primary cell.

In a further aspect, the CLL-AAT cell line is used to generate monoclonal antibodies useful in the diagnosis and/or treatment of CLL. Antibodies may be generated by using the cells as disclosed herein as immunogens, thus raising an immune response in animals from which monoclonal antibodies may be isolated. The sequence of such antibodies may be determined and the antibodies or variants thereof produced by recombinant techniques. In this aspect, "variants" includes chimeric, CDR-grafted, humanized and fully human antibodies based on the sequence of the monoclonal antibodies.

Moreover, antibodies derived from recombinant libraries ("phage antibodies") may be selected using the cells described herein, or polypeptides derived therefrom, as bait to isolate the antibodies on the basis of target specificity.

In a still further aspect, antibodies may be generated by panning antibody libraries using primary CLL cells, or antigens derived therefrom, and further screened and/or characterized using a CLL cell line, such as, for example, the CLL cell line described herein. Accordingly, a method for characterizing an antibody specific for CLL is provided, which includes assessing the binding of the antibody to a CLL cell line.

In a further aspect, there is provided a method for identifying proteins uniquely expressed in CLL cells employing the CLL-AAT cell line, by methods well known to those, skilled with art, such as by immunoprecipitation followed by mass spectroscopy analyses. Such proteins may be uniquely expressed in the CLL-AAT cell line, or in primary cells derived from CLL patients.

Small molecule libraries (many available commercially) may be screened using the CLL-AAT cell line in a cell-based assay to identify agents capable of modulating the growth characteristics of the cells. For example, the agents may be identified which modulate apoptosis in the CLL-AAT cell line, or which inhibit growth and/or proliferation thereof. Such agents are candidates for the development of therapeutic compounds.

Nucleic acids isolated from CLL-AAT cell lines may be used in subtractive hybridization experiments to identify CLL-specific genes or in micro array analyses (e.g., gene chip experiments). Genes whose transcription is modulated in CLL cells may be identified. Polypeptide or nucleic acid gene products identified in this manner are useful as leads for the development of antibody or small molecule therapies for CLL.

In a preferred aspect, the CLL-AAT cell line may be used to identify internalizing antibodies, which bind to cell surface components which are internalized by the cell. Such antibodies are candidates for therapeutic use. In particular, single-chain antibodies, which remain stable in the cytoplasm and which retain intracellular binding activity, may be screened in this manner.

In yet another aspect, a therapeutic treatment is described in which a patient is screened for the presence of a polypeptide that is upregulated by a malignant cancer cell and an antibody that interferes with the metabolic pathway of the upregulated polypeptide is administered to the patient.

The present disclosure further is directed to methods wherein a determination is made as to whether OX-2/CD200 is upregulated in a subject and, if so, administering to the subject a therapy that enhances immune response. Upregulation of OX2/CD200 can be determined by measuring OX2/CD200 levels directly, or by monitoring the level of any marker that correlates with OX2/CD200. Suitable immunomodulatory therapies include the administration of agents that block negative regulation of T cells or antigen presenting cells, administration of agents that enhance positive co-stimulation of T cells, cancer vaccines, general adjuvants stimulating the immune system or treatment with cytokines such as IL-2, GM-CSF and IFN-gamma. In particularly useful embodiments, the therapy that enhances immune response includes the administration of a polypeptide that binds to OX-2/CD200, optionally in combination with one or more other immunomodulatory therapies. In another embodiment, the polypeptide binds to an OX-2/CD200 receptor.

In another aspect; methods in accordance with this disclosure are used to treat a disease state in which OX-2/CD200 is upregulated in a subject by administering a polypeptide that binds to OX-2/CD200 or an OX-2/CD200 receptor to the subject afflicted with the disease state. In one embodiment, the disease state treated by these methods includes cancer, specifically, in other embodiments, CLL.

In a particularly useful embodiment, a cancer therapy in accordance with this disclosure includes i) administering an antibody that interferes with the interaction between CD200 and its receptor to block immune suppression, thereby promoting eradication of the cancer cells; and ii) administering a fusion molecule that includes a CD200-targeting portion to directly kill cancer cells. Alternatively, the antibody directly kills the cancer cells through complement-mediated or antibody-dependent cellular cytotoxicity.

In another embodiment in accordance with the present disclosure, methods are provided for monitoring the progress of a therapeutic treatment. The method involves administering a immunomodulatory therapy and determining OX-2/CD200 levels in a subject at least twice to determine the effectiveness of the therapy.

BRIEF DESCRIPTION OF THE FIGURES

FIGS. 3a and 3b show the results of whole cell ELISA comparing binding of selected scFv antibodies to primary B-CLL cells and normal primary human B cells. Anti-CD19 antibody was used as a positive control to verify that equal numbers of B-CLL and normal B cells were plated in each well. Other controls were as described in the legend to FIG. 2.

FIG. 7 shows the binding specificity of scFv antibodies in accordance with this disclosure as analyzed by 3-color flow cytometry. In normal peripheral blood mononuclear cells, the antigen recognized by scFv-9 is moderately expressed on B lymphocytes and weakly expressed on a subpopulation of T lymphocytes. PBMC from a normal donor were analyzed by 3-color flow cytometry using anti-CD5-FITC, anti-CD19-PerCP, and scFv-9/Anti-HA-biotin/streptavidin-PE.

FIGS. 9A, 9B and 9C provide a summary of CDR sequences and binding specificities of selected scFv antibodies.

FIG. 10 is Table 2 which shows a summary of flow cytometry results comparing expression levels of scFv antigens on primary CLL cells vs. normal PBMC as described in FIGS. 8a-8c.

FIG. 11 is a Table showing a summary of flow cytometry results comparing expression levels of scFv-9 antigen with the percentage of CD38+ cells in peripheral blood mononuclear cells isolated from ten CLL patients.

FIG. 13 shows that three scFv antibodies bind specifically to 293-EBNA cells transiently transfected with a human OX-2/CD200 cDNA clone. A OX-2/CD200 cDNA was cloned from CLL cells by RT-PCR and inserted into the mammalian expression vector pCEP4 (Invitrogen). PCEP4-CD200 plasmid or the corresponding empty vector pCEP4 was transfected into 293-EBNA cells using Polyfect reagent (QIAGEN). Two days after transfection, the cells were analyzed for binding to scFv antibodies by flow cytometry.

FIG. 18 shows the results of statistical analyses performed using 2 parametric tests (Student's t-test and Welch's test) and one non-parametric test, the Wilcox test.

FIG. 21A shows deduced amino acid sequence of heavy chain complementarity regions of CD200-specific clones.

FIG. 21B shows deduced amino acid sequence of heavy chain complementarity regions of CD200-specific clones.

FIG. 23 shows deduced amino acid sequences of selected CD200 Fabs for chimerization.

DETAILED DESCRIPTION

Figure 1:
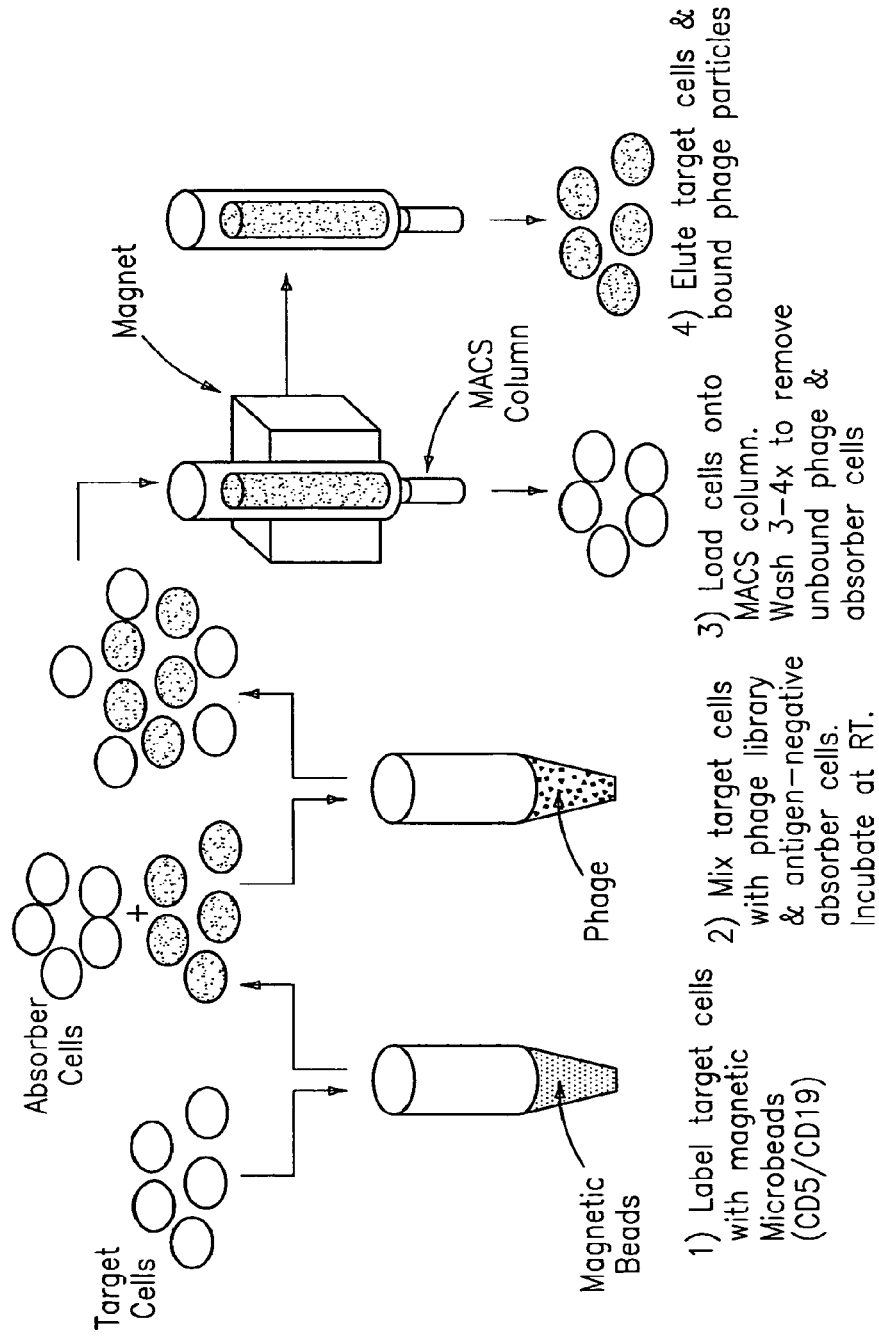
FIG. 1 schematically illustrates typical steps involved in cell surface panning of antibody libraries by magnetically-activated cell sorting (MACS).
Figure 2:
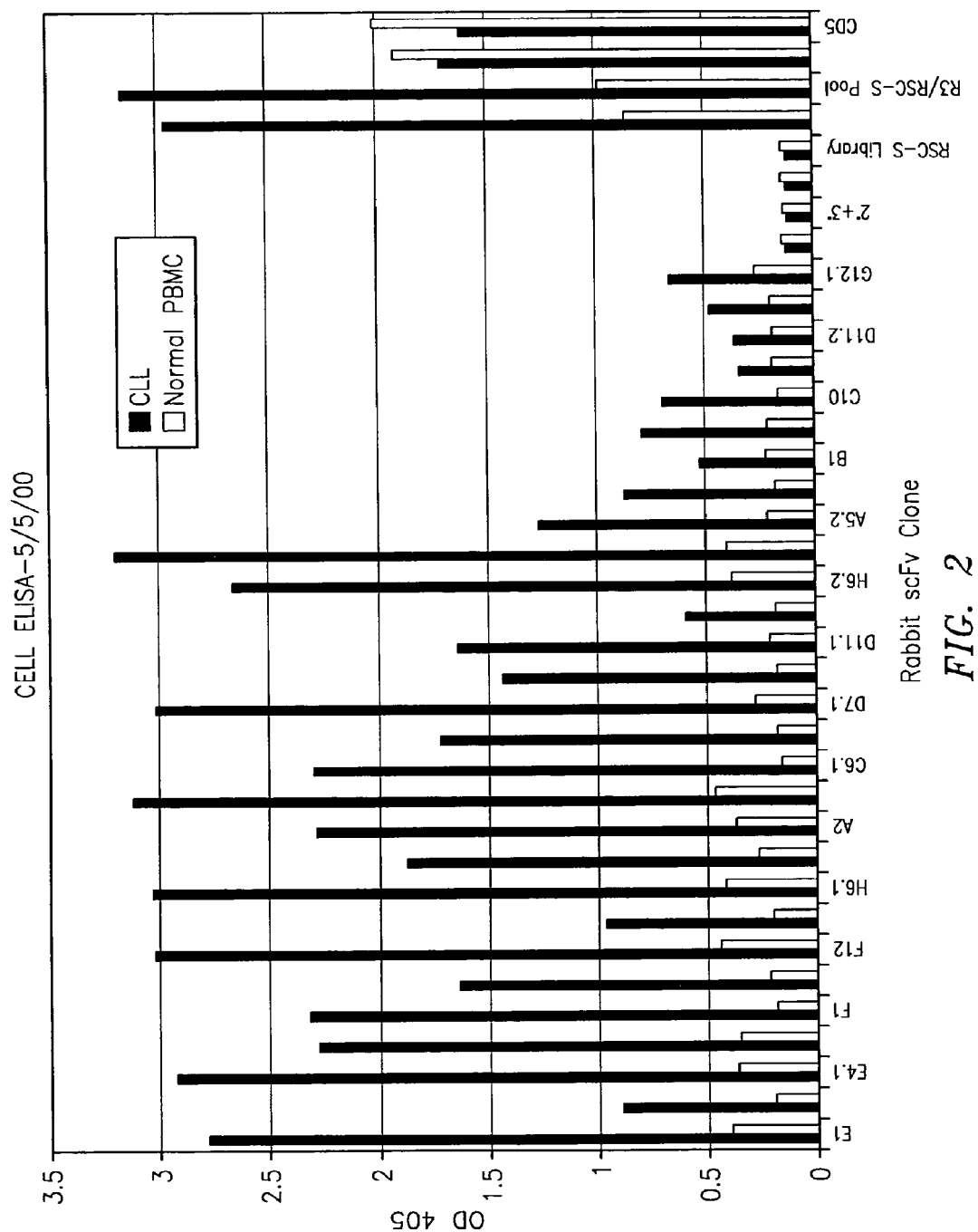
FIG. 2 is a graph showing the results of whole cell ELISA demonstrating binding of selected scFv clones to primary B-CLL cells and absence of binding to normal human PBMC. The designation 2°+3° in this and other figures refers to negative control wells stained with Mouse Anti-HA and detecting antimouse antibodies alone. The designation RSC-S Library in this and other figures refers to soluble antibodies prepared from original rabbit scFv unpanned library. The designation R3/RSC-S Pool in this and other figures refers to soluble antibodies prepared from entire pool of scFv antibodies from round 3 of panning. Anti-CD5 antibody was used as a positive control to verify that equal numbers of B-CLL and PBMC cells were plated in each well.
Figure 3B:
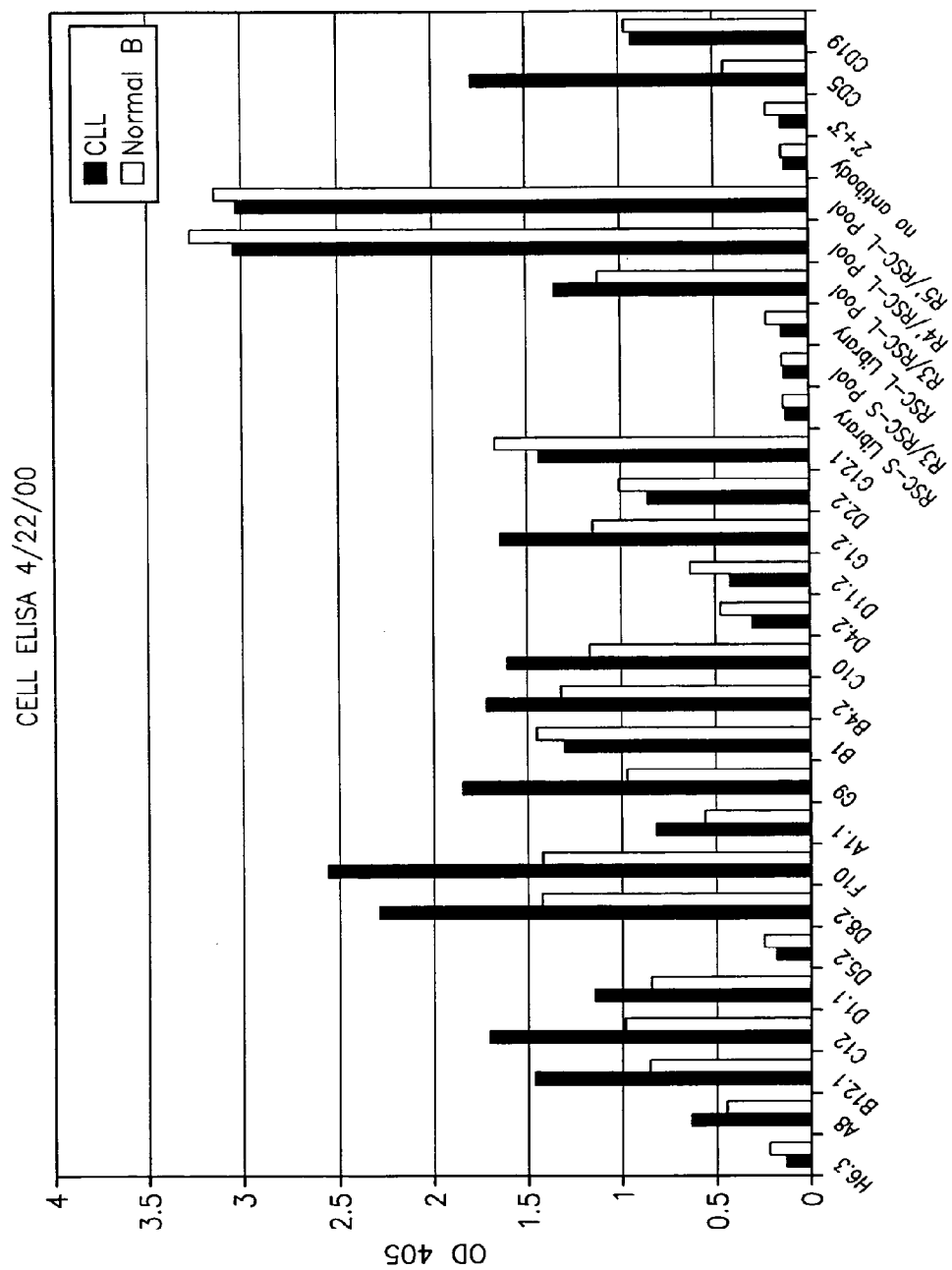
Figure 4A:
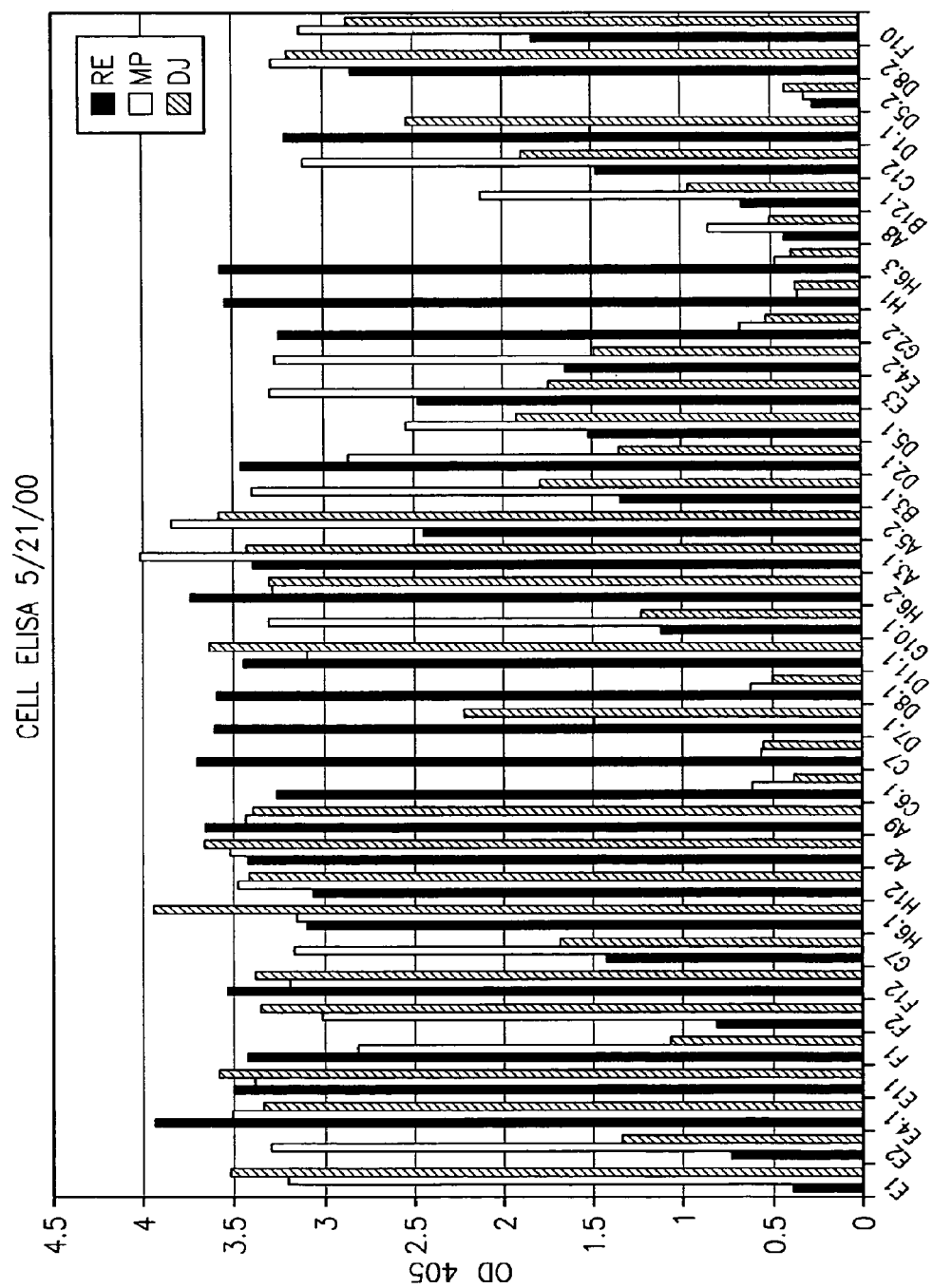
FIGS. 4a and 4b show the results of whole cell ELISA used to determine if scFv clones bind to patient-specific (i.e. idiotype) or blood type-specific (i.e. HLA) antigens. Each clone was tested for binding to PBMC isolated from 3 different B-CLL patients. Clones that bound to (1 patient sample were considered to be patient or blood type-specific.
Figure 4B:
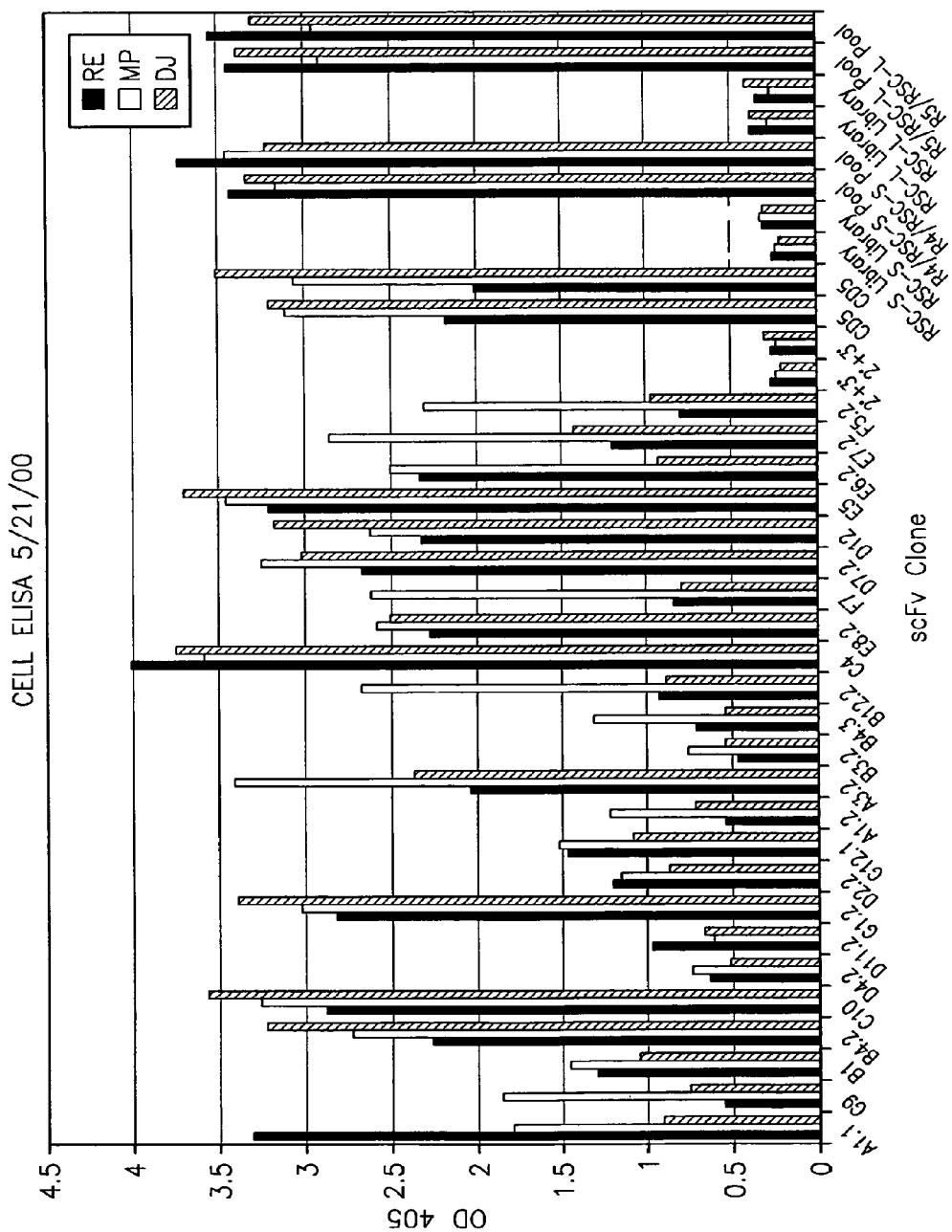
Figure 5A:
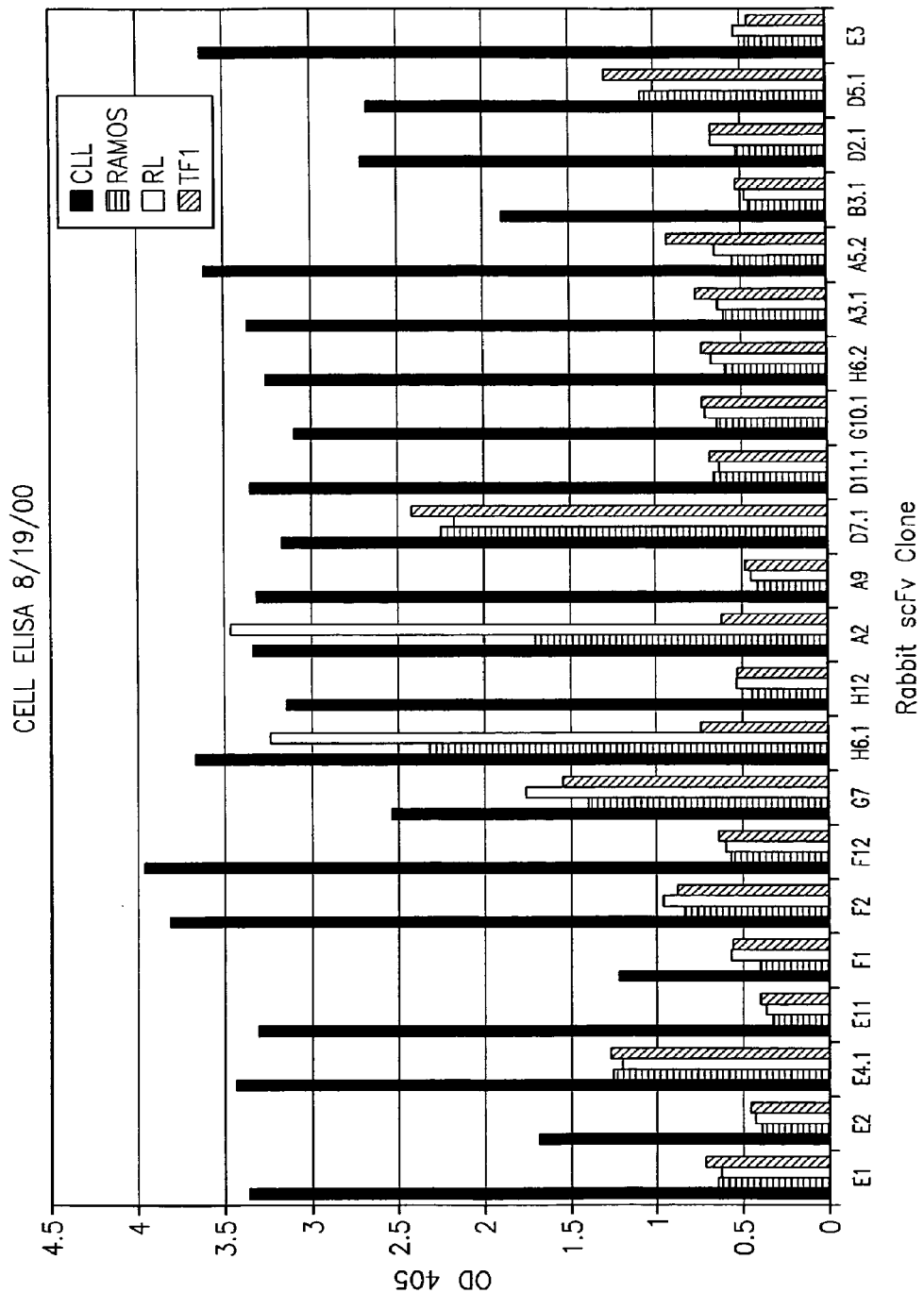
FIGS. 5a and 5b show the results of whole cell ELISA comparing binding of scFv clones to primary B-CLL cells and three human leukemic cell lines. Ramos is a mature B cell line derived from a Burkitt's lymphoma. RL is a mature B cell line derived from a non-Hodgkin's lymphoma. TF-1 is an erythroblastoid cell line derived from a erythroleukemia.
Figure 5B:
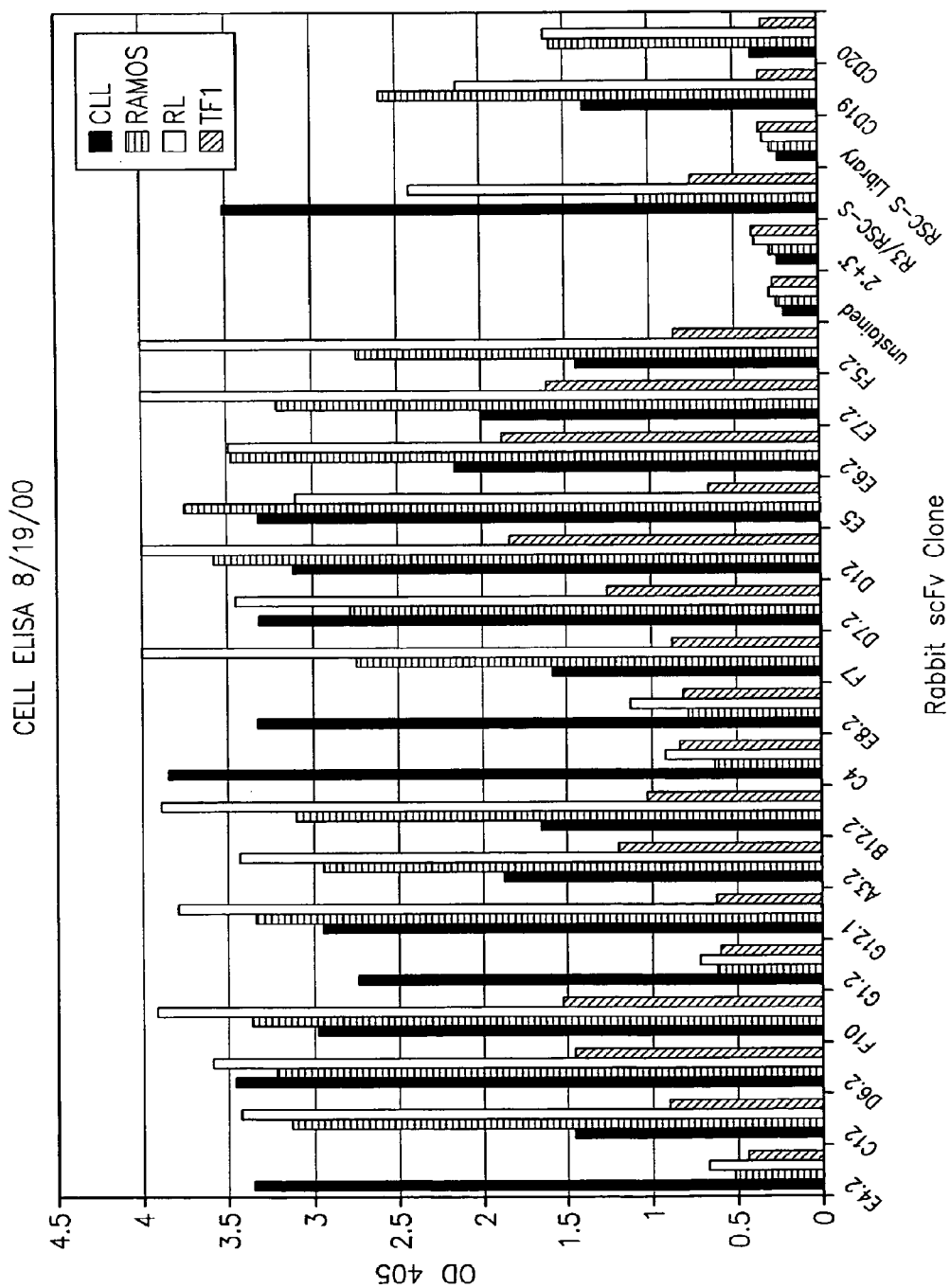
Figure 6A:
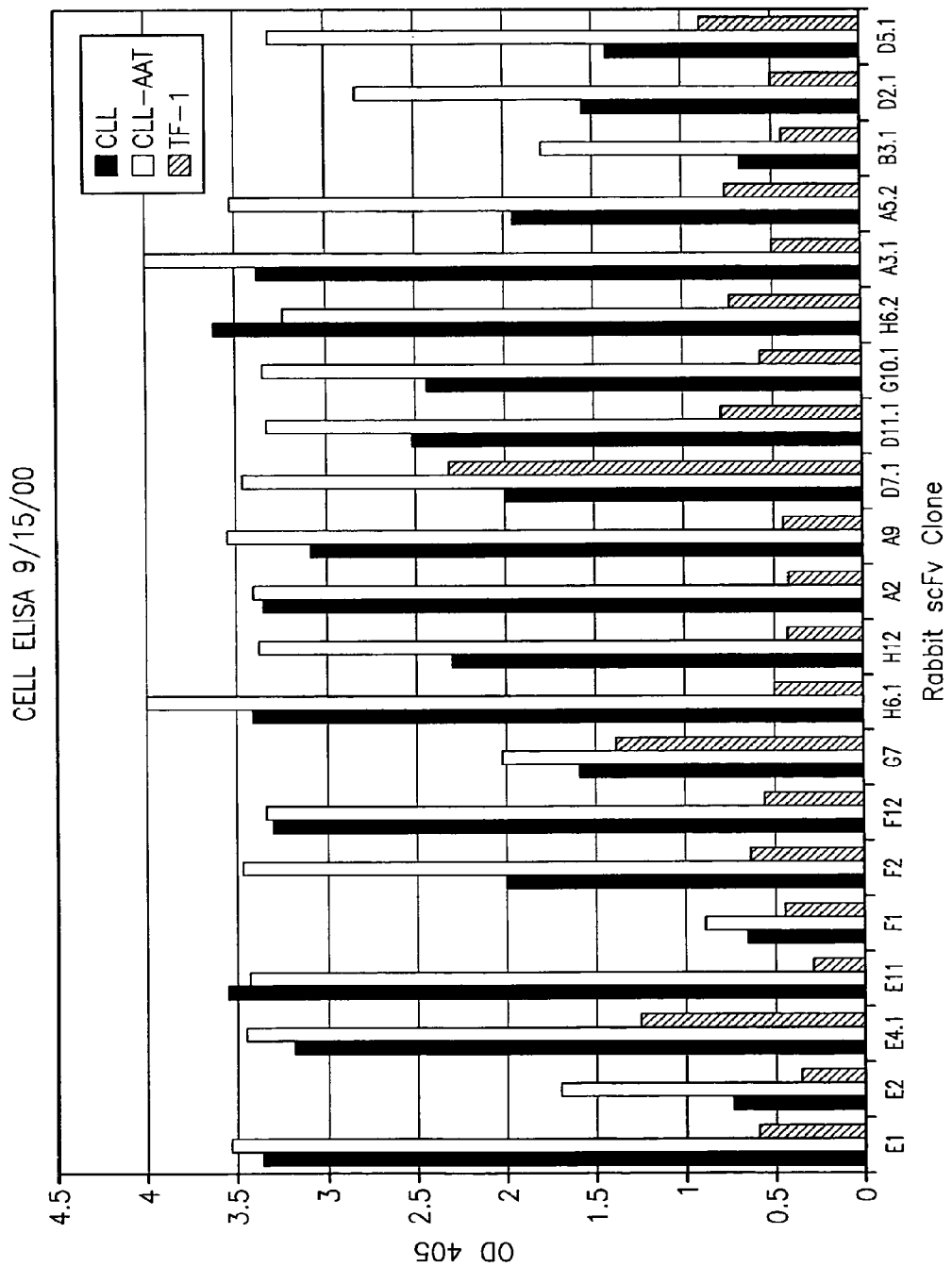
FIGS. 6a, 6b and 6c show the results of whole cell ELISA comparing binding of scFv clones to primary B-CLL cells and CLL-AAT, a cell line derived from a B-CLL patient. TF-1 Cells were included as a negative control.
Figure 6B:
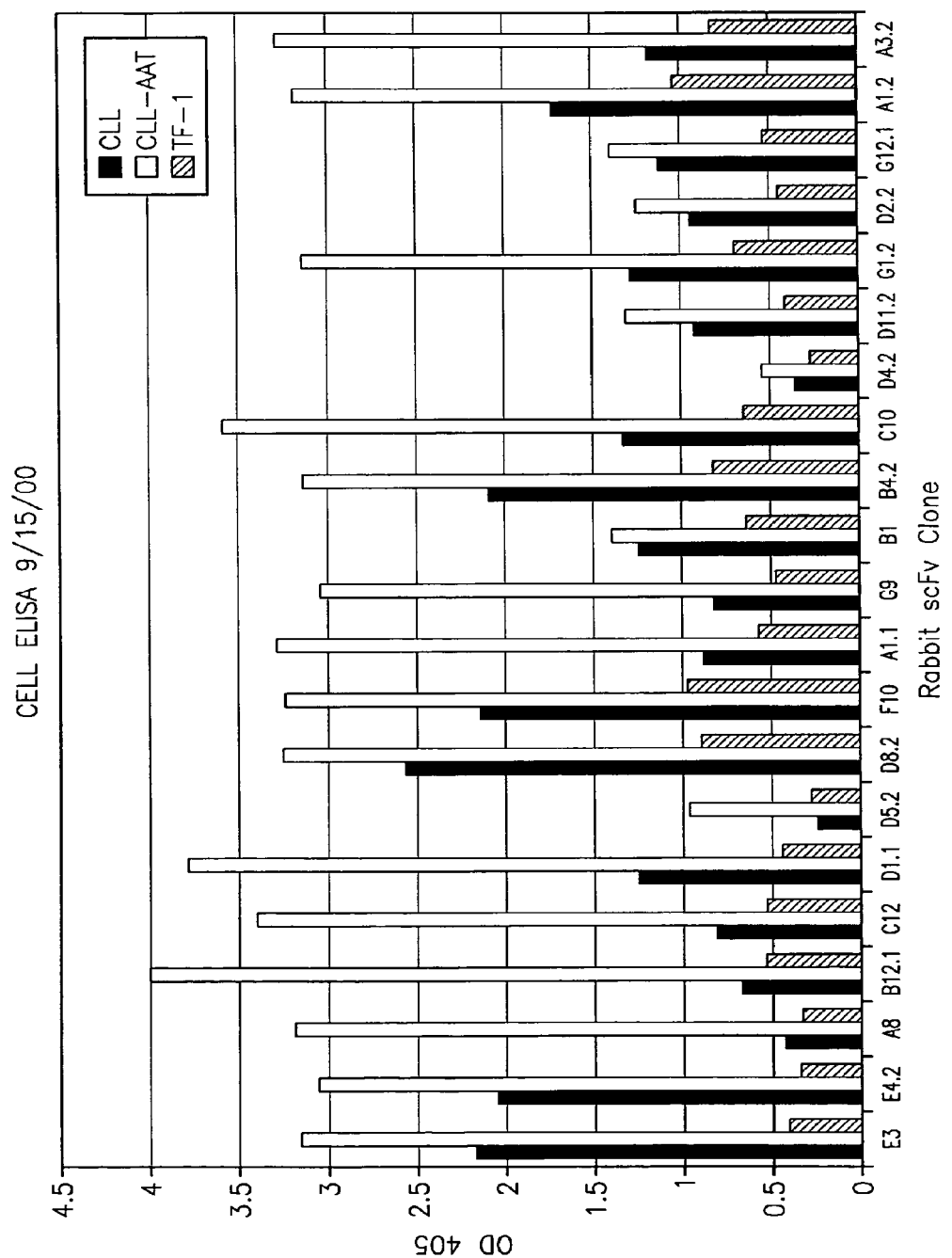
Figure 6C:
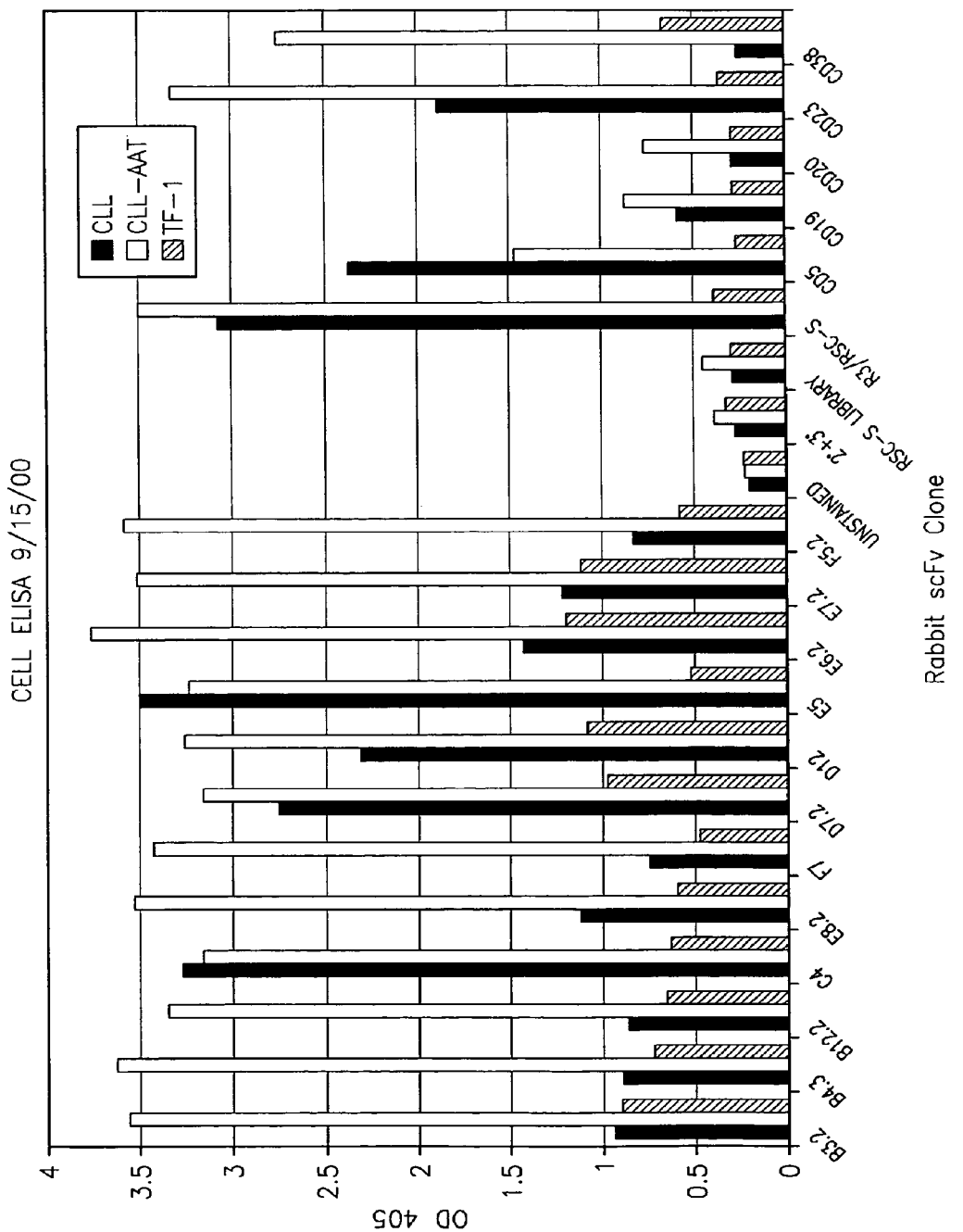

In accordance with the present disclosure, methods are provided for determining whether OX-2/CD200 is upregulated in a subject and, if so, administering to the subject a therapy that enhances immune response. Illustrative examples of suitable immunomodulatory therapies include the administration of agents that block negative regulation of T cells or antigen presenting cells (e.g., anti-CTLA4 antibodies, anti-PD-L1 antibodies, anti-PDL-2 antibodies, anti-PD-1 antibodies and the like) or the administration of agents that enhance positive co-stimulation of T cells (e.g., anti-CD40 antibodies or anti 4-1BB antibodies). Furthermore, immunomodulatory therapy could be cancer vaccines such as dendritic cells loaded with tumor cells, tumor RNA or tumor DNA, tumor protein or tumor peptides, patient derived heat-shocked proteins (hsp's) or general adjuvants stimulating the immune system at various levels such as CpG, Luivac, Biostim, Ribominyl, Imudon, Bronchovaxom or any other compound activating receptors of the innate immune system (e.g., toll like receptors). Also, immunomodulatory therapy could include treatment with cytokines such as IL-2, GM-CSF and IFN-gamma.

In particularly useful embodiments, the therapy that enhances immune response is the administration of a polypeptide that binds to OX-2/CD200, alone or in combination with one of the previously mentioned immunomodulatory therapies. In general, the polypeptides utilized in the present disclosure can be constructed using different techniques which are known to those skilled in the art. In one embodiment, the polypeptides are obtained by chemical synthesis. In other embodiments, the polypeptides are antibodies or constructed from a fragment or several fragments of one or more antibodies.

Preferably, the polypeptides utilized in the methods of the present disclosure are obtained from a CLL cell line. "CLL", as used herein, refers to chronic lymphocytic leukemia involving any lymphocyte including, but not limited to, various developmental stages of B cells and T cells including, but not limited to, B cell CLL ("B-CLL"). B-CLL, as used herein, refers to leukemia with a mature B cell phenotype which is CD5+, CD23+, $CD20^{dim+}$, $sIg^{dim+}$ and arrested in G0/G1 of the cell cycle. In a further aspect, the CLL cell line is used to generate polypeptides, including antibodies, useful in the diagnosis and/or treatment of a disease state in which OX-2/CD200 is upregulated, including cancer and CLL.

As used herein, the term "antibodies" refers to complete antibodies or antibody fragments capable of binding to a selected target. Included are Fv, scFv, Fab' and F(ab')2, monoclonal and polyclonal antibodies, engineered antibodies (including chimeric, CDR-grafted and humanized, fully human antibodies, and artificially selected antibodies), and synthetic or semi-synthetic antibodies produced using phage display or alternative techniques. Small fragments, such as Fv and scFv, possess advantageous properties for diagnostic and therapeutic applications on account of their small size and consequent superior tissue distribution.

Antibodies may be generated by using the cells as disclosed herein as immunogens, thus raising an immune response in animals from which monoclonal antibodies may be isolated. The sequence of such antibodies may be determined and the antibodies or variants thereof produced by recombinant techniques. In this aspect, "variants" includes chimeric, CDR-grafted, humanized and fully human antibodies based on the sequence of the monoclonal antibodies, as well as polypeptides capable of binding to OX-2/CD200.

Moreover, antibodies derived from recombinant libraries ("phage antibodies") may be selected using the cells described herein, or polypeptides derived therefrom, as bait to isolate the antibodies or polypeptides on the basis of target specificity.

In a still further aspect, antibodies or polypeptides may be generated by panning antibody libraries using primary CLL cells, or antigens derived therefrom, and further screened and/or characterized using a CLL cell line, such as, for example, the CLL cell line described herein. Accordingly, a method for characterizing an antibody or polypeptide specific for CLL is provided, which includes assessing the binding of the antibody or polypeptide to a CLL cell line.

Preparation of Cell Lines

Cell lines may be produced according to established methodologies known to those skilled in the art. In general, cell lines are produced by culturing primary cells derived from a patient until immortalized cells are spontaneously generated in culture. These cells are then isolated and further cultured to produce clonal cell populations or cells exhibiting resistance to apoptosis.

For example, CLL cells may be isolated from peripheral blood drawn from a patient suffering from CLL. The cells may be washed, and optionally immunotyped in order to determine the type(s) of cells present. Subsequently, the cells may be cultured in a medium, such as a medium containing IL-4. Advantageously, all or part of the medium is replaced one or more times during the culture process. Cell lines may be isolated thereby, and will be identified by increased growth in culture.

In one embodiment a CLL cell line of malignant origin is provided that is not established by immortalization with EBV. "Malignant origin" refers to the derivation of the cell line from malignant CLL primary cells, as opposed to non-proliferating cells which are transformed, for example, with EBV. Cell lines useful according to this disclosure may be themselves malignant in phenotype, or not. A CLL cell having a "malignant" phenotype encompasses cell growth unattached from substrate media characterized by repeated cycles of cell growth and exhibits resistance to apoptosis. The cell line, which was derived from primary CLL cells, is deposited under ATCC accession no. PTA-3920. In a preferred embodiment, the cell line is CLL-AAT. CLL-AAT is B-CLL cell line, derived from a B-CLL primary cell.

In one embodiment, proteins uniquely expressed in CLL cells are identified employing the CLL-AAT cell line by methods well known to those skilled in the art, such as by immunoprecipitation followed by mass spectroscopy analyses. Such proteins may be uniquely expressed in the CLL-AAT cell line, or in primary cells derived from CLL patients.

Small molecule libraries (many available commercially) may be screened using the CLL-AAT cell line in a cell-based assay to identify agents capable of modulating the growth characteristics of the cells. For example, the agents may be identified which modulate apoptosis in the CLL-AAT cell line, or which inhibit growth and/or proliferation thereof. Such agents are candidates for the development of therapeutic compounds.

Nucleic acids isolated from CLL-AAT cell lines may be used in subtractive hybridization experiments to identify CLL-specific genes or in micro array analyses (e.g., gene chip experiments). Genes whose transcription is modulated in CLL cells may be identified. Polypeptide or nucleic acid gene products identified in this manner are useful as leads for the development of antibody or small molecule therapies for CLL.

In one embodiment, the CLL-AAT cell line may be used to identify internalizing antibodies, which bind to cell surface components and are then internalized by the cell. Such antibodies are candidates for therapeutic use. In particular, single-chain antibodies, which remain stable in the cytoplasm and which retain intracellular binding activity, may be screened in this manner.

Preparation of Monoclonal Antibodies

Recombinant DNA technology may be used to improve the antibodies produced in accordance with this disclosure. Thus, chimeric antibodies may be constructed in order to decrease the immunogenicity thereof in diagnostic or therapeutic applications. Moreover, immunogenicity may be minimized by humanizing the antibodies by CDR grafting and, optionally, framework modification. See, U.S. Pat. No. 5,225,539, the contents of which are incorporated herein by reference.

Antibodies may be obtained from animal serum, or, in the case of monoclonal antibodies or fragments thereof produced in cell culture. Recombinant DNA technology may be used to produce the antibodies according to established procedure, in bacterial or preferably mammalian cell culture. The selected cell culture system preferably secretes the antibody product.

In another embodiment, a process for the production of an antibody disclosed herein includes culturing a host, e.g. *E. coli* or a mammalian cell, which has been transformed with a hybrid vector. The vector includes one or more expression cassettes containing a promoter operably linked to a first DNA sequence encoding a signal peptide linked in the proper reading frame to a second DNA sequence encoding the antibody protein. The antibody protein is then collected and isolated. Optionally, the expression cassette may include a promoter operably linked to polycistronic, for example bicistronic, DNA sequences encoding antibody proteins each individually operably linked to a signal peptide in the proper reading frame.

Multiplication of hybridoma cells or mammalian host cells in vitro is carried out in suitable culture media, which include the customary standard culture media (such as, for example Dulbecco's Modified Eagle Medium (DMEM) or RPMI 1640 medium), optionally replenished by a mammalian serum (e.g. fetal calf serum), or trace elements and growth sustaining supplements (e.g. feeder cells such as normal mouse peritoneal exudate cells, spleen cells, bone marrow macrophages, 2-aminoethanol, insulin, transferrin, low density lipoprotein, oleic acid, or the like). Multiplication of host cells which are bacterial cells or yeast cells is likewise carried out in suitable culture media known in the art. For example, for bacteria suitable culture media include medium LE, NZCYM, NZYM, NZM, Terrific Broth, SOB, SOC, 2×YT, or M9 Minimal Medium. For yeast, suitable culture media include medium YPD, YEPD, Minimal Medium, or Complete Minimal Dropout Medium.

In vitro production provides relatively pure antibody preparations and allows scale-up to give large amounts of the desired antibodies. Techniques for bacterial cell, yeast, plant, or mammalian cell cultivation are known in the art and include homogeneous suspension culture (e.g. in an airlift reactor or in a continuous stirrer reactor), and immobilized or entrapped cell culture (e.g. in hollow fibres, microcapsules, on agarose microbeads or ceramic cartridges).

Large quantities of the desired antibodies can also be obtained by multiplying mammalian cells in vivo. For this purpose, hybridoma cells producing the desired antibodies are injected into histocompatible mammals to cause growth of antibody-producing tumors. Optionally, the animals are primed with a hydrocarbon, especially mineral oils such as pristane (tetramethyl-pentadecane), prior to the injection. After one to three weeks, the antibodies are isolated from the body fluids of those mammals. For example, hybridoma cells obtained by fusion of suitable myeloma cells with antibody-producing spleen cells from Balb/c mice, or transfected cells derived from hybridoma cell line Sp2/0 that produce the desired antibodies are injected intraperitoneally into Balb/c mice optionally pre-treated with pristine. After one to two weeks, ascitic fluid is taken from the animals.

The foregoing, and other, techniques are discussed in, for example, Kohler and Milstein, (1975) Nature 256:495-497; U.S. Pat. No. 4,376,110; Harlow and Lane, Antibodies: a Laboratory Manual, (1988) Cold Spring Harbor, the disclosures of which are all incorporated herein by reference. Techniques for the preparation of recombinant antibody molecules is described in the above references and also in, for example WO97/08320; U.S. Pat. No. 5,427,908; U.S. Pat. No. 5,508, 717; Smith, 1985, Science, Vol. 225, pp 1315-1317; Parmley and Smith 1988, Gene 73, pp 305-318; De La Cruz et al, 1988, Journal of Biological Chemistry, 263 pp 4318-4322; U.S. Pat. No. 5,403,484; U.S. Pat. No. 5,223,409; WO88/06630; WO92/15679; U.S. Pat. No. 5,780,279; U.S. Pat. No. 5,571, 698; U.S. Pat. No. 6,040,136; Davis et al., Cancer Metastasis Rev., 1999; 18(4):421-5; Taylor, et al., Nucleic Acids Research 20 (1992): 6287-6295; Tomizuka et al., Proc. Nat. Academy of Sciences USA 97(2) (2000): 722-727. The contents of all these references are incorporated herein by reference.

The cell culture supernatants are screened for the desired antibodies, preferentially by immunofluorescent staining of CLL cells, by immunoblotting, by an enzyme immunoassay, e.g. a sandwich assay or a dot-assay, or a radioimmunoassay.

For isolation of the antibodies, the immunoglobulins in the culture supernatants or in the ascitic fluid may be concentrated, e.g. by precipitation with ammonium sulfate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAE-cellulose and/or (immuno-) affinity chromatography, e.g. affinity chromatography with one or more surface polypeptides derived from a CLL cell line according to this disclosure, or with Protein-A or G.

Another embodiment provides a process for the preparation of a bacterial cell line secreting antibodies directed against the cell line characterized in that a suitable mammal, for example a rabbit, is immunized with pooled CLL patient samples. A phage display library produced from the immunized rabbit is constructed and panned for the desired antibodies in accordance with methods well known in the art (such as, for example, the methods disclosed in the various references incorporated herein by reference).

Hybridoma cells secreting the monoclonal antibodies are also contemplated. The preferred hybridoma cells are genetically stable, secrete monoclonal antibodies described herein of the desired specificity and can be activated from deep-frozen cultures by thawing and recloning.

In another embodiment, a process is provided for the preparation of a hybridoma cell line secreting monoclonal antibodies directed to the CLL cell line is described herein. In that process, a suitable mammal, for example a Balb/c mouse, is immunized with a one or more polypeptides or antigenic fragments thereof derived from a cell described in this disclosure, the cell line itself, or an antigenic carrier containing a purified polypeptide as described. Antibody-producing cells of the immunized mammal are grown briefly in culture or fused with cells of a suitable myeloma cell line. The hybrid cells obtained in the fusion are cloned, and cell clones secreting the desired antibodies are selected. For example, spleen cells of Balb/c mice immunized with the present cell line are fused with cells of the myeloma cell line PAI or the myeloma cell line Sp2/0-Ag 14, the obtained hybrid cells are screened for secretion of the desired antibodies, and positive hybridoma cells are cloned.

Preferred is a process for the preparation of a hybridoma cell line, characterized in that Balb/c mice are immunized by injecting subcutaneously and/or intraperitoneally between $10^6$ and $10^7$ cells of a cell line in accordance with this disclosure several times, e.g. four to six times, over several months, e.g. between two and four months. Spleen cells from the immunized mice are taken two to four days after the last injection and fused with cells of the myeloma cell line PAI in the presence of a fusion promoter, preferably polyethylene glycol. Preferably, the myeloma cells are fused with a three- to twenty-fold excess of spleen cells from the immunized mice in a solution containing about 30% to about 50% polyethylene glycol of a molecular weight around 4000. After the fusion, the cells are expanded in suitable culture media as described hereinbefore, supplemented with a selection medium, for example HAT medium, at regular intervals in order to prevent normal myeloma cells from overgrowing the desired hybridoma cells.

In a further embodiment, recombinant DNA comprising an insert coding for a heavy chain variable domain and/or for a light chain variable domain of antibodies directed to the cell line described hereinbefore are produced. The term DNA includes coding single stranded DNAs, double stranded DNAs consisting of said coding DNAs and of complementary DNAs thereto, or these complementary (single stranded) DNAs themselves.

Furthermore, DNA encoding a heavy chain variable domain and/or a light chain variable domain of antibodies directed to the cell line disclosed herein can be enzymatically or chemically synthesized DNA having the authentic DNA sequence coding for a heavy chain variable domain and/or for the light chain variable domain, or a mutant thereof. A mutant of the authentic DNA is a DNA encoding a heavy chain variable domain and/or a light chain variable domain of the above-mentioned antibodies in which one or more amino acids are deleted or exchanged with one or more other amino acids. Preferably said modification(s) are outside the CDRs of the heavy chain variable domain and/or of the light chain variable domain of the antibody in humanization and expression optimization applications. The term mutant DNA also embraces silent mutants wherein one or more nucleotides are replaced by other nucleotides with the new codons coding for the same amino acid(s). The term mutant sequence also includes a degenerated sequence. Degenerated sequences are degenerated within the meaning of the genetic code in that an unlimited number of nucleotides are replaced by other nucleotides without resulting in a change of the amino acid sequence originally encoded. Such degenerated sequences may be useful due to their different restriction sites and/or frequency of particular codons which are preferred by the specific host, particularly *E. coli*, to obtain an optimal expression of the heavy chain murine variable domain and/or a light chain murine variable domain.

The term mutant is intended to include a DNA mutant obtained by in vitro mutagenesis of the authentic DNA according to methods known in the art.

For the assembly of complete tetrameric immunoglobulin molecules and the expression of chimeric antibodies, the recombinant DNA inserts coding for heavy and light chain variable domains are fused with the corresponding DNAs coding for heavy and light chain constant domains, then transferred into appropriate host cells, for example after incorporation into hybrid vectors.

Recombinant DNAs including an insert coding for a heavy chain murine variable domain of an antibody directed to the cell line disclosed herein fused to a human constant domain g, for example γ1, γ2, γ3 or γ4, preferably γ1 or γ4 are also provided. Recombinant DNAs including an insert coding for a light chain murine variable domain of an antibody directed to the cell line disclosed herein fused to a human constant domain κ or λ, preferably κ are also provided Another embodiment pertains to recombinant DNAs coding for a recombinant polypeptide wherein the heavy chain variable domain and the light chain variable domain are linked by way of a spacer group, optionally comprising a signal sequence facilitating the processing of the antibody in the host cell and/or a DNA coding for a peptide facilitating the purification of the antibody and/or a cleavage site and/or a peptide spacer and/or an effector molecule.

The DNA coding for an effector molecule is intended to be a DNA coding for the effector molecules useful in diagnostic or therapeutic applications. Thus, effector molecules which are toxins or enzymes, especially enzymes capable of catalyzing the activation of prodrugs, are particularly indicated. The DNA encoding such an effector molecule has the sequence of a naturally occurring enzyme or toxin encoding DNA, or a mutant thereof, and can be prepared by methods well known in the art.

Uses of the Present Antibodies/Polypeptides

The polypeptides and/or antibodies utilized herein are especially indicated for diagnostic and therapeutic applications.

The present antibodies can be administered as a therapeutic to cancer patients, especially, but not limited to CLL patients. In some embodiments, the antibodies are capable of interfering with the interaction of CD200 and its receptors. This interference can block the immune suppressing effect of CD200. By improving the immune response in this manner, such antibodies can promote the eradication of cancer cells.

The anti-CD200 antibody can also be administered in combination with other immunomodulatory compounds, vaccines or chemotherapy. For example, elimination of existing regulatory T cells with reagents such as anti-CD25 or cyclophosphamide is achieved in one particularly useful embodiment before starting anti-CD200 treatment. Also, therapeutic efficacy of myeloablative therapies followed by bone marrow transplantation or adoptive transfer of T cells reactive with CLL cells are enhanced by anti-CD200 therapy. Furthermore, anti-CD200 treatment can substantially enhance efficacy of cancer vaccines such as dendritic cells loaded with CLL cells or proteins, peptides or RNA derived from such cells, patient-derived heat-shocked proteins (hsp's), tumor peptides or protein. In other embodiments, an, anti-CD200 antibody is used in combination with an immuno-stimulatory compound, such as CpG, toll-like receptor agonists or any other adjuvant, anti-CTLA-4 antibodies, and the like. In yet other embodiments, efficacy of anti-CD200 treatment is improved by blocking of immunosuppressive mechanisms such as anti-PDL1 and/or 2 antibodies, anti-IL-10 antibodies, anti-M-6 antibodies, and the like.

Anti-CD200 antibodies in accordance with the present disclosure can also be used as a diagnostic tool. For example, using blood obtained from patients with hematopoietic cancers, expression of CD200 can be evaluated on cancer cells by FACS analysis using anti-CD200 antibodies in combination with the appropriate cancer cell markers such as, e.g., CD38 and CD19 on CLL cells. Patients with CD200 levels at least 2-fold above the levels found on normal B cells can be selected for treatment with anti-CD200 antibodies.

In another example of using the present anti-CD200 antibodies as a diagnostic tool, biopsies from patients with malignancies are obtained and expression of CD200 is determined by FACS analysis using anti-CD200 antibodies. If tumor cells express CD200 at levels that are at least 2-fold higher compared to corresponding normal tissue, cancer patients are selected for immunomodulatory therapy. Immunomodulatory therapy can be anti-CD200 therapy, but can also be any other therapy affecting the patient's immune system. Examples of suitable immunomodulatory therapies include the administration of agents that block negative regulation of T cells or antigen presenting cells (e.g., anti-CTLA4, anti-PD-L1, anti-PDL-2, anti-PD-1) or the administration of agents that enhance positive co-stimulation of T cells (e.g., anti-CD40 or anti 4-1BB). Furthermore, immunomodulatory therapy could be cancer vaccines such as dendritic cells loaded with tumor cells, tumor RNA or tumor DNA, tumor protein or tumor peptides, patient derived heat-shocked proteins (hsp's) or general adjuvants stimulating the immune system at various levels such as CpG, Luivac, Biostim, Ribominyl, Imudon, Bronchovaxom or any other compound activating receptors of the innate immune system (e.g., toll like receptors). Also, therapy could include treatment with cytokines such as IL-2, GM-CSF and IFN-gamma.

In another embodiment in accordance with the present disclosure, methods are provided for monitoring the progress and/or effectiveness of a therapeutic treatment. The method involves administering an immunomodulatory therapy and determining OX-2/CD200 levels in a subject at least twice to determine the effectiveness of the therapy. For example, pretreatment levels of OX-2/CD200 can be ascertained and, after at least one administration of the therapy, levels of OX-2/CD200 can again be determined. A decrease in OX-2/CD200 levels is indicative of an effective treatment. Measurement of OX-2/CD200 levels can be used by the practitioner as a guide for increasing dosage amount or frequency of the therapy. It should of course be understood that OX-2/CD200 levels can be directly monitored or, alternatively, any marker that correlates with OX-2/CD200 can be monitored.

The present antibodies also may be utilized to detect cancerous cells in vivo. This is achieved by labeling the antibody, administering the labeled antibody to a subject, and then imaging the subject. Examples of labels useful for diagnostic imaging in accordance with the present disclosure are radiolabels such as $^{131}$I, $^{111}$In, $^{123}$I, $^{99m}$Tc, $^{32}$P, $^{125}$I, $^{3}$H, $^{14}$C, and $^{188}$Rh, fluorescent labels such as fluorescein and rhodamine, nuclear magnetic resonance active labels, positron emitting isotopes detectable by a positron emission tomography ("PET") scanner, chemiluminescers such as luciferin, and enzymatic markers such as peroxidase or phosphatase. Short-range radiation emitters, such as isotopes detectable by short-range detector probes, such as a transrectal probe, can also be employed. The antibody can be labeled with such reagents using techniques known in the art. For example, see Wensel and Meares, Radioimmunoimaging and Radioimmunotherapy, Elsevier, N.Y. (1983), which is hereby incorporated by reference, for techniques relating to the radiolabeling of antibodies. See also, D. Colcher et al., "Use of Monoclonal Antibodies as Radiopharmaceuticals for the Localization of Human Carcinoma Xenografts in Athymic Mice", Meth. Enzymol. 121: 802-816 (1986), which is hereby incorporated by reference.

A radiolabeled antibody in accordance with this disclosure can be used for in vitro diagnostic tests. The specific activity of a antibody, binding portion thereof, probe, or ligand, depends upon the half-life, the isotopic purity of the radioactive label, and how the label is incorporated into the biological agent. In immunoassay tests, the higher the specific activity, in general, the better the sensitivity. Procedures for labeling antibodies with the radioactive isotopes are generally known in the art.

The radiolabeled antibodies can be administered to a patient where it is localized to cancer cells bearing the antigen with which the antibody reacts, and is detected or "imaged" in vivo using known techniques such as radionuclear scanning using e.g., a gamma camera or emission tomography. See e.g., A. R. Bradwell et al., "Developments in Antibody Imaging", Monoclonal Antibodies for Cancer Detection and Therapy, R. W. Baldwin et al., (eds.), pp. 65-85 (Academic Press 1985), which is hereby incorporated by reference. Alternatively, a positron emission transaxial tomography scanner, such as designated Pet VI located at Brookhaven National Laboratory, can be used where the radiolabel emits positrons (e.g., $^{18}$F, $^{15}$O, and $^{13}$N).

Fluorophore and chromophore labeled biological agents can be prepared from standard moieties known in the art. Since antibodies and other proteins absorb light having wavelengths up to about 310 nm, the fluorescent moieties should be selected to have substantial absorption at wavelengths above 310 nm and preferably above 400 nm. A variety of suitable fluorescers and chromophores are described by Stryer, Science, 162:526 (1968) and Brand, L. et al., Annual Review of Biochemistry, 41:843-868 (1972), which are hereby incorporated by reference. The antibodies can be labeled with fluorescent chromophore groups by conventional procedures such as those disclosed in U.S. Pat. Nos. 3,940,475, 4,289,747, and 4,376,110, which are hereby incorporated by reference.

In other embodiments, bispecific antibodies are contemplated. Bispecific antibodies are monoclonal, preferably human or humanized, antibodies that have binding specificities for at least two different antigens. In the present case, one of the binding specificities is for the CD200 antigen on a cancer cell, the other one is for any other antigen, and preferably for a cell-surface protein or receptor or receptor subunit.

Methods for making bispecific antibodies are within the purview of those skilled in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Antibody variable domains with the desired binding specificities (antibody-antigen combining sites) can be fused to immunoglobulin constant domain sequences. The fusion preferably is with an immunoglobulin heavy-chain constant domain, including at least part of the hinge, CH2, and CH3 regions. DNAs encoding the immunoglobulin heavy-chain fusions and, if desired, the immunoglobulin light chain, are inserted into separate expression vectors, and are co-transfected into a suitable host organism. For further details of illustrative currently known methods for generating bispecific antibodies see, for example, Suresh et al., Methods in Enzymology, 121:210 (1986); WO 96/27011; Brennan et al., Science 229:81 (1985); Shalaby et al., J. Exy. Med. 175:217-225 (1992); Kostelny et al., J. Immunol. 148(5):1547-1553

(1992); Hollinger et al., Proc. Natl. Acad. Sci. USA 90:6444-6448 (1993); and Gruber et al., J. Immunol. 152:5368 (1994); and Tutt et al., J. Immunol. 147:60 (1991).

The present antibodies can also be utilized to directly kill or ablate cancerous cells in vivo. This involves administering the antibodies (which are optionally fused to a cytotoxic drug) to a subject requiring such treatment. Since the antibodies recognize CD200 on cancer cells, any such cells to which the antibodies bind are destroyed.

Where the antibodies are used alone to kill or ablate cancer cells, such killing or ablation can be effected by initiating endogenous host immune functions, such as complement-mediated or antibody-dependent cellular cytotoxicity. Assays for determining whether an antibody kills cells in this manner are within the purview of those skilled in the art.

The antibodies of the present disclosure may be used to deliver a variety of cytotoxic compounds. Any cytotoxic compound can be fused to the present antibodies. The fusion can be achieved chemically or genetically (e.g., via expression as a single, fused molecule). The cytotoxic compound can be a biological, such as a polypeptide, or a small molecule. As those skilled in the art will appreciate, for small molecules, chemical fusion is used, while for biological compounds, either chemical or genetic fusion can be employed.

Non-limiting examples of cytotoxic compounds include therapeutic drugs, a compound emitting radiation, molecules of plants, fungal, or bacterial origin, biological proteins, and mixtures thereof. The cytotoxic drugs can be intracellularly acting cytotoxic drugs, such as short-range radiation emitters, including, for example, short-range, high-energy α-emitters. Enzymatically active toxins and fragments thereof are exemplified by diphtheria toxin A fragment, nonbinding active fragments of diphtheria toxin, exotoxin A (from *Pseudomonas aeruginosa*), ricin A chain, abrin A chain, modeccin A chain, .alpha.-sacrin, certain Aleurites fordii proteins, certain Dianthin proteins, Phytolacca americana proteins (PAP, PAPII and PAP-S), Morodica charantia inhibitor, curcin, crotin, *Saponaria officinalis* inhibitor, gelonin, mitogillin, restrictocin, phenomycin, and enomycin, for example. Procedures for preparing enzymatically active polypeptides of the immunotoxins are described in WO84/03508 and WO85/03508, which are hereby incorporated by reference. Certain cytotoxic moieties are derived from adriamycin, chlorambucil, daunomycin, methotrexate, neocarzinostatin, and platinum, for example.

Procedures for conjugating the antibodies with the cytotoxic agents have been previously described and are within the purview of one skilled in the art.

Alternatively, the antibody can be coupled to high energy radiation emitters, for example, a radioisotope, such as $^{131}I$, a γ-emitter, which, when localized at the tumor site, results in a killing of several cell diameters. See, e.g., S. E. Order, "Analysis, Results, and Future Prospective of the Therapeutic Use of Radiolabeled Antibody in Cancer Therapy", Monoclonal Antibodies for Cancer Detection and Therapy, R. W. Baldwin et al. (eds.), pp 303-316 (Academic Press 1985), which is hereby incorporated by reference. Other suitable radioisotopes include α-emitters, such as $^{212}Bi$, $^{213}Bi$, and $^{211}At$, and β-emitters, such as $^{186}Re$ and $^{90}Y$.

The route of antibody administration of the present antibodies (whether the pure antibody, a labeled antibody, an antibody fused to a toxin, etc.) is in accord with known methods, e.g., injection or infusion by intravenous, intraperitoneal, intracerebral, intramuscular, subcutaneous, intraocular, intraarterial, intrathecal, inhalation or intralesional routes, or by sustained release systems. The antibody is preferably administered continuously by infusion or by bolus injection. One may administer the antibodies in a local or systemic manner.

The present antibodies may be prepared in a mixture with a pharmaceutically acceptable carrier. Techniques for formulation and administration of the compounds of the instant application may be found in "Remington's Pharmaceutical Sciences," Mack Publishing Co., Easton, Pa., latest edition. This therapeutic composition can be administered intravenously or through the nose or Jung, preferably as a liquid or powder aerosol (lyophilized). The composition may also be administered parenterally or subcutaneously as desired. When administered systematically, the therapeutic composition should be sterile, pyrogen-free and in a parenterally acceptable solution having due regard for pH, isotonicity, and stability. These conditions are known to those skilled in the art.

Pharmaceutical compositions suitable for use include compositions wherein one or more of the present antibodies are contained in an amount effective to achieve their intended purpose. More specifically, a therapeutically effective amount means an amount of antibody effective to prevent, alleviate or ameliorate symptoms of disease or prolong the survival of the subject being treated. Determination of a therapeutically effective amount is well within the capability of those skilled in the art, especially in light of the detailed disclosure provided herein. Therapeutically effective dosages may be determined by using in vitro and in vivo methods.

In some embodiments, present CD200 binding antibodies provide the benefit of blocking immune suppression in CLL by targeting the leukemic cells directly through CD200. Specifically, stimulating the immune system can allow the eradication of CLL cells from the spleen and lymph nodes. Applicants are unaware of any successful eradication of CLL cells from these microenvironments having been achieved with agents that simply target B cells (such as alemtuzumab). In contrast, CLL reactive T cells can have better access to these organs than antibodies. In other embodiments, direct cell killing is achieved by tagging the CLL cells with anti-CD200 Abs.

In particularly useful embodiments, the combination of direct cell killing and driving the immune response towards a Th1 profile provides a particularly powerful approach to cancer treatment. Thus, in one embodiments, a cancer treatment is provided wherein an antibody or antibody fragment that binds to CD200 both a) blocks the interaction between CD200 and its receptor and b) directly kills the cancer cells expressing CD200 is administered to a cancer patient. The mechanism by which the cancer cells are killed can include, but are not limited to antibody-dependent cellular cytotoxicity (ADCC) or complement dependent cytotoxicity (CDC); fusion with a toxin; fusion with a radiolabel; fusion with a biological agent involved in cell killing, such as granzyme B or perforin; fusion with a cytotoxic virus; fusion with a cytokine such as TNF-α or IFN-α.

In an alternative embodiment, a cancer treatment involves administering an antibody that both a) blocks the interaction between CD200 and its receptor and b) enhances cytotoxic T cell or NK cell activity against the tumor. Such enhancement of the cytotoxic T cell or NK cell activity may, for example, be combined by fusing the antibody with cytokines such as e.g. IL-2, IL-12, IL-18, IL-13, IL-5.

In yet another embodiment, the cancer treatment involves administering an antibody that both a) blocks the interaction between CD200 and its receptor and b) attracts T cells to the tumor cells. T cell attraction can be achieved by fusing the Ab with chemokines such as MIG, IP-10, I-TAC, CCL21, CCL5 or LIGHT. The combined action of blocking immune suppression and killing directly through antibody targeting of the tumor cells is a unique approach that provides increased efficacy.

While the above disclosure has been directed to antibodies, in some embodiments polypeptides derived from such antibodies can be utilized in accordance with the present disclosure.

Uses of the CLL Cell Line

There are many advantages to the development of a CLL cell line, as it provides an important tool for the development of diagnostics and treatments for CLL, cancer, and other disease states characterized by upregulated levels of OX-2/CD200, e.g., melanoma.

A cell line according to this disclosure may be used for in vitro studies on the etiology, pathogenesis and biology of CLL and other disease states characterized by upregulated levels of OX-2/CD200. This assists in the identification of suitable agents that are useful in the therapy of these diseases.

The cell line may also be used to produce polypeptides and/or monoclonal antibodies for in vitro and in vivo diagnosis of CLL, cancer, and other disease states characterized by upregulated levels of OX-2/CD200 (e.g., melanoma), as referred to above, and for the screening and/or characterization of antibodies produced by other methods, such as by panning antibody libraries with primary cells and/or antigens derived from CLL patients.

The cell line may be used as such, or antigens may be derived therefrom. Advantageously, such antigens are cell-surface antigens specific for CLL. They may be isolated directly from cell lines according to this disclosure. Alternatively, a cDNA expression library made from a cell line described herein may be used to express CLL-specific antigens, useful for the selection and characterization of anti-CLL antibodies and the identification of novel CLL-specific antigens.

Treatment of CLL using monoclonal antibody therapy has been proposed in the art. Recently, Hainsworth (Oncologist 5 (5) (2000) 376-384) has described the current therapies derived from monoclonal antibodies. Lymphocytic leukemia in particular is considered to be a good candidate for this therapeutic approach due to the presence of multiple lymphocyte-specific antigens on lymphocyte tumors.

Existing antibody therapies (such as Rituximab™, directed against the CD20-antigen, which is expressed on the surface of B-lymphocytes) have been used successfully against certain lymphocytic disease. However, a lower density CD20 antigen is expressed on the surface of B-lymphocytes in CLL (Almasri et al., Am. J. Hematol., 40 (4) (1992) 259-263).

The CLL cell line described herein thus permits the development of novel anti-CLL antibodies and polypeptides having specificity for one or more antigenic determinants of the present CLL cell line, and their use in the therapy and diagnosis of CLL, cancer, and other disease states characterized by upregulated levels of OX-2/CD200.

The antibody or polypeptide may bind to a receptor with which OX-2/CD200 normally interacts, thereby preventing or inhibiting OX-2/CD200 from binding to the receptor. As yet another alternative, the antibody can bind to an antigen that modulates expression of OX-2/CD200, thereby preventing or inhibiting normal or increased expression of OX-2/CD200. Because the presence of OX-2/CD200 has been associated with reduced immune response, it would be desirable to interfere with the metabolic pathway of OX-2/CD200 so that the patient's immune system can defend against the disease state, such as cancer or CLL, more effectively.

In a particularly useful embodiment, the polypeptide binds to OX-2/CD200. In one embodiment, the polypeptide can be an antibody which binds to OX-2/CD200 and prevents or inhibits OX-2/CD200 from interacting with other molecules or receptors. As CLL cells and other cells overexpressing OX-2/CD200 greatly diminish the production of Th1 cytokines, the administration of anti-CD200 antibody or a polypeptide which binds to OX-2/CD200 to a subject having upregulated levels of OX-2/CD200 restores the Th1 cytokine profile. Thus, these polypeptides and/or antibodies can be useful therapeutic agents in the treatment of CLL and other cancers or diseases over-expressing OX-2/CD200.

Thus, in another embodiment, the method of the present disclosure includes the steps of screening a subject for the presence OX-2/CD200 and administering a polypeptide that binds to OX-2/CD200. It should of course be understood that the presence of OX-2/CD200 can be directly monitored or, alternatively, any marker that correlates with OX-2/CD200 can be detected. In a particularly useful embodiment, a CLL patient is screened for overexpression of OX-2/CD200 and an antibody that binds to OX-2/CD200 is administered to the patient. As described in detail below, one such antibody is scFv-9 (see FIG. 9B) which binds to OX-2/CD200.

In order that those skilled in the art may be better able to practice the compositions and methods described herein, the following examples are given for illustration purposes.

EXAMPLE 1

Isolation of Cell Line CLL-AAT

Establishment of the Cell Line

Peripheral blood from a patient diagnosed with CLL was obtained. The WBC count was $1.6 \times 10^8$/ml. Mononuclear cells were isolated by HISTOPAQUE®-1077 density gradient centrifugation (Sigma Diagnostics, St. Louis, Mo.). Cells were washed twice with Iscove's Modified Dulbecco's Medium (IMDM) supplemented with 10% heat-inactivated fetal bovine serum (FBS), and resuspended in 5 ml of ice-cold IMDM/10% FBS. Viable cells were counted by staining with trypan blue. Cells were mixed with an equal volume of 85% FBS/15% DMSO and frozen in 1 ml aliquots for storage in liquid nitrogen.

Immunophenotyping showed that >90% of the CD45+ lymphocyte population expressed IgD, kappa light chain, CD5, CD19, and CD23. This population also expressed low levels of IgM and CD20. Approximately 50% of the cells expressed high levels of CD38. The cells were negative for lambda light chain, CD10 and CD138

An aliquot of the cells was thawed, washed, and resuspended at a density of $10^7$/mL in IMDM supplemented with 20% heat-inactivated FBS, 2 mM L-glutamine, 100 units/ml penicillin, 100 µg/ml streptomycin, 50 µM 2-mercaptoethanol, and 5 ng/ml recombinant human IL-4 (R & D Systems, Minneapolis, Minn.). The cells were cultured at 37° C. in a humidified 5% $CO_2$ atmosphere. The medium was partially replaced every 4 days until steady growth was observed. After 5 weeks, the number of cells in the culture began to double approximately every 4 days. This cell line was designated CLL-AAT.

Characterization of the Cell Line

Immunophenotyping of the cell line by flow cytometry showed high expression of IgM, kappa light chain, CD23, CD38, and CD138, moderate expression of CD19 and CD20, and weak expression of IgD and CD5. The cell line was negative for lambda light chain, CD4, CD8, and CD10.

Immunophenotyping of the cell line was also done by whole cell ELISA using a panel of rabbit scFv antibodies that had been selected for specific binding to primary B-CLL cells. All of these CLL-specific scFv antibodies also recognized the CLL-AAT cell line. In contrast, the majority of the scFvs did not bind to two cell lines derived from B cell lymphomas: Ramos, a Burkitt's lymphoma cell line, and RL, a non-Hodgkin's lymphoma cell line.

EXAMPLE 2

Selection of scFv Antibodies for B-CLL-Specific Cell Surface Antigens using Antibody Phage Display and Cell Surface Panning Immunizations and ScFv Antibody Library Construction Peripheral blood mononuclear cells (PBMC) were isolated from blood drawn from CLL patients at the Scripps Clinic (La Jolla, Calif.). Two rabbits were immunized with $2 \times 10^7$ PBMC pooled from 10 different donors with CLL. Three immunizations, two sub-cutaneous injections followed by one intravenous injection, were done at three week intervals. Serum titers were checked by measuring binding of serum IgG to primary CLL cells using flow cytometry. Five days after the final immunization, spleen, bone marrow, and PBMC were harvested from the animals. Total RNA was isolated from these tissues using Tri-Reagent (Molecular Research Center, Inc). Single-chain Fv (scFv) antibody phage display libraries were constructed as previously described (Barbas et al., (2001) Phage Display: A Laboratory Manual, Cold Spring Harbor Laboratory Press, Cold Spring Harbor, N.Y.). For cell surface panning, phagemid particles from the reamplified library were precipitated with polyethylene glycol (PEG), resuspended in phosphate-buffered saline (PBS) containing 1% bovine serum albumin (BSA), and dialysed overnight against PBS.

Antibody Selection by Cell Surface Panning

The libraries were enriched for CLL cell surface-specific antibodies by positive-negative selection with a magnetically-activated cell sorter (MACS) as described by Siegel et al. (1997, J. Immunol. Methods 206:73-85). Briefly, phagemid particles from the scFv antibody library were pre-incubated in MPBS (2% nonfat dry milk, 0.02% sodium azide in PBS, pH 7.4) for 1 hour at 25° C. to block nonspecific binding sites. Approximately $10^7$ primary CLL cells were labeled with mouse anti-CD5 IgG and mouse anti-CD19 IgG conjugated to paramagnetic microbeads (Miltenyi Biotec, Sunnyvale, Calif.). Unbound microbeads were removed by washing. The labeled CLL cells ("target cells") were mixed with an excess of "antigen-negative absorber cells", pelleted, and resuspended in 50 µl ($10^{10}$-$10^{11}$ cfu) of phage particles. The absorber cells serve to soak up phage that stick non-specifically to cell surfaces as well as phage specific for "common" antigens present on both the target and absorber cells. The absorber cells used were either TF-1 cells (a human erythroleukemia cell line) or normal human B cells isolated from peripheral blood by immunomagnetic negative selection (StemSep® system, StemCell Technologies, Vancouver, Canada). The ratio of absorber cells to target cells was approximately 10-fold by volume. After a 30 minute incubation at 25° C., the cell/phage mixture was transferred to a MiniMACS™ MS$^+$ separation column. The column was washed twice with 0.5 ml of MPBS, and once with 0.5 ml of PBS to remove the unbound phage and absorber cells. The target cells were eluted from the column in 1 ml of PBS and pelleted in a microcentrifuge at maximum speed for 15 seconds. The captured phage particles were eluted by resuspending the target cells in 200 µl of acid elution buffer (0.1 N HCl, pH adjusted to 2.2 with glycine, plus 1 mg/ml BSA). After a 10 minute incubation at 25° C., the buffer was neutralized with 12 µL of 2M Tris base, pH10.5, and the eluted phage were amplified in E. coli for the next round of panning. For each round of panning, the input and output phage titers were determined. The input titer is the number of reamplified phage particles added to the target cell/absorber cell mixture and the output titer is the number of captured phage eluted from the target cells. An enrichment factor (E) is calculated using the formula $E=(R_n \text{ output}/R_n \text{ input})/(R_1 \text{ output}/R_1 \text{ input})$. In most cases, an enrichment factor of $10^2$-$10^3$ fold should be attained by the third or fourth round.

Analysis of Enriched Antibody Pools Following Panning

After 3-5 rounds of panning, the pools of captured phage were assayed for binding to CLL cells by flow cytometry and/or whole cell ELISA:

1. To produce an entire pool in the form of HA-tagged soluble antibodies, 2 ml of a non-suppressor strain of E. coli (e.g. TOP10F') was infected with 1 µl ($10^9$-$10^{10}$ cfu) of phagemid particles. The original, unpanned library was used as a negative control. Carbenicillin was added to a final concentration of 10 µM and the culture was incubated at 37° C. with shaking at 250 rpm for 1 hour. Eight ml of SB medium containing 50 µg/ml carbenicillin was added and the culture was grown to an OD 600 of ~0.8. IPTG was added to a final concentration of 1 mM to induce scFv expression from the Lac promoter and shaking at 37° C. was continued for 4 hours. The culture was centrifuged at 3000×g for 15'. The supernatant containing the soluble antibodies was filtered and stored in 1 ml aliquots at ~20° C.

2. Binding of the scFv antibody pools to target cells vs. absorber cells was determined by flow cytometry using high-affinity Rat Anti-HA (clone 3F10, Roche Molecular Biochemicals) as secondary antibody and PE-conjugated Donkey Anti-Rat as tertiary antibody.

3. Binding of the antibody pools to target cells vs. absorber cells was also determined by whole-cell ELISA as described below.

Screening Individual scFv Clones Following Panning

To screen individual scFv clones following panning, TOP10F' cells were infected with phage pools as described above, spread onto LB plates containing carbenicillin and tetracycline, and incubated overnight at 37° C. Individual colonies were inoculated into deep 96-well plates containing 0.6-1.0 ml of SB-carbenicillin medium per well. The cultures were grown for 6-8 hours in a HiGro® shaking incubator (GeneMachines, San Carlos, Calif.) at 520 rpm and 37° C. At this point, a 90 µl aliquot from each well was transferred to a deep 96-well plate containing 10 µL of DMSO. This replica plate was stored at −80° C. IPTG was added to the original plate to a final concentration of 1 mM and shaking was continued for 3 hours. The plates were centrifuged at 3000×g for 15 minutes. The supernatants containing soluble scFv antibodies were transferred to another deep 96-well plate and stored at −20° C.

A sensitive whole-cell ELISA method for screening HA-tagged scFv antibodies was developed:

1. An ELISA plate is coated with concanavalin A (10 mg/ml in 0.1 M NaHCO$_3$, 018.6, 0.1 mM CaCl$_2$).

2. After washing the plate with PBS, 0.5-1×10$^5$ target cells or absorber cells in 500 of PBS are added to each well, and the plate is centrifuged at 250×g for 10 minutes.

3. 50 µl of 0.02% glutaraldehyde in PBS are added and the cells are fixed overnight at 4° C.

4. After washing with PBS, non-specific binding sites are blocked with PBS containing 4% non-fat dry milk for 3 hours at room temperature.
5. The cells are incubated with 50 µl of soluble, HA-tagged scFv or Fab antibody (TOP 10F' supernatant) for 2 hours at room temperature, then washed six times with PBS.
6. Bound antibodies are detected using a Mouse Anti-HA secondary antibody (clone 12CA5) and an alkaline phosphatase (AP)-conjugated Anti-Mouse IgG tertiary antibody. An about 10-fold amplification of the signal is obtained by using AMDEX AP-conjugated Sheep Anti-Mouse IgG as the tertiary antibody (Amersham Pharmacia Biotech). The AMDEX antibody is conjugated to multiple AP molecules via a dextran backbone. Color is developed with the alkaline phosphatase substrate PNPP and measured at 405 nm using a microplate reader.

Primary screening of the scFv clones was done by ELISA on primary CLL cells versus normal human PBMC. Clones which were positive on CLL cells and negative on normal PBMC were rescreened by ELISA on normal human B cells, human B cell lines, TF-1 cells, and the CLL-AAT cell line. The clones were also rescreened by ELISA on CLL cells isolated from three different patients to eliminate clones that recognized patient-specific or blood type-specific antigens. Results from representative ELISAs are shown in FIGS. 2-6 and summarized in FIGS. 9A, 9B and 9C.

The number of unique scFv antibody clones obtained was determined by DNA fingerprinting and sequencing. The scFv DNA inserts were amplified from the plasmids by PCR and digested with the restriction enzyme BstNI. The resulting fragments were separated on a 4% agarose gel and stained with ethidium bromide. Clones with different restriction fragment patterns must have different amino acid sequences. Clones with identical patterns probably have similar or identical sequences. Clones with unique BstNI fingerprints were further analyzed by DNA sequencing. Twenty-five different sequences were found, which could be clustered into 16 groups of antibodies with closely related complementarity determining regions (FIGS. 9A, 9B and 9C).

Characterization of scFv Antibodies by Flow Cytometry

The binding specificities of several scFv antibodies were analyzed by 3-color flow cytometry (FIG. 7). PBMC isolated from normal donors were stained with FITC-conjugated anti-CD5 and PerCP-conjugated anti-CD19. Staining with scFv antibody was done using biotin-conjugated anti-HA as secondary antibody and PE-conjugated streptavidin. Three antibodies, scFv-2, scFv-3, and scFv-6, were found to specifically recognize the CD19$^+$ B lymphocyte population (data not shown). The fourth antibody, scFv-9, recognized two distinct cell populations: the CD19$^+$ B lymphocytes and a subset of CD5$^+$ T lymphocytes (FIG. 7). Further characterization of the T cell subset showed that it was a subpopulation of the CD4$^+$ CD8$^-$ TH cells (data not shown).

Figure 8A:
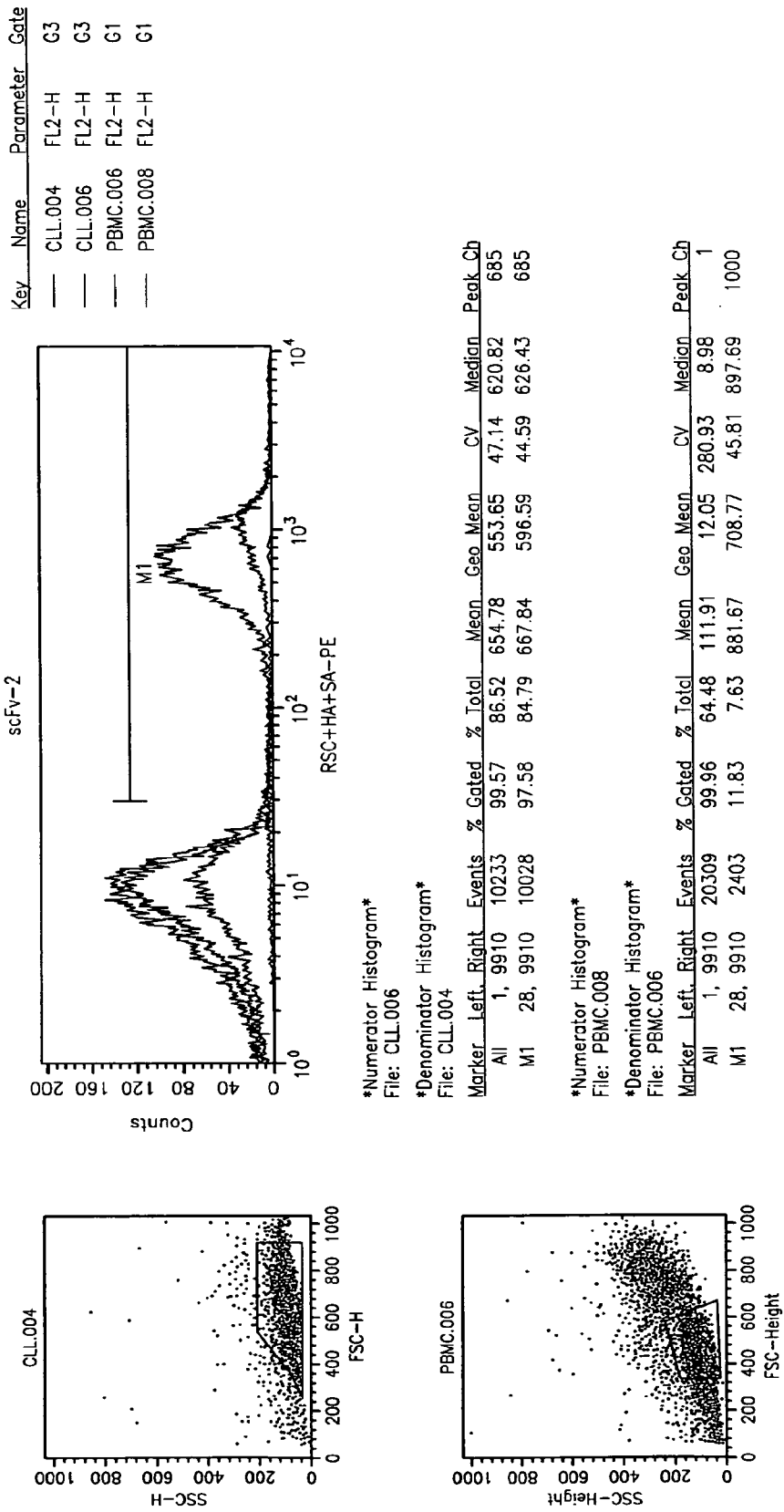
FIGS. 8a, 8b and 8c show the expression levels of antigens recognized by scFv antibodies in accordance with this disclosure. The antigens recognized by scFv-3 and scFv-9 are overexpressed on the primary CLL tumor from which the CLL-AAT cell line was derived. Primary PBMC from the CLL patient used to establish the CLL-AAT cell line or PBMC from a normal donor were stained with scFv antibody and analyzed by flow cytometry. ScFv-3 and scFv-9 stain the CLL cells more brightly than the normal PBMC as measured by the mean fluorescent intensities.
Figure 8B:
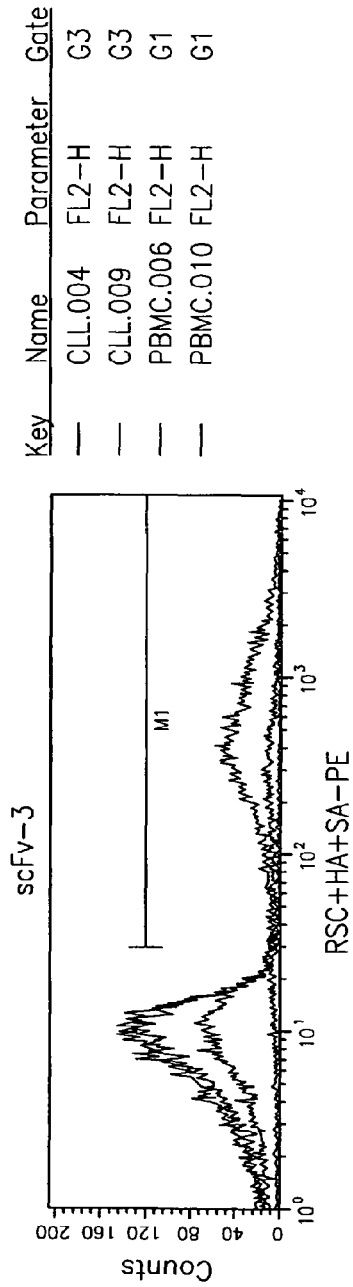
Figure 8C:
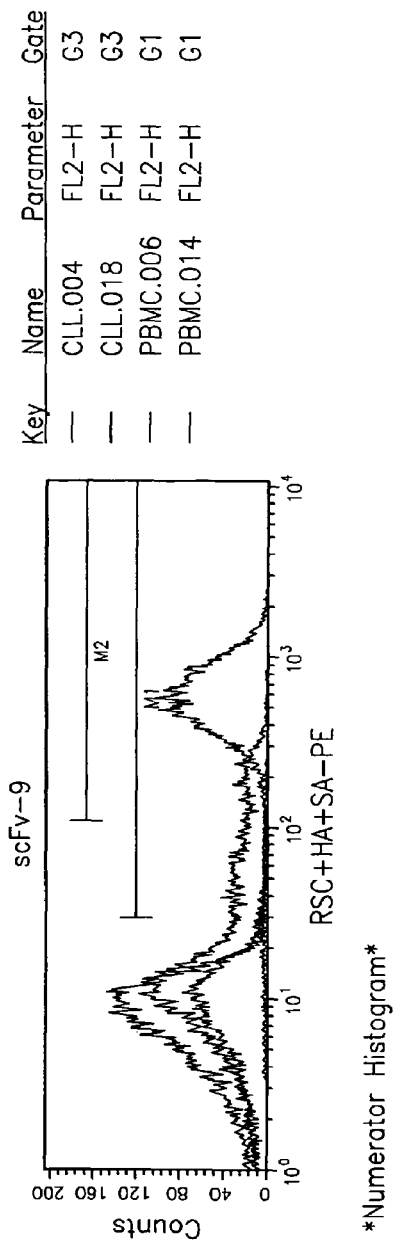

To determine if the antigens recognized by the scFv antibodies were overexpressed on primary CLL cells, PBMC from five CLL patients and five normal donors were stained with scFv and compared by flow cytometry (FIG. 8 and Table 2). By comparing the mean fluorescent intensities of the positive cell populations, the relative expression level of an antigen on CLL cells vs. normal cells could be determined. One antibody, scFv-2, consistently stained CLL cells less intensely than normal PBMC, whereas scFv-3 and scFv-6 both consistently stained CLL cells more brightly than normal PBMC. The fourth antibody, scFv-9, stained two of the five CLL samples much more intensely than normal PBMC, but gave only moderately brighter staining for the other three CLL samples (FIG. 8 and Table 2). This indicates that the antigens for scFv-3 and scFv-6 are overexpressed approximately 2-fold on most if not all CLL tumors, whereas scFv-9 is overexpressed 3 to 6-fold on a subset of CLL tumors.

CLL patients can be divided into two roughly equal groups: those with a poor prognosis (median survival time of 8 years) and those with a favorable prognosis (median survival time of 26 years). Several unfavorable prognostic indicators have been identified for CLL, most notably the presence of VH genes lacking somatic mutations and the presence of a high percentage of CD38$^+$ B cells. Since scFv-9 recognizes an antigen overexpressed in only a subset of CLL patients, it was sought to determine if scFv-9 antigen overexpression correlated with the percentage of CD38$^+$ cells in blood samples from ten CLL patients (FIG. 11). The results indicate that scFv-9 antigen overexpression and percent CD38$^+$ cells are completely independent of one another.

Identification of Antigens Recognized by scFv Antibodies by Immunoprecipitation (IP) and Mass Spectrometry (MS)

Figure 12:
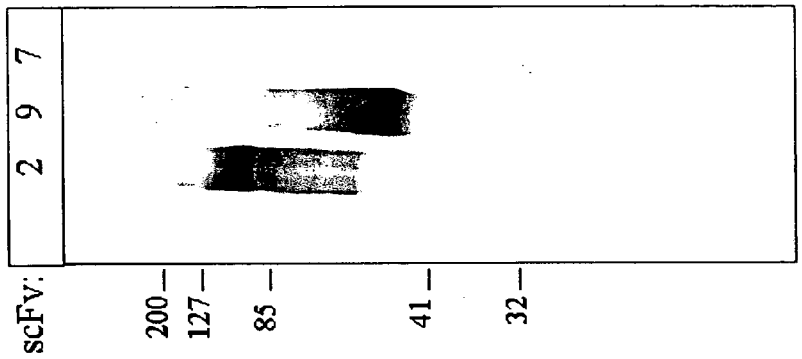
FIG. 12 shows the identification of scFv antigens by immunoprecipitation and mass spectrometry. CLL-AAT cells were labeled with a solution of 0.5 mg/ml sulfo-NHS-LC-biotin (Pierce) in PBS, pH 8.0 for 30'. After extensive washing with PBS to remove unreacted biotin, the cells were disrupted by nitrogen cavitation and the microsomal fraction was isolated by differential centrifugation. The microsomal fraction was resuspended in NP40 Lysis Buffer and extensively precleared with normal rabbit serum and Protein A SEPHAROSE®. Antigens were immunoprecipitated with HA-tagged scFv antibodies coupled to Rat Anti-HA agarose beads (Roche). Following immunoprecipitation, antigens were separated by SDS-PAGE and detected by Western blot using streptavidin-alkaline phosphatase (AP) or by Coomassie G-250 staining. ScFv-7, an antibody which doesn't bind to CLL-AAT cells, was used as a negative control. Antigen bands were excised from the Coomassie-stained gel and identified by mass spectrometry (MS). MALDI-MS was performed at the Proteomics Core Facility of The Scripps Research Institute (La Jolla, Calif.). µLC/MS/MS was performed at the Harvard Microchemistry Facility (Cambridge, Mass.).

To identify the antigens for these antibodies, scFvs were used to immunoprecipitate the antigens from lysates prepared from the microsomal fraction of cell-surface biotinylated CLL-AAT cells (FIG. 12). The immunoprecipitated antigens were purified by SDS-PAGE and identified by matrix assisted laser desorption ionization mass spectrometry (MALDI-MS) or microcapillary reverse-phase HPLC nano-electrospray tandem mass spectrometry (µLC/MS/MS) (data not shown). ScFv-2 immunoprecipitated a 110 kd antigen from both RL and CLL-AAT cells (FIG. 12). This antigen was identified by MALDI-MS as the B cell-specific marker CD19. ScFv-3 and scFv-6 both immunoprecipitated a 45 kd antigen from CLL-AAT cells (not shown). This antigen was identified by MALDI-MS as CD23, which is a known marker for CLL and activated B cells. ScFv-9 immunoprecipitated a 50 kd antigen from CLL-AAT cells (FIG. 12). This antigen was identified by µLC/MS/MS as OX-2/CD200, a known marker for B cells, activated CD4+ T cells, and thymocytes. OX-2/CD200 is also expressed on some non-lymphoid cells such as neurons and endothelial cells.

EXAMPLE 3

The capability of cells overexpressing OX-2/CD200 to shift the cytokine response from a Th1 response (IL-2, IFN-γ) to a Th2 response (IL-4, IL-10) was assessed in a mixed lymphocyte reaction using monocyte-derived macrophages/dendritic cells from one donor and blood-derived T cells from a different donor. As a source of OX-2/CD200-expressing cells, either OX-2/CD200 transfected EBNA cells as described below or CLL patient samples were used.

Transfection of 293-EBNA Cells

293-EBNA cells (Invitrogen) were seeded at $2.5 \times 10^6$ per 100 mm dish. 24 hours later the cells were transiently transfected using PolyFect® reagent (QIAGEN) according to the manufacturer's instructions. Cells were cotransfected with 7.2 µg of OX-2/CD200 cDNA in vector pCEP4 (Invitrogen) and 0.8 µg of pAdVAntage™ vector (Promega). As a negative control, cells were cotransfected with empty pCEP4 vector plus pAdVAntage™. 48 hours after transfection, approximately 90% of the cells expressed OX-2/CD200 on their surface as determined by flow cytometry with the scFv-9 antibody.

Maturation of Dendritic Cells/Macrophages from Blood Monocytes

Buffy coats were obtained from the San Diego Blood Bank and primary blood lymphocytes (PBL) were isolated using Ficoll. Cells were adhered for 1 hour in Eagles Minimal Essential Medium (EMEM) containing 2% human serum followed by vigorous washing with PBS. Cells were cultured for 5 days either in the presence of GM-CSF, IL-4 and IFN-γ or M-CSF with or without the addition of lipopolysaccharide (LPS) after 3 days. Matured cells were harvested and irradiated at 2000 RAD using a γ-irradiator (Shepherd Mark I Model 30 irradiator (Cs137)).

Mixed Lymphocyte Reaction

Mixed lymphocyte reactions were set up in 24 well plates using 500,000 dendritic cells/macrophages and 1×10$^6$ responder cells. Responder cells were T cell enriched lymphocytes purified from peripheral blood using Ficoll. T cells were enriched by incubating the cells for 1 hour in tissue culture flasks and taking the non-adherent cell fraction. 500,000 OX-2/CD200 transfected EBNA cells or CLL cells were added to the macrophages/dendritic cells in the presence or absence of 30 µg/ml anti-CD200 antibody (scFv-9 converted to full IgG) 2-4 hours before the lymphocyte addition. Supernatants were collected after 48 and 68 hours and analyzed for the presence of cytokines.

Conversion of scFv-9 to Full IgG

Light chain and heavy chain V genes of scFv-9 were amplified by overlap PCR with primers that connect the variable region of each gene with human lambda light chain constant region gene, and human IgG1 heavy chain constant region CH1 gene, respectively. Variable regions of light chain gene and heavy chain gene of scFv-9 were amplified with specific primers and the human lambda light chain constant region gene and the IgG1 heavy chain constant region CH1 gene were separately amplified with specific primers as follows:

```
                                     (SEQ ID NO: 103)
R9VL-F1 QP:
5' GGC CTC TAG ACA GCC TGT GCT GAC TCA GTC

GCC CTC 3';

(SEQ ID NO: 104)
R9VL/hCL2-rev:
5' CGA GGG GGC AGC TTG GGC TGA CCT GTG AC

GGT CAG CTG GGT C 3';

(SEQ ID NO: 105)
R9VL/hCL2-F:
5' GAC CCA GCT GAC CGT CAC AGG TCA GCC CAA

GGC TGC CCC CTC G 3';

(SEQ ID NO: 106)
R9VH-F1:
5' TCT AAT CTC GAG CAG CAG CAG CTG ATG GAG TCC

G 3';

(SEQ ID NO: 107)
R9VH/hCG-rev:
5' GAC CGA TGG GCC CTT GGT GGA GGC TGA GGA

GAC GGT GAC CAG GGT GC 3';

(SEQ ID NO: 108)
R9VH/hCG-F:
5' GCA CCC TGG TCA CCG TCT CCT CAG CCT CCA

CCA AGG GCC CAT CGG TC 3';

(SEQ ID NO: 109)
hCL2-rev:
5' CCA CTG TCA GAG CTC CCG GGT AGA AGT C 3';

(SEQ ID NO: 110)
hCG-rev:
5' GTC ACC GGT TCG GGA AGT AGT C 3'.
```

Amplified Products were Purified and Overlap PCR was Performed.

Final products were digested with Xba I/Sac I (light chain) and Xho I/Pin AI (heavy chain) and cloned into a human Fab expression vector, PAX243hGL (see published International Application WO 2004/078937, the disclosure of which is incorporated herein by this reference). DNA clones were analyzed for PCR errors by DNA sequencing. The hCMV IE promoter gene was inserted at Not I/Xho I site (in front of the heavy chain). The vector was digested with Xba I/Pin AI/EcoR I/Nhe I and a 3472 bp fragment containing the light chain plus the hCMV IE promoter and the heavy chain gene was transferred to an IgG1 expression vector at the Xba I/Pin AI site.

Cytokine Analysis

The effect of the scFv-9 converted to full IgG on the cytokine profile in the mixed lymphocyte reaction was determined.

Cytokines such as IL-2, IFN-γ, IL-4, IL-10 and IL-6 found in the tissue culture supernatant were quantified using ELISA. Matched capture and detection antibody pairs for each cytokine were obtained from R+D Systems (Minneapolis, Minn.), and a standard curve for each cytokine was produced using recombinant human cytokine. Anti-cytokine capture antibody was coated on the plate in PBS at the optimum concentration. After overnight incubation, the plates were washed and blocked for 1 hour with PBS containing 1% BSA and 5% sucrose. After 3 washes with PBS containing 0.05% TWEEN®, supernatants were added at dilutions of two-fold or ten-fold in PBS containing 1% BSA. Captured cytokines were detected with the appropriate biotinylated anti-cytokine antibody followed by the addition of alkaline phosphatase conjugated streptavidin and SigmaS substrate. Color development was assessed with an ELISA plate reader (Molecular Devices).

Figure 14:
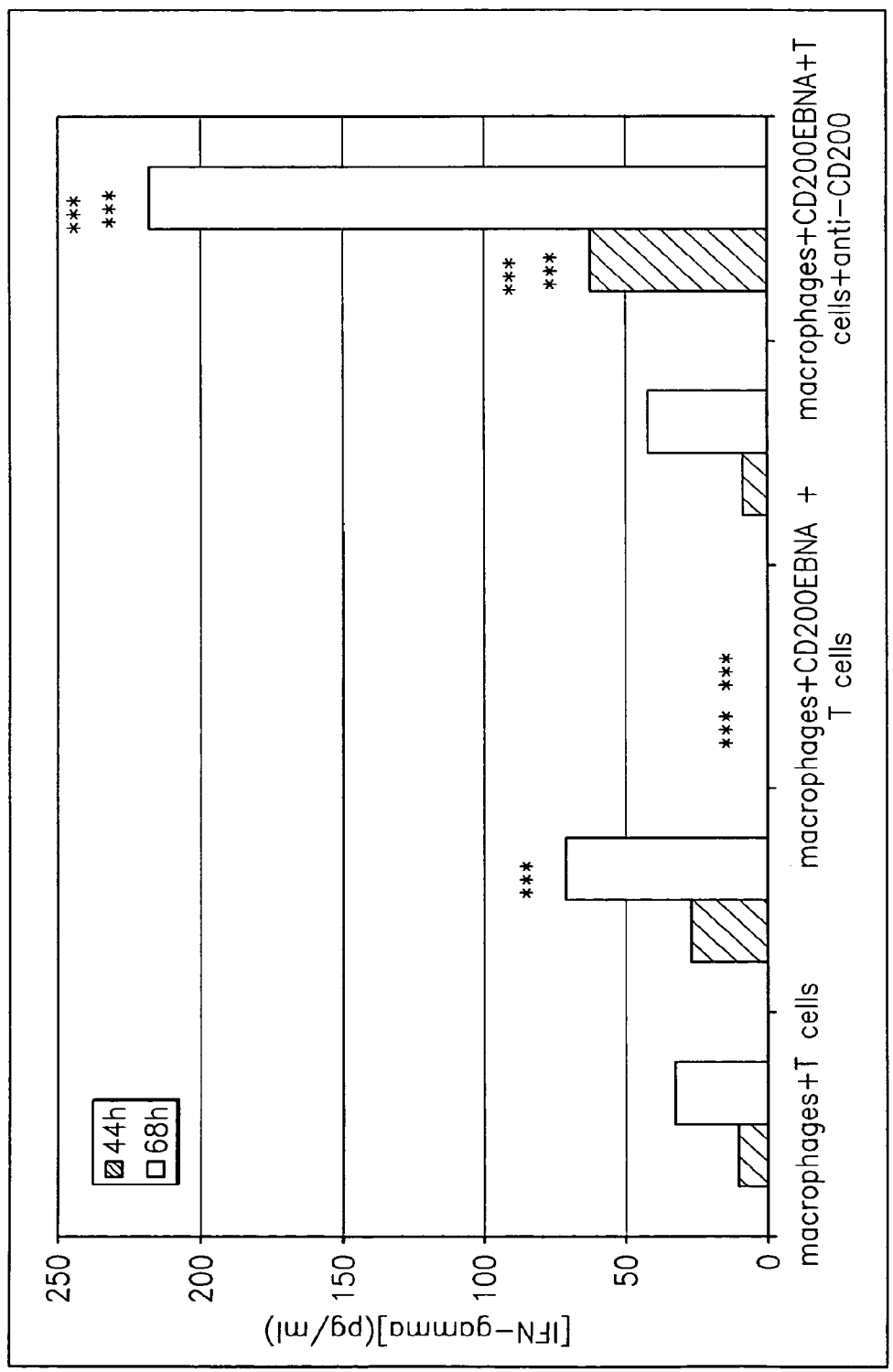
FIG. 14 shows that the presence of OX-2/CD200 transfected cells resulted in down-regulation of Th1 cytokines such as IL-2 and IFN-γ. Addition of the anti-OX-2/CD200 antibody at 30 µg/ml fully restored the Th1 response.

As shown in FIG. 14, the presence of OX-2/CD200 transfected but not untransfected cells resulted in down-regulation of Th1 cytokines such as IL-2 and IFN-γ. Addition of the anti-CD200 antibody at 30 µg/ml fully restored the Th1 response, indicating that the antibody blocked interaction of OX-2/CD200 with its receptor.

Figure 15:
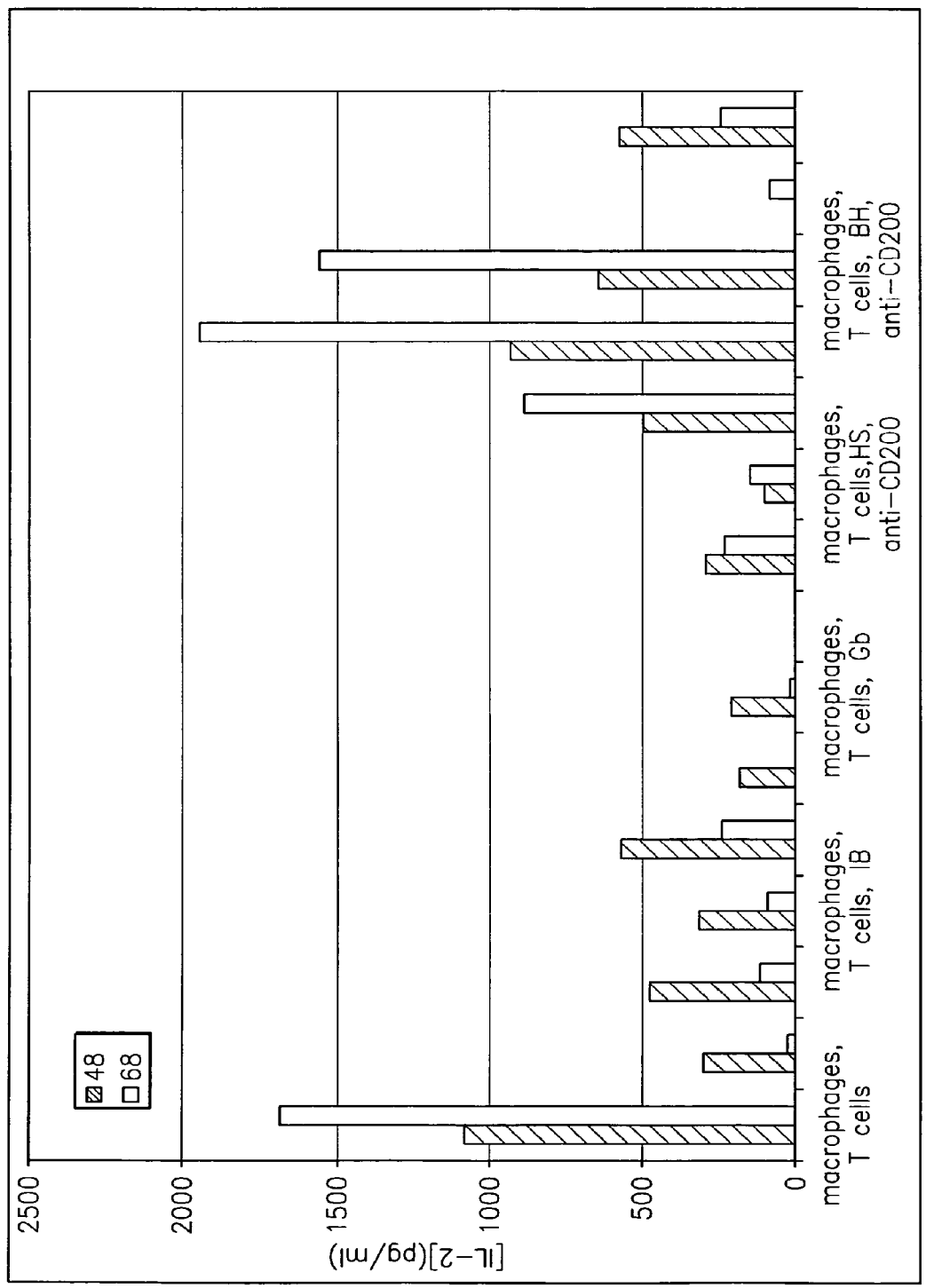
FIG. 15 shows that the presence of CLL cells in a mixed lymphocyte reaction resulted in down-regulation of the Th1 response for IL-2.
Figure 16:
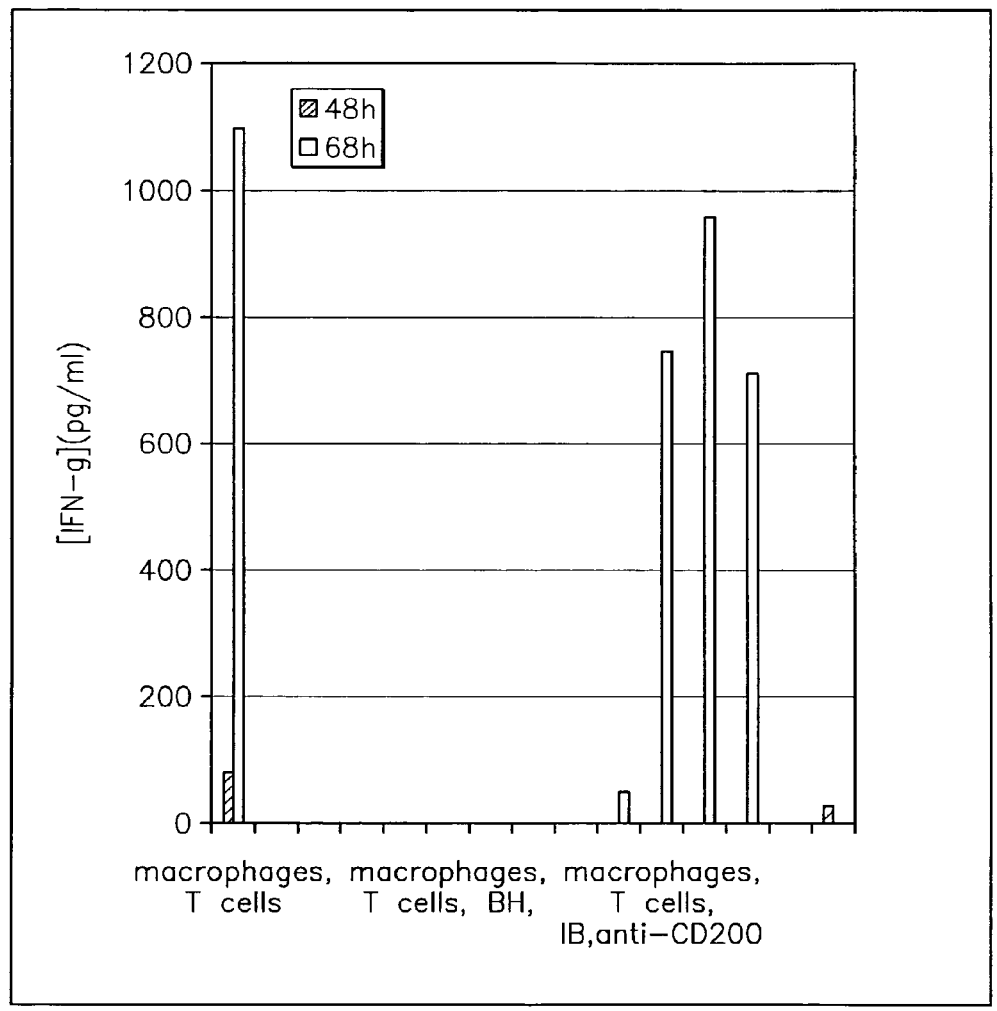
FIG. 16 shows that the presence of CLL cells in a mixed lymphocyte reaction resulted in down-regulation of the Th1 response for IFN-γ.

As set forth in FIGS. 15 and 16, the presence of CLL cells in a mixed lymphocyte reaction resulted in down-regulation of the Th1 response. (FIG. 15 shows the results for IL-2; FIG. 16 shows the results for IFN-γ). This was not only the case for cells over-expressing OX-2/CD200 (IB, EM, HS, BH), but also for CLL cells that did not over-express OX-2/CD200 (JR, JG and GB) (the expression levels for these cells are set forth in FIG. 11). However, the anti-CD200 antibody only restored the Th1 response in cells over-expressing OX-2/CD200, indicating that for patients over-expressing OX-2/CD200, abrogating OX-2/CD200 interaction with its receptor on macrophages was sufficient to restore a Th1 response. In patients that did not over-express OX-2/CD200, other mechanisms appeared to be involved in down-regulating the Th1 response.

Animal Models to Test an Effect of Anti-CD200 on Tumor Rejection

Figure 17A:
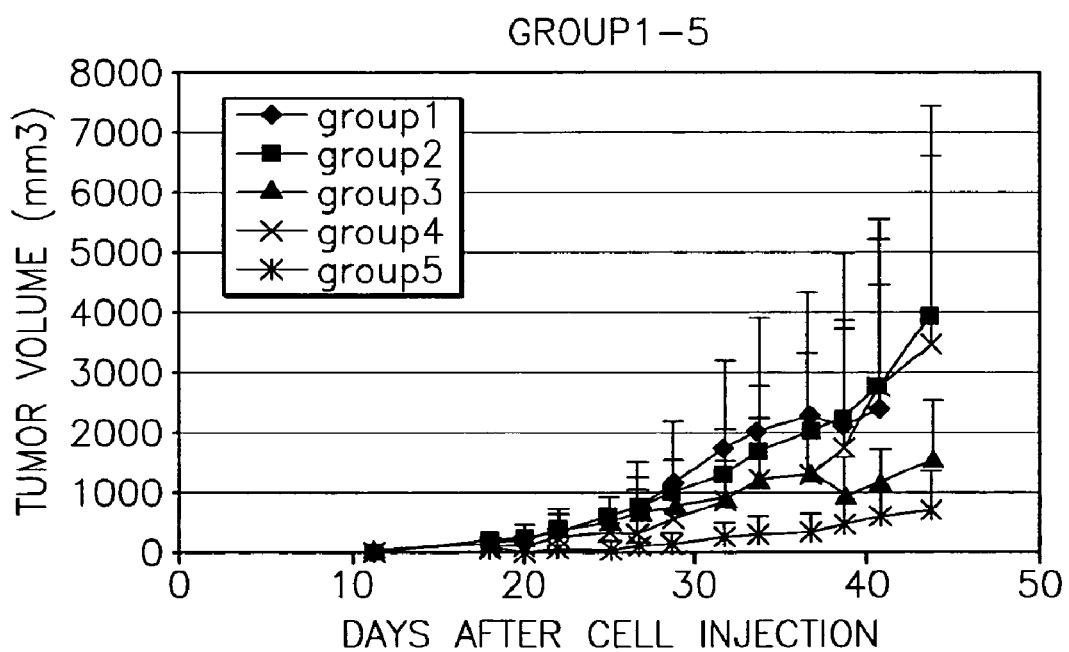
FIGS. 17A and B show the mean+/−SD of tumor volumes for all groups of NOD/SCID mice were injected subcutaneously with $4 \times 10^6$ RAJI cells either in the presence or absence of human.
Figure 17B:
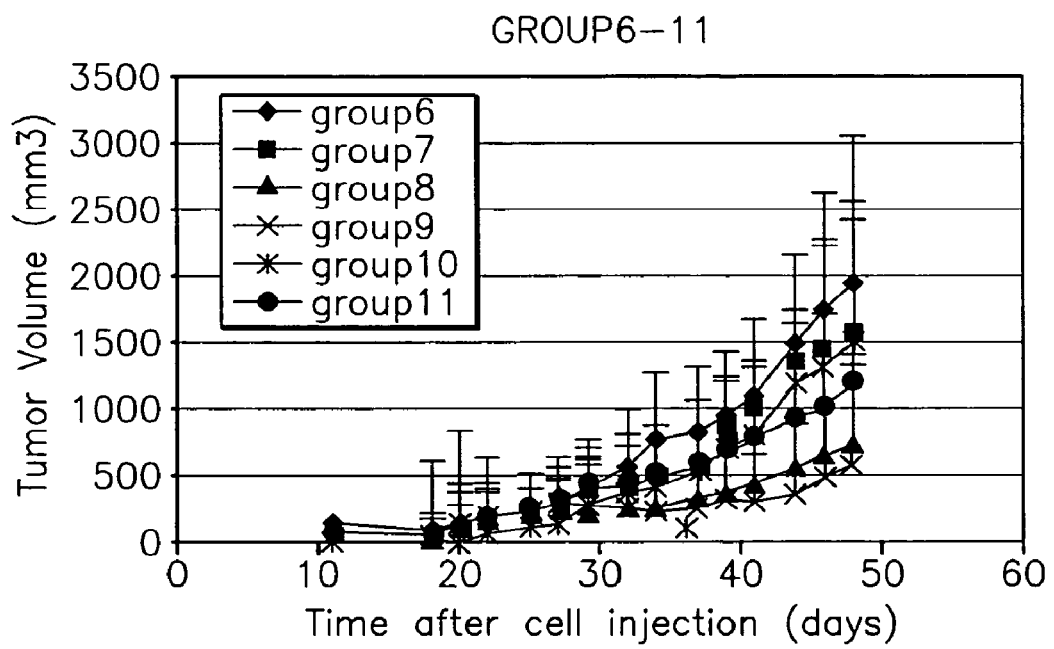
Figure 19A:
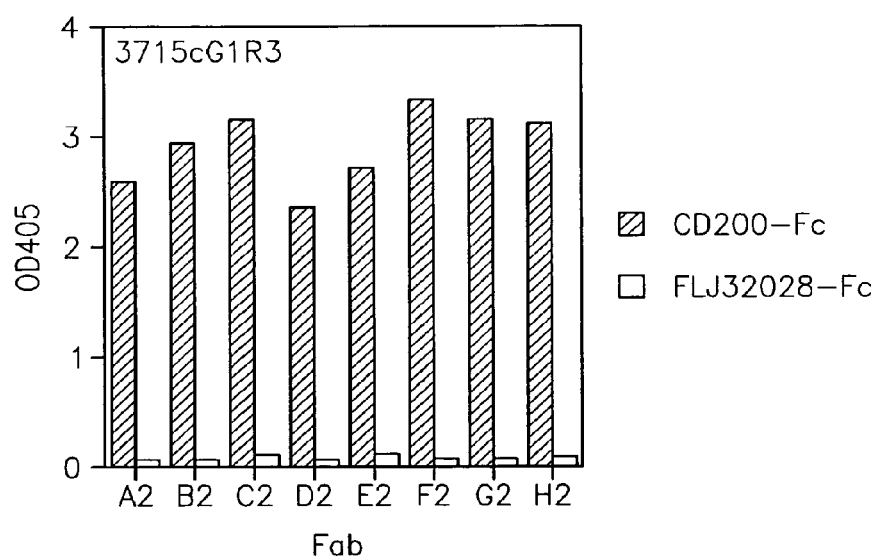
FIG. 19A shows ELISA results of representative IgG1 kappa clones after round 3 panning on CD200-Fc captured on goat anti-mouse IgG Fc antibody.
Figure 19B:
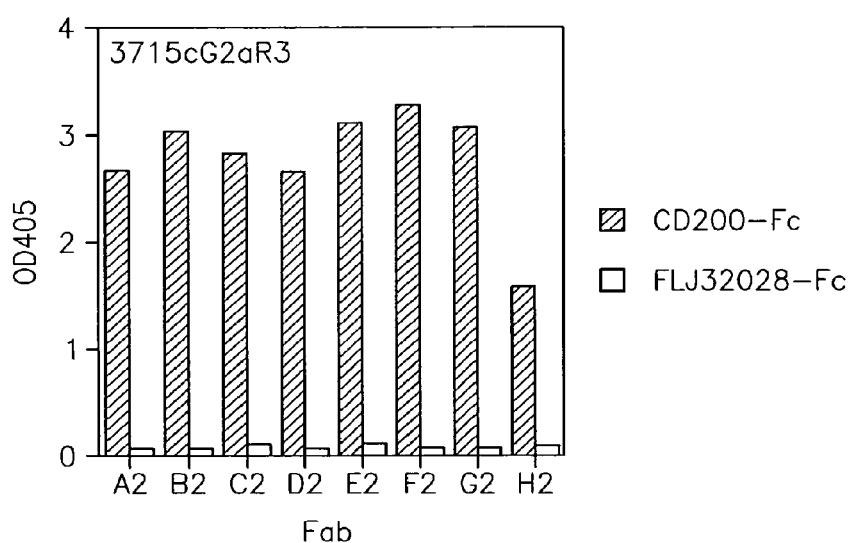
FIG. 19B shows ELISA results of representative IgG2a kappa clones after round 3 panning on CD200-Fc captured on goat anti-mouse IgG Fc antibody.
Figure 19C:
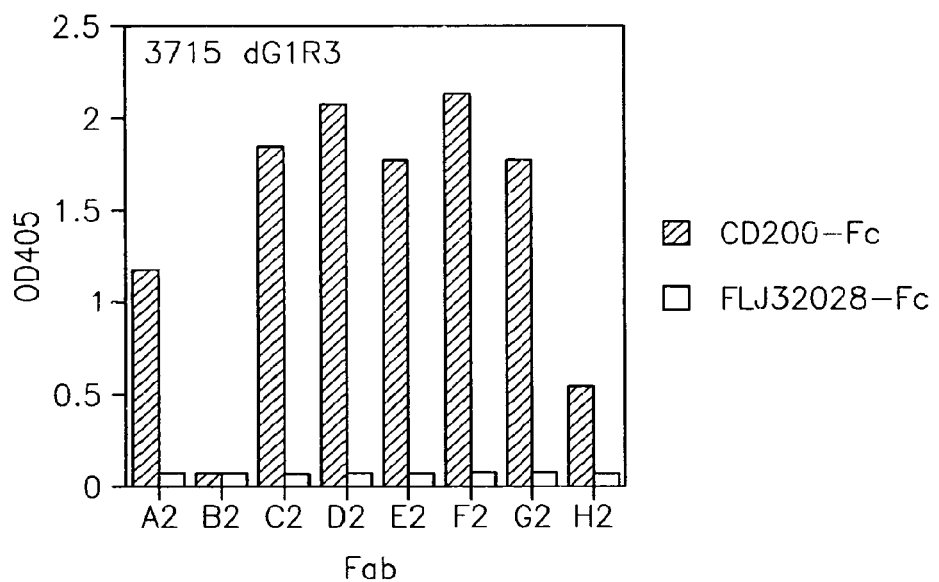
FIG. 19C shows ELISA results of representative IgG1 kappa clones after round 3 panning on CD200-Fc directly coated on microtiter wells.
Figure 19D:
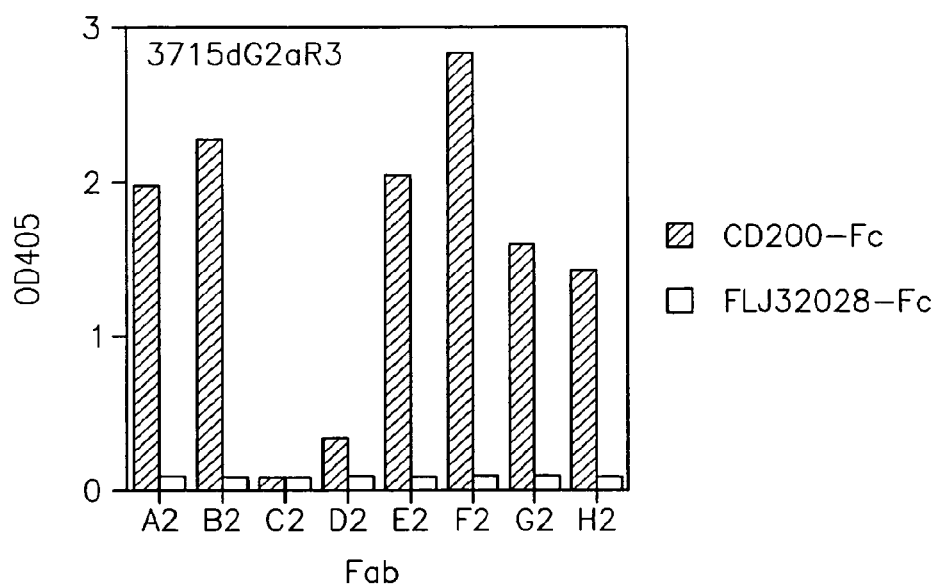
FIG. 19D shows ELISA results of representative IgG2a kappa clones after round 3 panning on CD200-Fc directly coated on microtiter wells.
Figure 20A:
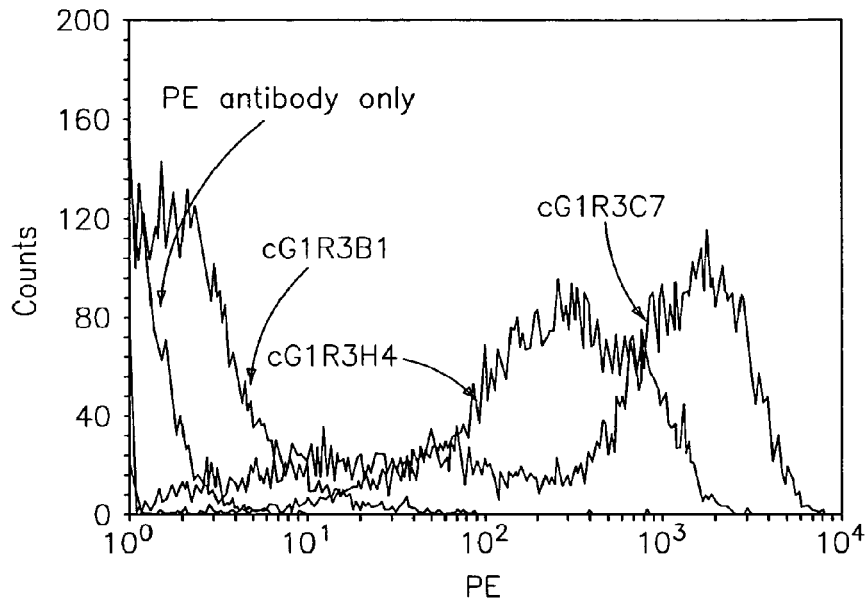
FIG. 20A shows flow cytometry results of representative IgG1 clones selected on CD200-Fc captured with goat anti-mouse IgG Fc.
Figure 20B:
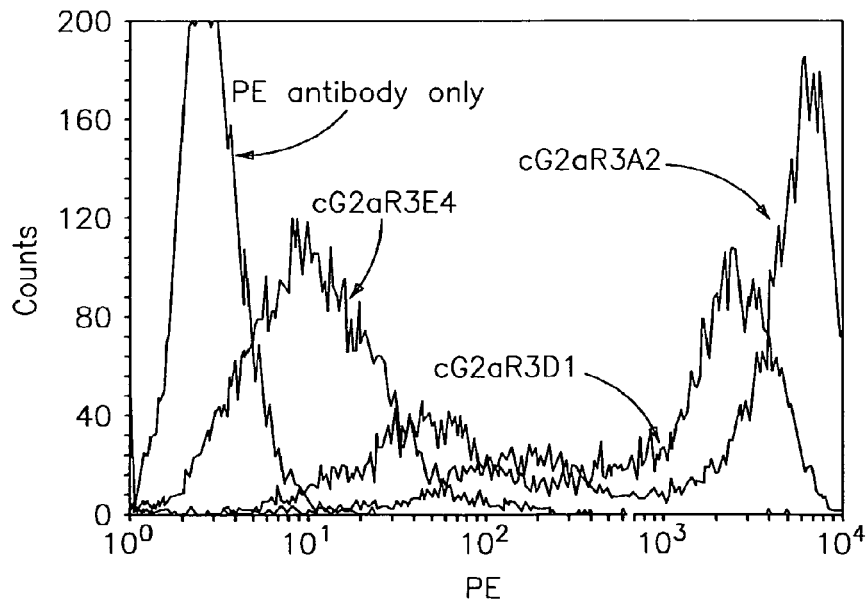
FIG. 20B shows flow cytometry results of representative IgG2a clones selected on CD200-Fc captured with goat anti-mouse IgG Fc.
Figure 20C:
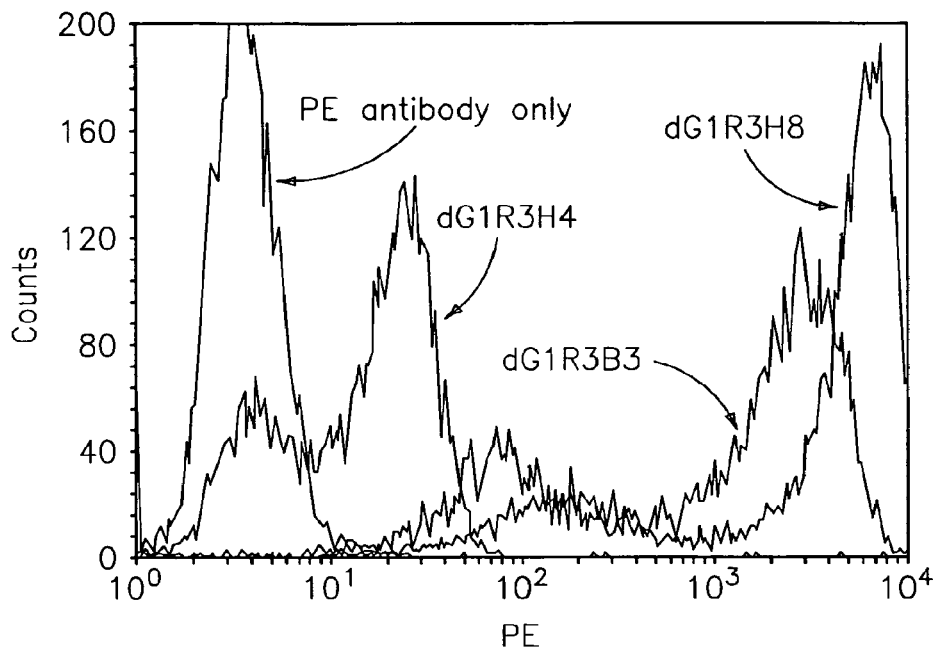
FIG. 20C shows flow cytometry results of representative IgG1 clones selected on directly coated CD200-Fc.
Figure 20D:
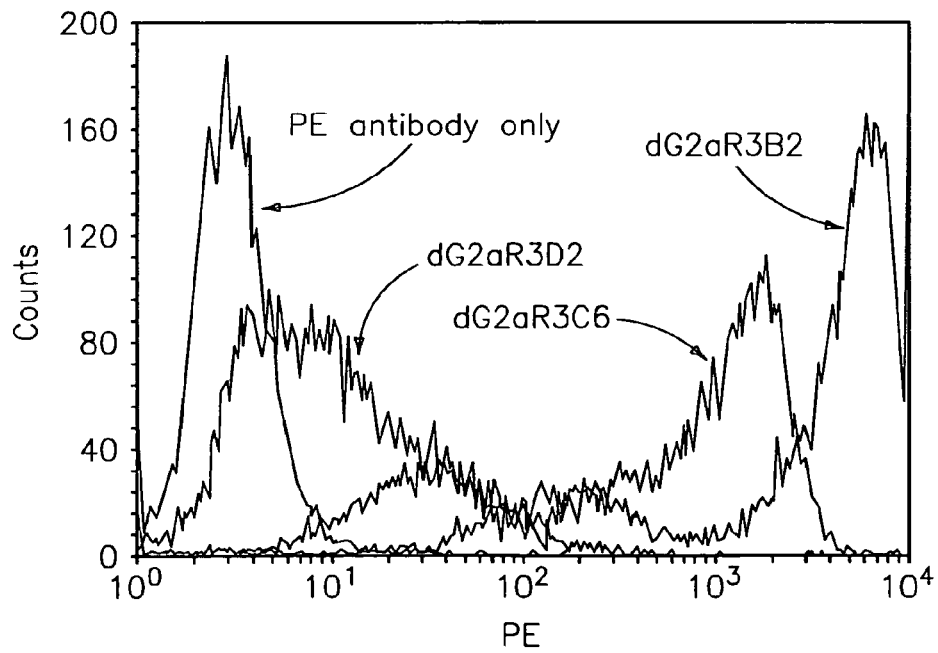
FIG. 20D shows flow cytometry results of representative IgG2a clones selected on directly coated CD200-Fc.

A model was established in which RAJI lymphoma tumor growth is prevented by the simultaneous injection of PBL's. NOD/SCID mice were injected subcutaneously with 4×10$^6$ RAJI cells either in the presence or absence of human PBL's from different donors at 1×10$^6$, 5×10$^6$ or 10×10$^6$ cells. Tumor length and width as well as body weight was determined 3 times a week. Mean+/−SD of tumor volumes for all groups is shown in FIGS. 17A and B. Statistical analysis was performed using 2 parametric tests (Student's t-test and Welch's test) and one non-parametric test, the Wilcox test. Results of the statistical analysis are found in FIG. 18. RAJI cells form subcutaneous tumors with acceptable variation. Rejection is dependent on the specific donor and the PBL cell number. $1 \times 10^6$ PBL's were insufficient to prevent tumor growth. Donor 2 at $5 \times 10^6$ PBL's from day 22-43 and donor 3 at $5 \times 10^6$ or $1 \times 10^7$ PBL's starting at day 36 significantly reduced tumor growth. Donor 4 is very close to being significant after day 48.

To test for an effect of anti-CD200, RAJI cells are stably transfected with CD200. Animals are injected as described in the previous paragraph. In the presence of cD200-transfected cells, tumors grow even in the presence of human PBL's. Anti-CD200 antibody is administered to evaluate tumor rejection in this model.

Also, a liquid tumor model is established. RAJI cells are injected intraperitoneally into NOD/SCID mice. Cells disseminate to bone marrow, spleen, lymph node and other organs resulting in paralysis. Concurrent injection of human PBL's prevents or slows tumor growth. Tumor growth is monitored by assessing the mice for signs of movement impairment and paralysis. Once these signs are observed, mice are sacrificed and the number of tumor cells is assessed in various organs including bone marrow, spleen, lymph nodes and blood by FACS analysis and PCR.

Similar to the subcutaneous model, CD200 transfected cells are injected intraperitoneally. They grow even in the presence of human PBL's. Treatment with anti-CD200 results in tumor rejection or slower tumor growth.

EXAMPLE 4

Library Construction

A mouse was immunized alternately with baculovirus expressed recombinant CD200 extracellular domain fused to mouse IgG Fc (CD200-Fc) (Orbigen Inc., San Diego, Calif.) and 293-EBNA cells transiently transfected with a vector containing full length CD200. Total RNA was prepared from mouse spleen using TRI reagent (Molecular Research Center, Inc., Cincinnati, Ohio) according to the manufacturer's protocol. Messenger RNA (mRNA) was purified using Oligotex (QIAGEN Inc., Valencia, Calif.) according to the manufacturer's manual. First strand cDNA was synthesized using SuperScript II RTase (Invitrogen Life Technologies, Carlsbad, Calif.) according to the manufacturer's protocol. First strand cDNA was digested with restriction endonuclease and second strand cDNA was synthesized according to the method fully described in published PCT application WO03/025202A2, published Mar. 27, 2003. Second strand cDNA was cleaned up with PCR purification kit (QIAGEN) and single primer amplification was performed according to the method described in published PCT application WO03/025202A2, published Mar. 27, 2003. Amplified products were pooled and purified with PCR purification kit. Kappa light chain was digested with Xba I and BspE I, and IgG1 and IgG2a heavy chains were digested with Xho I and Bln I. Digested fragments were purified from the agarose gel using Gel extraction kit (QIAGEN) and cloned into PAX313m/hG vector as described in published PCT application WO/04078937A2 published Sep. 16, 2004.

Library Panning

The libraries (IgG 1 kappa and IgG2a kappa) were panned on CD200-Fc either directly coated on the microtiter wells (Costar Group, Bethesda, Md.) or captured with goat anti-mouse IgG Fc specific antibody (Sigma-Aldrich Corp., St. Louis, Mo.). For the preparation of library phage, electro-competent XL1-Blue cells (Stratagene, La Jolla, Calif.) were electroporated with library DNA and grown in SOC medium for 1 hour and in SB medium for 2 hours with carbenicillin. Phage production was induced with the addition of VCS M13 helper phage (Amersham Biosciences Corp., Piscataway, N.J.) and 1 mM IPTG at 30° C. overnight. The culture was spun down and phage was precipitated with 4% polyethylene glycol and 3% NaCl. The phage was spun down and resuspended in 1% BSA/PBS containing unrelated antigen, FLJ32028 that is also baculovirus expressed extracellular domain fused to mouse IgG Fc (FLJ32028-Fc) (Orbigen, San Diego), as a soluble competitor. For the panning on directly coated CD200-Fc, four wells were coated with 100 µl of CD200-Fc (5 µg/ml in 0.1 M NaHCO$_3$ pH8.6) at 4° C. overnight. The wells were washed 5 times with phosphate buffered saline (PBS) pH7.0 and blocked with 1% bovine serum albumin (BSA)/PBS at 37° C. for 1 hr. For the panning on CD200-Fc captured on goat anti-mouse IgG Fe, four microtiter wells were coated with 100 µl goat anti-mouse IgG Fc (20 µg/ml in PBS) at 4° C. overnight. The wells were washed 5 times with PBS and incubated with 100 µl CD200-Fc (20 µg/ml in PBS) for 1 hour at 37° C. The wells were washed 5 times with PBS and blocked with 1% BSA/PBS at 37° C. for 1 hour. For both panning, the blocker was replaced with the mixture of soluble Fabs obtained from the panning of another library (the library described in Example 3 of PCT application serial No. PCT/US04/17118 filed Jun. 2, 2004 (not yet published), the entire disclosure of which is incorporated herein by this reference) on FLJ32028 to mask epitopes on mouse IgG Fc and the wells were incubated for 30 min at 37° C. These masking Fabs were shown to also bind to CD200-Fc. Library phage was added on top of the masking Fabs and the wells were incubated for approximately 1.5 hours at 37° C. The unbound phage was washed with PBS with increasing stringency (3 times in the first round, 5 times in the 2" round and 10 times in the $3^{rd}$ and the $4^{th}$ rounds) with 5 minute incubation and pipetting up and down 5 times for each wash. The bound phage was eluted twice with 100 µl 0.1 M HCl with 1 mg/ml BSA, pH2.2 and neutralized with 2 M Tris Base pH 11.5. The freshly grown ER2738 cells were infected with eluted phage and titrated onto LB agarose plates containing carbenicillin and glucose. The remaining phage was propagated overnight at 30-37° C. with the addition of VCS M13 helper phage and 1 mM IPTG for the next round of panning.

Library Screening

Ninety five colonies from round 3 and 4 titration plates were grown in 1 ml SB containing 12.5 µg/ml tetracycline and 50 µg/ml carbenicillin for approximately 6 hours at 37° C. VCS M13 helper phage was added and the culture was incubated for 2 hours at 37° C. 1 mM IPTG and 70 µg/ml kanamycin were added and Fab-phage production was induced at 30° C. overnight. Microtiter wells were coated with 50 µl of rabbit anti-mouse IgG F(ab')2 (4 µg/ml in PBS), CD200-Fc (4 µg/ml in 0.1 M NaHCO$_3$ pH8.6), or FLJ32028-Fc (4 µg/ml in 0.1 M NaHCO$_3$ pH8.6) at 4° C. overnight. The wells were washed 3 times with PBS and blocked with 100 µl 1% BSA/PBS for 1 hour at 37° C. The culture was spun down. The blocker was replaced with the culture supernatant containing Fab-phage and the wells were incubated for 1.5~2 hours at 37° C. The remaining Fab-phage was stored at −80° C. for flow cytometry. The plates were washed 3 times with PBS and the binding was detected with 50 µl alkaline phosphatase (AP)-conjugated goat anti-mouse IgG F(ab')$_2$ antibody (Pierce)(1:500 in 1% BSA/PBS) for 1 hr at 37° C. The plates were washed 3 times with PBS and developed with AP substrate (Sigma-Aldrich) in pNPP buffer. Almost all of the clones from round 3 were already specifically positive to CD200 (FIG. 19A-D). Clones were also screened by high throughput flow cytometry analysis. One hundred micro-liter 293 cells transiently transfected with CD200 ($1 \times 10^5$ cells)

were aliquoted into 96 well plate (Costar). Fifty micro-liter Fab-phage was added to the cells and mixed by pipetting and incubated on ice for 30 minutes. The cells were washed twice with 1% BSA/PBS containing 0.01% NaN3. The cells were resuspended in 100 µl PE-conjugated goat anti-mouse IgG antibody (Sigma-Aldrich) in 1% BSA/PBS containing 0.01% NaN3 and incubated on ice for 30 minutes. The cells were washed twice with 1% BSA/PBS containing 0.01% NaN3 and resuspended in 200 µl 1% paraformaldehyde in PBS. Representative clones showing positive binding to CD200 expressing cells are shown in FIG. 20A-D.

DNA sequences were analyzed and deduced amino acid sequences of the heavy chain were grouped according to the complementarity determining region 3 (CDR3) (FIG. 21A, B). They were divided into 17 groups.

Figure 22:
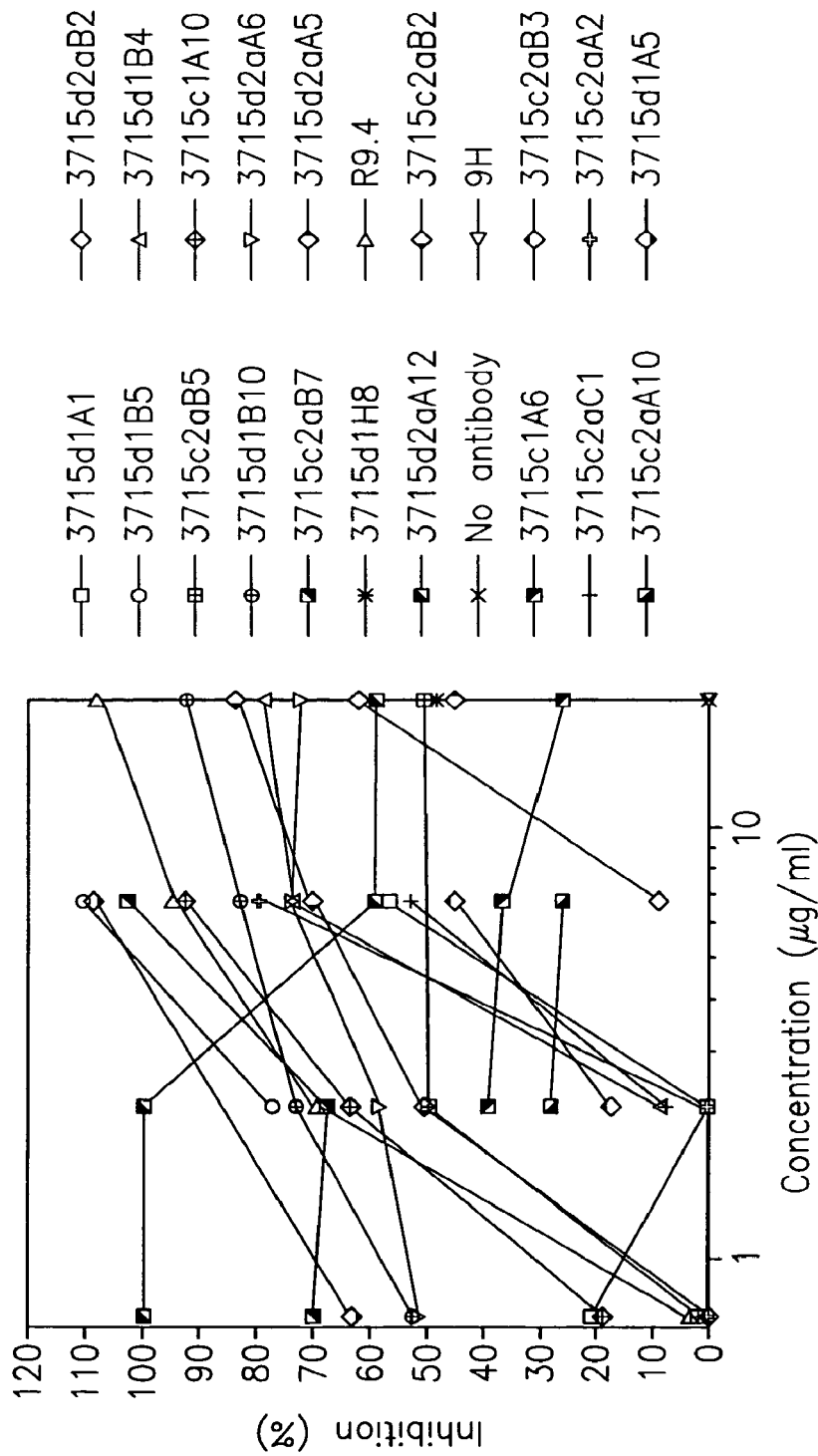
FIG. 22 shows ability of selected clones to block the interaction of CD200 with its receptor (CD200R) in a fluorescent bead assay.

Fluorescent Bead Assay 23 clones were selected for further analysis. They were cG2aR3B5, dG1R3A5, cG2aR3A2, dG2aR3B2, dG1R3A1, cG2aR3A1, cG2aR3B, dG1R3B, cG1R3A, cG1R3A, cG1R3A1, dG1R3B, dG1R3B, cG1R3c, dG2aR3c, dG2aR3A1, cG2aR3B, cG2aR3B, dG1R3B, cG2aR3B, cG2aR3c, dG1R3H, and dG2aR3A6. DNA of selected Fabs were digested with Spe I/Nhe I for gene III removal and soluble Fab expression and purification. The purified Fabs were evaluated for their ability to block the interaction of CD200 with its receptor (CD200R) in a fluorescent bead assay. TransFluoSpheres carboxylate-modified microspheres (488/645) (Molecular Probes Invitrogen Detection Technologies, Eugene, Oreg.) were coated with streptavidin followed by a biotin-labeled anti-human Fc antibody and baculovirus-produced CD200-Fc protein. 293 cells were transiently transfected with CD200R. Cell surface expression was confirmed by FACS analysis. 1 million CD200-coated beads were pre-incubated with various amounts of anti-CD200 Fabs or chimeric IgG for 10 minutes before the addition of 50,000 CD200R transfected cells. After 30 minute incubation at 37° C., the cells were washed in Tris buffer containing 1% BSA and analyzed using a FACS Calibur. Fabs c1A10, c2aB7, and d1A5 showed the best blocking of CD200 and CD200R interaction at 6.7 µg/ml of Fab (FIG. 22). These clones are referred to as cG1R3A10, cG2aR3B7 and dG1R3A5, respectively in FIGS. 21A and/or B.

Chimerization and IgG Conversion

Figure 24:
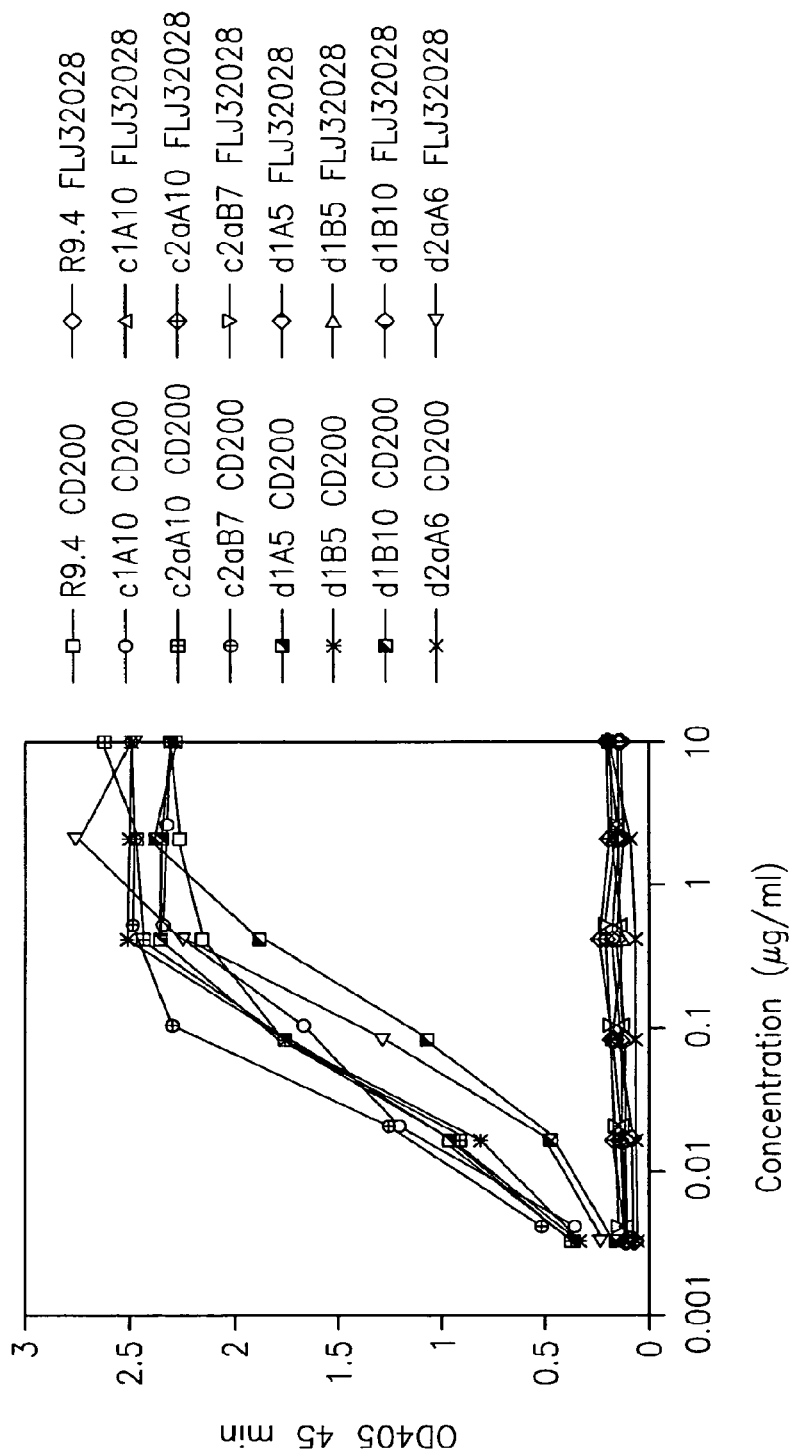
FIG. 24 shows ELISA results of chimeric IgG obtained from the culture supernatant of a small-scale transient transfection.

Six antibodies were selected for chimerization and IgG conversion. (See FIG. 23.) They were c1A10 (cG1R3A10), c2aA10 (cG2aR3A10), c2aB7 (cG2aR3B7), d1A5 (dG1R3A5), d1B5 (dG1R3B5), and d1B10 (dG1R3B10). For the chimerization, overlap PCR was performed to connect mouse kappa chain variable region and human kappa chain constant region. Mouse heavy chain variable region was amplified with a 3' primer that contains a partial human IgG1 constant region and Apa I site for cloning. Amplified kappa chain fragments and heavy chain fragments were cloned into PAX243hGK vector (see published International Application WO 2004/078937) that contains human IgG1 constant region at Xba I/Not I for kappa light chain and Xho I/Apa I for heavy chain fragment. Binding of chimeric Fab to CD200 was confirmed by ELISA and flow cytometry. These chimeric Fabs were converted into IgG by insertion of human cytomegalovirus immediate early promoter (hCMV IE Pro) sequence for the heavy chain expression at Not I/Xho I, then the transfer of the light chain and heavy chain into a human IgG1 expression vector at Xba I/Pin AI sites. This vector has an additional hCMV IE Pro sequence upstream Xba I site for the light chain expression in mammalian cells. The DNA sequences were confirmed and maxi prep DNA was prepared using HiSpeed Maxi prep columns (QIAGEN) for mammalian cell transfection. Transient transfection was performed in 293-EBNA cells using Effectene (QIAGEN) according to the manufacturer's protocol with the addition of pAdVAntage vector (Promega US, Madison, Wis.). Stable cell line transfection was performed in NS0 cells using Effectene according to the manufacturer's protocol. After a small scale transient transfection, culture supernatant for each antibody was tested by ELISA (FIG. 24). After a large scale transient transfection, each IgG was purified from the culture supernatant by anti-human IgG F(ab')$_2$ affinity column using FPLC (Amersham Biosciences).

Figure 25:
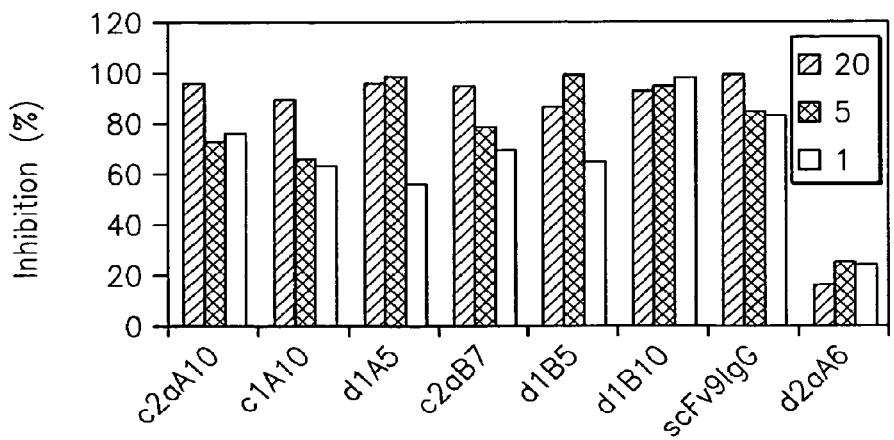
FIG. 25 shows bead inhibition assay results on purified IgG showing that all antibodies directed against CD200 blocked the receptor ligand interaction very well.

The purified IgG were tested in bead inhibition assay as described for the Fab's. All antibodies directed against CD200 blocked the receptor ligand interaction very well as shown below in FIG. 25.

Mixed Lymphocyte Reaction

Figure 26C:
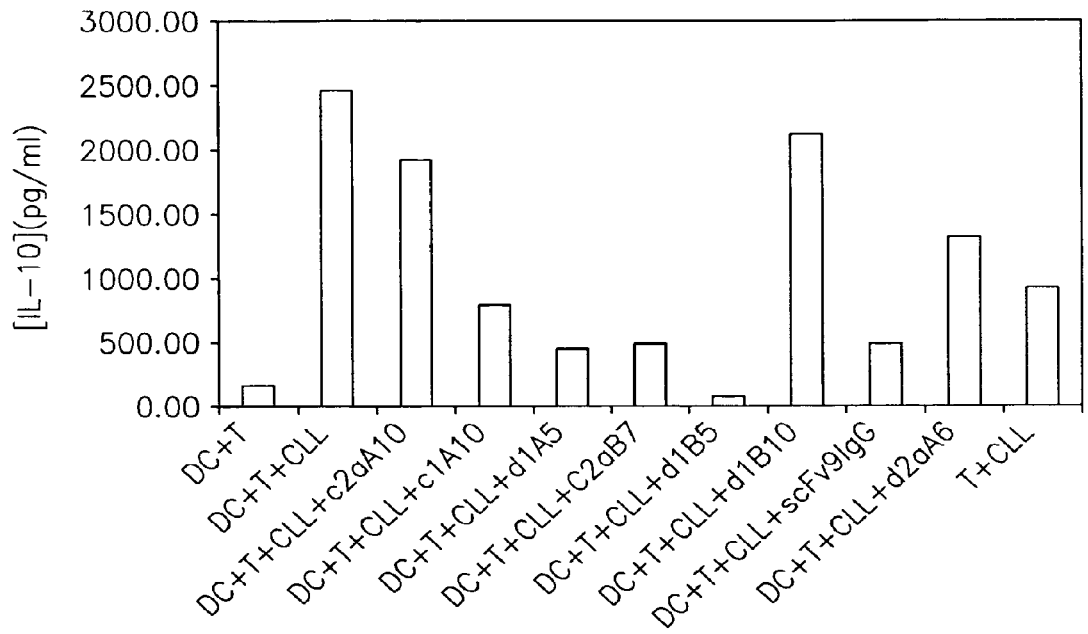
FIG. 26C shows that IL-10 production was downregulated in the presence of the antibodies.
Figure 26A:
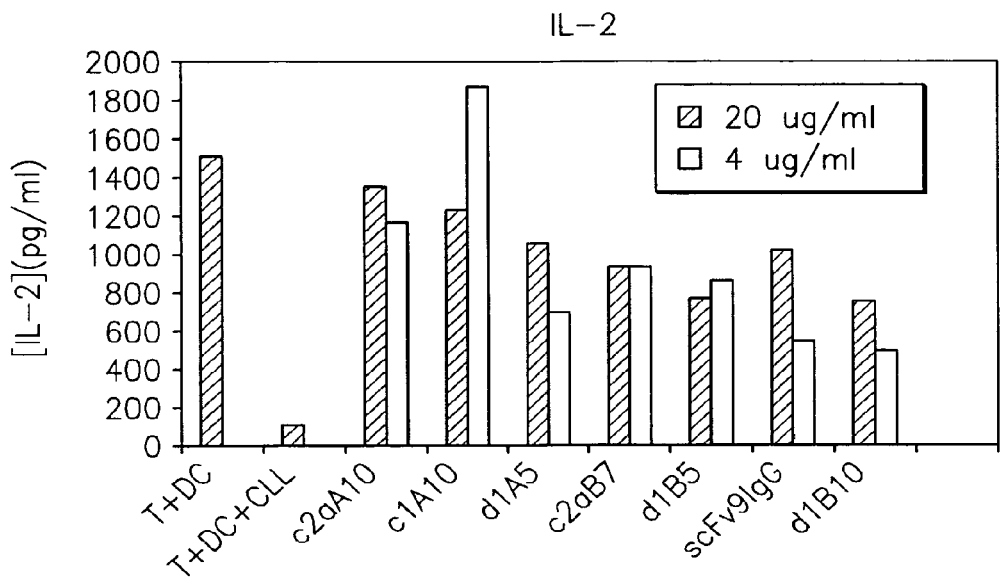
FIGS. 26A and 26B show that the presence of CLL cells completely abrogated IFN-gamma and most of IL-2 production observed in the mixed lymphocyte reaction but that the presence of any of the antibodies allowed for production of these Th1 cytokines.
Figure 26B:
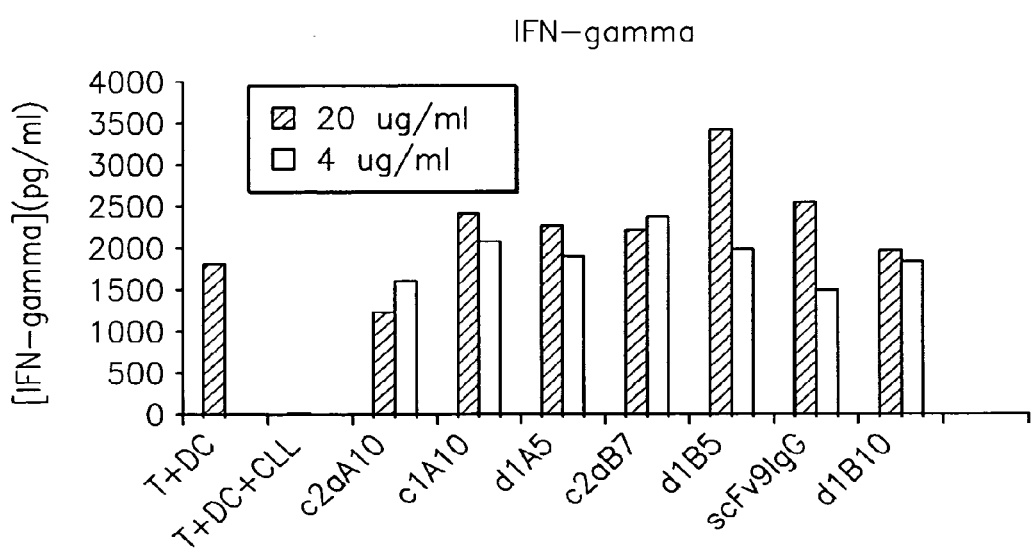

Whether blocking of CD200 interaction with its receptor also prevents the cytokine shift from Th1 to Th2 observed in mixed lymphocytes reactions in the presence of CD200 was evaluated. Buffy coats were obtained from the San Diego Blood Bank and primary blood lymphocytes (PBL) were isolated using HISTOPAQUE® (Sigma-Aldrich). Cells were adhered for 1 h in EMEM containing 2% human serum followed by vigorous washing with PBS. Cells were cultured for 5 days in the presence of GM-CSF, IL-4 and IFN-γ. Matured cells were harvested and irradiated at 2000 RAD using a γ-irradiator (University of California San Diego). Mixed lymphocyte reactions were set up in 24 well plates using 500,000 dendritic cells and 1×10$^6$ responder cells. Responder cells were T cell enriched lymphocytes purified from peripheral blood using HISTOPAQUE®. T cells were enriched by incubating the cells for 1 hour in tissue culture flasks and taking the non-adherent cell fraction. Five hundred thousand CD200 expressing primary irradiated CLL cells were added to the dendritic cells in the presence or absence of various amounts of anti-CD200 antibodies 2-4 hours before the lymphocyte addition. Supernatants were collected after 48 and 68 hours and cytokines such as IL-2, IFN-γ, IL-4, IL-10 and IL-6 were quantified using ELISA. Matched capture and detection antibody pairs for each cytokine were obtained from R+D Systems (Minneapolis), and a standard curve for each cytokine was produced using recombinant human cytokine. Anti-cytokine capture antibody was coated on the plate in PBS at the optimum concentration. After overnight incubation, the plates were washed and blocked for 1 h with PBS containing 1% BSA and 5% sucrose. After 3 washes with PBS containing 0.05% TWEEN®, supernatants were added at the indicated dilutions in PBS containing 1% BSA. Captured cytokines were detected with the appropriate biotinylated anti-cytokine antibody followed by the addition of alkaline phosphatase conjugated streptavidin and SigmaS substrate. Color development was assessed with an ELISA plate reader (Molecular Devices Corp., Sunnyvale, Calif.). As shown in the FIG. 26A, B, the presence of CLL cells completely abrogated IFN-gamma and most of IL-2 production observed in the mixed lymphocyte reaction. Presence of any of the antibodies allowed for production of these Th1 cytokines (FIG. 26A, B). In contrast, IL-10 production was downregulated in the presence of the antibodies. (See FIG. 26C.)

Antibody-Dependent Cell-Mediated Cytotoxicity Assay

Figure 27:
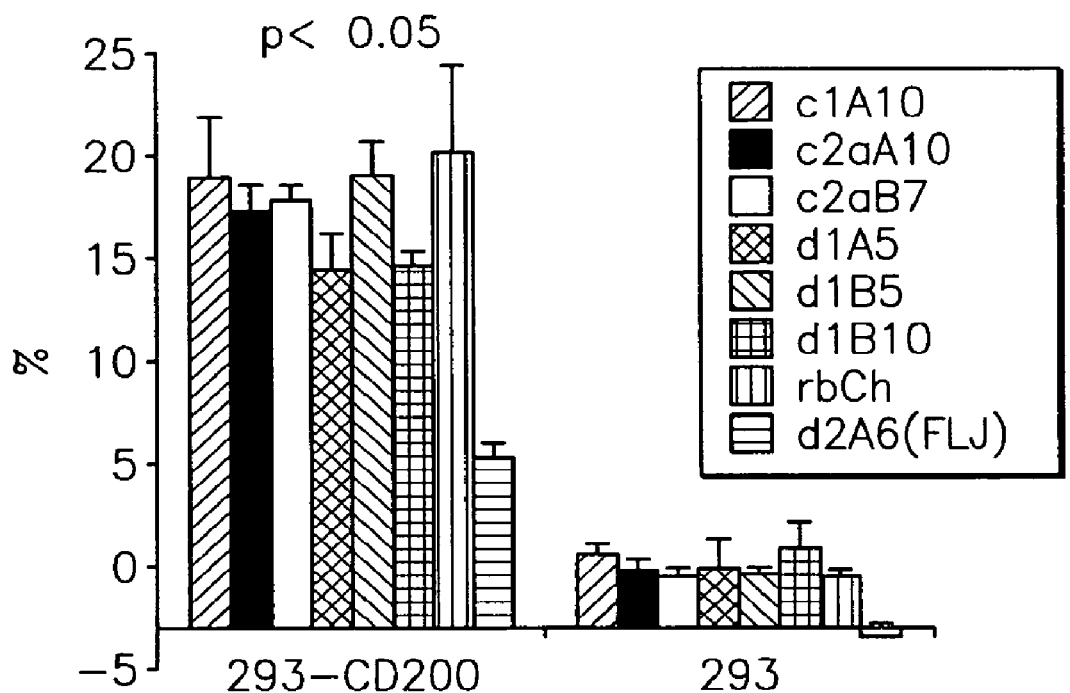
FIG. 27 shows the ability to kill CD200 expressing tumor cells in an antibody-dependent cell-mediated cytotoxicity assay (ADCC). All of the mouse chimeric CD200 antibodies produced similar levels of lysis when cultured with CD200 positive cells.

Furthermore, the six chimeric mouse anti-CD200 antibodies were evaluated for their ability to kill CD200 expressing tumor cells in an antibody-dependent cell-mediated cytotoxicity assay (ADCC). 293-EBNA cells transfected with CD200 were labeled with 100 µCi/million cells in 0.5 ml medium for 1 hr at 37° C. After 3 washes, cells were counted, resuspended in medium (RPMI supplemented with 10% human AB serum) at 0.2 million/ml and 50 μl (10,000 cells/well) was dispensed in triplicate into a 96 well round bottom plate. 20 μl of anti-CD200 antibodies were dispensed into each well so as to achieve a final concentration of 20 μg/ml. Peripheral blood mononuclear cells (effector cells) were isolated on a Ficoll gradient, red blood cells were lysed with ammonium chloride, washed and resuspended in culture medium and 50 μl of cells were dispensed into each well. The assay plates were spun (1,500 rpm/5 minutes/low brake) and transferred to the cell culture incubator. After 4 hours, assay plates were spun as before. 36 μl of the supernatants were transferred to pico plates and mixed with 250 μl microscint-20 cocktail, and placed on the orbital shaker for 2 minutes and read on a Top count. As illustrated in the FIG. 27, all of the mouse chimeric CD200 antibodies produced similar levels of lysis when cultured with CD200 positive cells. No lysis was observed with CD200 negative cells. In addition, the extent of lysis was statistically significant (p<0.05) when compared to isotype control antibody, d2A6 (anti-FLJ32028 antibody).

REFERENCES

The following references are incorporated herein by reference to more fully describe the state of the art to which the present invention pertains. Any inconsistency between these publications below or those incorporated by reference above and the present disclosure shall be resolved in favor of the present disclosure.

1) Agarwal, et al., (2003). Disregulated expression of the Th2 cytokine gene in patients with intraoral squamous cell carcinoma. Immunol Invest 32:17-30.
2) Almasri, N M et al. (1992). Am J Hemato 140 259-263.
3) Contasta, et al., (2003). Passage from normal mucosa to adenoma and colon cancer: alteration of normal sCD30 mechanisms regulating TH1/TH2 cell functions. Cancer Biother Radiopharm 18:549-557.
4) Gorczynski, et al., (1998). Increased expression of the novel molecule OX-2 is involved in prolongation of murine renal allograft survival. Transplantation 65:1106-1114.
5) Gorczynski, et al., (2001). Evidence of a role for CD200 in regulation of immune rejection of leukaemic tumour cells in C57BL/6 mice. Clin Exp Immunol 126:220-229.
6) Hainsworth, J D (2000). Oncologist 2000; 5(5):376-84.
7) Inagawa, et al., (1998). Mechanisms by which chemotherapeutic agents augment the antitumor effects of tumor necrosis factor: involvement of the pattern shift of cytokines from Th2 to Th1 in tumor lesions. Anticancer Res 18:3957-3964.
8) Ito, et al., (1999). Lung carcinoma: analysis of T helper type 1 and 2 cells and T cytotoxic type 1 and 2 cells by intracellular cytokine detection with flow cytometry. Cancer 85:2359-2367.
9) Kiani, et al., (2003). Normal intrinsic Th1/Th2 balance in patients with chronic phase chronic myeloid leukemia not treated with interferon-alpha or imatinib. Haematologica 88:754-761.
10) Lauerova, et al., (2002). Malignant melanoma associates with Th1/Th2 imbalance that coincides with disease progression and immunotherapy response. Neoplasma 49:159-166.
11) Maggio, et al., (2002). Chemokines, cytokines and their receptors in Hodgkin's lymphoma cell lines and tissues. Ann Oncol 13 Suppl 1:52-56.
12) Nilsson, K (1992). Burn Cell. 5(1):25-41.
13) Podhorecka, et al., (2002). T type 1/type 2 subsets balance in B-cell chronic lymphocytic leukemia—the three-color flow cytometry analysis. Leuk Res 26:657-660.
14) Pu, Q Q and Bezwoda, W (2000). Anticancer Res. 20(4): 2569-78.
15) Smyth, et al., (2003). Renal cell carcinoma induces prostaglandin E2 and T-helper type 2 cytokine production in peripheral blood mononuclear cells. Ann Surg Oncol 10:455-462.
16) Tatsumi, et al., (2002). Disease-associated bias in T helper type 1 (Th1)/Th2 CD4(+) T cell responses against MAGE-6 in HLA-DRB10401(+) patients with renal cell carcinoma or melanoma. J Exp Med 196:619-628.
17) Walls A V et al. (1989). Int. J. Cancer 44846-853.
18) Winter, et al., (2003). Tumour-induced polarization of tumour vaccine-draining lymph node T cells to a type 1 cytokine profile predicts inherent strong immunogenicity of the tumour and correlates with therapeutic efficacy in adoptive transfer studies. Immunology 108:409-419.

It will be understood that various modifications may be made to the embodiments disclosed herein. For example, as those skilled in the art will appreciate, the specific sequences described herein can be altered slightly without necessarily adversely affecting the functionality of the polypeptide, antibody or antibody fragment used in binding OX-2/CD200. For instance, substitutions of single or multiple amino acids in the antibody sequence can frequently be made without destroying the functionality of the antibody or fragment. Thus, it should be understood that polypeptides or antibodies having a degree of homology greater than 70% to the specific antibodies described herein are within the scope of this disclosure. In particularly useful embodiments, antibodies having a homology greater than about 80% to the specific antibodies described herein are contemplated. In other useful embodiments, antibodies having a homology greater than about 90% to the specific antibodies described herein are contemplated. Therefore, the above description should not be construed as limiting, but merely as exemplifications of preferred embodiments. Those skilled in the art will envision other modifications within the scope and spirit of this disclosure.

We claim:

1. A method of treating a human afflicted with a cancer comprising cancer cells expressing human CD200 protein, the method comprising:
    administering to the human a therapeutic composition comprising an anti-CD200 antibody or antigen-binding fragment thereof, the antibody or antigen-binding fragment being present in an amount sufficient to promote production of one or more Th1 cytokines in the human to thereby treat the cancer, wherein the anti-CD200 antibody or antigen-binding fragment thereof binds to human CD200 protein expressed on the cancer cells and wherein the anti-CD200 antibody or antigen-binding fragment thereof inhibits the interaction between human CD200 and the human CD200 receptor,
    wherein the anti-CD200 antibody or antigen-binding fragment thereof comprises:
    (A): (i) a light chain polypeptide comprising: a light chain CDR3 having the sequence set forth in residues 91-99 of SEQ ID NO: 209; a light chain CDR2 having the sequence set forth in residues 52-58 of SEQ ID NO: 209; and a light chain CDR1 having the sequence set forth in residues 26-36 of SEQ ID NO: 209; and (ii) a heavy chain polypeptide comprising: a heavy chain CDR3 having the sequence set forth in SEQ ID NO: 195; a heavy chain CDR2 having the sequence set forth in SEQ ID NO: 174; and a heavy chain CDR1 having the sequence set forth in SEQ ID NO: 149; or
    (B): (i) a light chain polypeptide having an amino acid sequence comprising the amino acid sequence depicted in SEQ ID NO: 209; and (ii) a heavy chain polypeptide having an amino acid sequence comprising the amino acid sequence depicted in SEQ ID NO: 203.

2. A method of killing cancer cells expressing human CD200 protein, the method comprising:
    administering to a human afflicted with a cancer comprising cancer cells expressing human CD200 protein a therapeutic composition comprising an anti-CD200 antibody, the antibody in an amount sufficient to kill cancer cells expressing human CD200 protein in the human by antibody-dependent cell-mediated cytotoxicity (ADCC), wherein the anti-CD200 antibody comprises a human heavy chain Fc region that effectuates ADCC, and wherein the anti-CD200 antibody binds to human CD200 protein expressed by the cancer cell,
    wherein the anti-CD200 antibody comprises:
    (A): (i) a light chain polypeptide comprising: a light chain CDR3 having the sequence set forth in residues 91-99 of SEQ ID NO: 209; a light chain CDR2 having the sequence set forth in residues 52-58 of SEQ ID NO: 209; and a light chain CDR1 having the sequence set forth in residues 26-36 of SEQ ID NO: 209; and (ii) a heavy chain polypeptide comprising: a heavy chain CDR3 having the sequence set forth in SEQ ID NO: 195; a heavy chain CDR2 having the sequence set forth in SEQ ID NO: 174; and a heavy chain CDR1 having the sequence set forth in SEQ ID NO: 149; or
    (B): (i) a light chain polypeptide having an amino acid sequence comprising the amino acid sequence depicted in SEQ ID NO: 209; and (ii) a heavy chain polypeptide having an amino acid sequence comprising the amino acid sequence depicted in SEQ ID NO: 203.

3. A method of treating a human afflicted with a cancer comprising cancer cells expressing CD200 protein, the method comprising:
administering to the human a therapeutic composition comprising an anti-CD200 antibody, the antibody in an amount sufficient to treat the cancer by (i) promoting production of one or more Th1 cytokines in the human and (ii) killing cancer cells expressing human CD200 protein in the human by complement dependent cytotoxicity (CDC) or antibody-dependent cell-mediated cytotoxicity (ADCC), wherein the anti-CD200 antibody comprises a human heavy chain Fc region that effectuates CDC or ADCC, and wherein the anti-CD200 antibody binds to human CD200 protein expressed by the cancer cell,
wherein the anti-CD200 antibody comprises:
(A): (i) a light chain polypeptide comprising: a light chain CDR3 having the sequence set forth in residues 91-99 of SEQ ID NO: 209; a light chain CDR2 having the sequence set forth in residues 52-58 of SEQ ID NO: 209; and a light chain CDR1 having the sequence set forth in residues 26-36 of SEQ ID NO: 209; and (ii) a heavy chain polypeptide comprising: a heavy chain CDR3 having the sequence set forth in SEQ ID NO: 195; a heavy chain CDR2 having the sequence set forth in SEQ ID NO: 174; and a heavy chain CDR1 having the sequence set forth in SEQ ID NO: 149; or
(B): (i) a light chain polypeptide having an amino acid sequence comprising the amino acid sequence depicted in SEQ ID NO: 209; and (ii) a heavy chain polypeptide having an amino acid sequence comprising the amino acid sequence depicted in SEQ ID NO: 203.

* * * * *